United States Patent
Wong et al.

(10) Patent No.: US 9,624,547 B2
(45) Date of Patent: Apr. 18, 2017

(54) SALIVARY TRANSCRIPTOMIC AND PROTEOMIC BIOMARKERS FOR BREAST CANCER DETECTION

(75) Inventors: David T. Wong, Beverly Hills, CA (US); Lei Zhang, Los Angeles, CA (US); Hua Xiao, Irvine, CA (US); Hui Zhou, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/025,110

(22) Filed: Feb. 10, 2011

(65) Prior Publication Data

US 2011/0212851 A1 Sep. 1, 2011

Related U.S. Application Data

(60) Provisional application No. 61/303,200, filed on Feb. 10, 2010.

(51) Int. Cl.
*C12Q 1/68* (2006.01)
*G01N 33/574* (2006.01)

(52) U.S. Cl.
CPC ..... *C12Q 1/6886* (2013.01); *G01N 33/57415* (2013.01); *C12Q 2600/158* (2013.01)

(58) Field of Classification Search
None
See application file for complete search history.

(56) References Cited

U.S. PATENT DOCUMENTS

2010/0279419 A1* 11/2010 Streckfus et al. ............. 436/64
2012/0010823 A1 1/2012 Shaw

FOREIGN PATENT DOCUMENTS

| WO | WO 2006/048291 A2 | 5/2006 |
|----|-------------------|--------|
| WO | WO 2007/033367 A2 | 3/2007 |
| WO | WO 2008/021290 A2 | 2/2008 |
| WO | WO 2008/079269 A2 | 7/2008 |
| WO | WO 2008/155661 A2 | 12/2008 |
| WO | WO 2009/039023 A2 | 5/2009 |
| WO | WO 2010/017515 A2 | 2/2010 |

OTHER PUBLICATIONS

Paik, Molecular Profiling of Breast Cancer; Curr Opin Obstet Gynecol, vol. 18, pp. 59-63, 2006.*
Li et al., Salivary transcriptome diagnostics for oral cancer detection; Clinical Cancer Research, vol. 10, pp. 8442-8450, 2004.*
Parkkila et al., Competitive Time-Resolved ImmunofluorometricAssay for Quantifying Carbonic Anhydrase VI in Saliva; Clin Chem, vol. 39, No. 10, 2154-2157, 1993.*
Mayr et al., Widespread shortening of 3' UTRs by alternative cleavage and polyadenylation activates oncogenes in cancer cells, Cell, vol. 138, pp. 673-684, 2009.*
Screen capture showing probes for S100A8, CSTA, GRM1, TPT1, GRIK1, H6PD, MDM4 and CA6 from NCBI Gene Expression Ominibus platform accession No. GPL96, accessed Aug. 11, 2014.*
Zhang, Lei et al. "Discovery and Preclinical Validation of Salivary Transcriptomic and Proteomic Biomarkers for the Non-Invasive Detection of Breast Cancer" *PLoS ONE*. vol. 5, No. 12 p. 107 (2010).
Anon. 'GeneChip® Human Genome Arrays' Affymetrix Data Sheet [retrieved on Jun. 30, 2014]. Retrieved from Internet <http://media.affymetrix.com/support/technical/datasheets/human_datasheet.pdf> copyright 2003-2004.

* cited by examiner

*Primary Examiner* — Addison D Ault
(74) *Attorney, Agent, or Firm* — Riverside Law LLP

(57) ABSTRACT

Presented herein are biomarkers related to breast cancer. The presently identified salivary biomarkers create the basis for a breast cancer detection bioassay with sensitivity and specificity. Means and methods for evaluating the data generated using multiple biomarkers in order to validate findings and further use of the multiplexed breast cancer assay in clinical, diagnostic and therapeutic uses is also included.

5 Claims, 6 Drawing Sheets

| Demographic Variable | Characteristics | Discovery Phase | | | Pre-validation Phase | | |
|---|---|---|---|---|---|---|---|
| | | Breast Cancer (n = 10) | Healthy Control (n = 10) | p-value | Breast Cancer (n = 30) | Healthy Control (n = 63) | p-value |
| Age (y) | Mean +/- SD | 52.256 +/- 10.44 | 51.66 +/- 10.31 | 0.89 | 52.74 +/- 12.11 | 52.52 +/- 12.16 | 0.66 |
| Gender | Female | 10 | 10 | | 30 | 63 | |
| Ethnicity | Caucasian | 5 (50%) | 8 (80%) | 0.44 | 19 (64.5%) | 53 (83.9%) | 0.07 |
| | African-American | 2 (20%) | 0 | | 1 (3.2%) | 4 (6.5%) | |
| | Asian | 0 | 0 | | 6 (19.4%) | 4 (6.5%) | |
| | Hispanic | 3 (30%) | 2 (20%) | | 0 | 1 (1.6%) | |
| | Other | | | | 4 (12.9%) | 1 (1.6%) | |
| Smoking | | 3 | 3 | | 10 (33.3%) | 24 (38.1%) | 1 |
| HRT | | | | | 10 (33.3%) | | |
| Menopausal Status | Pre | 5 | 5 | | 12 (40%) | 32 (50.8%) | 0.37 |
| | Post | 5 | 5 | | 18 (60%) | 31 (49.2%) | |

FIGURE 3

| Biomarker | P-Value | cv.err | Age | Ethnicity | Menopausal Status | Smoking Status | HRT | Reported Relation to Breast Cancer or Other Cancers |
|---|---|---|---|---|---|---|---|---|
| *CSTA* | 4.19E-13 | 0.333 | 0.16 | 0.78 | 0.24 | 0.95 | 0.08 | [50] |
| *TPT1* | 5.38E-05 | 0.251 | 0.30 | 0.60 | 0.13 | 0.87 | 0.17 | [51] |
| *IGF2BP1* | 2.57E-04 | 0.312 | 0.78 | 0.90 | 0.41 | 0.89 | 0.42 | [52] |
| *GRM1* | 6.57E-03 | 0.262 | 0.42 | 0.71 | 0.18 | 0.89 | 0.23 | [53] |
| *GRIK1* | 3.24E-02 | 0.237 | 0.70 | 0.80 | 0.36 | 0.88 | 0.20 | [54] |
| *H6PD* | 1.46E-03 | 0.262 | 0.57 | 0.73 | 0.30 | 0.76 | 0.21 | [55] |
| *MDM4* | 7.30E-04 | 0.297 | 0.55 | 0.79 | 0.27 | 0.89 | 0.25 | [56] |
| *S100A8* | 1.96E-03 | 0.272 | 0.54 | 0.86 | 0.31 | 0.88 | 0.22 | [57] |
| CA6 | 1.70E-03 | 0.427 | 0.76 | 0.21 | 0.51 | 0.81 | 1.00 | [58,59] |

FIGURE 4

| Biomarker | Oral Cancer | Lung Cancer | Pancreatic Cancer | Ovarian Cancer | Diabetes | pSS | Breast Cancer |
|---|---|---|---|---|---|---|---|
| *S100A8* | 0.341 | 0.246 | 0.704 | 0.049 | 0.700 | 0.798 | <0.001 |
| *CSTA* | 0.341 | 0.029 | 0.197 | 0.678 | 0.648 | 0.750 | <0.001 |
| *GRM1* | 0.341 | 0.242 | 0.126 | 0.523 | 0.419 | 0.061 | 0.001 |
| *TPT1* | 0.341 | 0.112 | 0.558 | 0.090 | 0.454 | 0.855 | <0.001 |
| *GRIK1* | 0.341 | 0.589 | 0.543 | 0.489 | 0.948 | 0.629 | 0.006 |
| *H6PD* | 0.343 | 0.517 | 0.475 | 0.293 | 0.330 | 0.101 | <0.001 |
| *IGF2BP1* | 0.341 | 0.102 | 0.316 | 0.275 | 0.697 | 0.820 | 0.002 |
| *MDM4* | 0.341 | 0.011 | 0.154 | 0.455 | 0.088 | 0.168 | 0.001 |

FIGURE 6

SEQUENCE LISTING

<160> NUMBER OF SEQ ID NOS: 57

<210> SEQ ID NO 1
<211> LENGTH: 532
<212> TYPE: DNA
<213> ORGANISM: Homo sapiens

<400> SEQUENCE: 1

```
gagaaaccag agactgtagc aactctggca gggagaagct gtctctgatg gcctgaagct      60
gtgggcagct ggccaagcct aaccgctata aaaaggagtc gcctctcagc cctgcatgtc     120
tcttgtcagc tgtctttcag aagacctggt ggggcaagtc cgtgggcatc atgttgaccg     180
agctggagaa agccttgaac tctatcatcg acgtctacca caagtactcc ctgataaagg     240
ggaatttcca tgccgtctac agggatgacc tgaagaaatt gctagagacc gagtgtcctc     300
agtatatcag gaaaaagggt gcagacgtct ggttcaagga gttggatatc aacactgatg     360
gtgcagttaa cttccaggag ttcctcattc tggtgataaa gatgggcgtg gcagcccaca     420
aaaaaagcca tgaagaaagc cacaaagagt agctgagtta ctgggcccag aggctgggcc     480
cctggacatg tacctgcaga ataataaagt catcaatacc tcaaaaaaaa aa             532
```

<210> SEQ ID NO 2
<211> LENGTH: 838
<212> TYPE: DNA
<213> ORGANISM: Homo sapiens

<400> SEQUENCE: 2

```
tgctgtttgt ggaaaataaa gcattctata ggcggagcta gtgaacgcct cttttaaaac      60
acgagtctcc acacttccct gttcactttg gttccagcat cctgtccagc aaagaagcaa     120
tcagccaaaa tgatacctgg aggcttatct gaggccaaac ccgccactcc agaaatccag     180
gagattgttg ataaggttaa accacagctt gaagaaaaaa caaatgagac ttacggaaaa     240
ttggaagctg tgcagtataa aactcaagtt gttgctggaa caattactca cattaaggta     300
cgagcaggtg ataataaata tatgcacttg aaagtattca aaagtcttcc cggacaaaat     360
gaggacttgg tacttactgg ataccaggtt gacaaaaaca aggatgacga gctgacgggc     420
ttttagcagc atgtacccaa agtgttctga ttccttcaac tggctactga gtcatgatcc     480
ttgctgataa atataaccat caataaagaa gcattctttt ccaaagaaat tatttcttca     540
attatttctc atttattgta ttaagcagaa attacctttc ctttctcaaa atcagtgtta     600
ttgctttaga gtataaactc catataaatt gatggcaatt ggaaatctta taaaaactag     660
tcaagcctaa tgcaactggc taaggatag taccaccctc accccacca taggcaggct       720 ggatcgtgga ctatcaattc accagcctcc ttgttccctg tggctgctga tacccaaca      780 ttccatctct accctcatac ttcaaaatta aatcaagtat tttacaaaaa aaaaaaa        838
```

-continued

<210> SEQ ID NO 3
<211> LENGTH: 6939
<212> TYPE: DNA
<213> ORGANISM: Homo sapiens

<400> SEQUENCE: 3

| | | | | | |
|---|---|---|---|---|---|
| agtgctgaag | aaagagggca | ctagtgtaca | gcccagatcg | catccttgca | ccgtctggat | 60 |
| tagagctgag | gcgtctgcaa | gccgagcgtg | gccacggtcc | tctggccccg | ggaccatagc | 120 |
| gctgtctacc | ccgactcagg | tactcagcag | catctagctc | accgctgcca | acacgacttc | 180 |
| cactgtactc | ttgatcaatt | taccttgatg | cactaccggt | gaagaacggg | gactcgaatt | 240 |
| cccttacaaa | cgcctccagc | ttgtagaggc | ggtcgtggag | gacccagagg | aggagacgaa | 300 |
| ggggaaggag | gcggtggtgg | aggaggcaaa | ggccttggac | gaccattgtt | ggcgaggggc | 360 |
| accactccgg | gagaggcggc | gctgggcgtc | ttggggggtgc | gcgccgggag | cctgcagcgg | 420 |
| gaccagcgtg | ggaacgcggc | tggcaggctg | tggacctcgt | cctcaccacc | atggtcgggc | 480 |
| tcctttttgtt | ttttttccca | gcgatctttt | tggaggtgtc | ccttctcccc | agaagccccg | 540 |
| gcaggaaagt | gttgctggca | ggagcgtcgt | ctcagcgctc | ggtggccaga | atggacggag | 600 |
| atgtcatcat | tggagccctc | ttctcagtcc | atcaccagcc | tccggccgag | aaagtgcccg | 660 |
| agaggaagtg | tggggagatc | agggagcagt | atggcatcca | gagggtggag | gccatgttcc | 720 |
| acacgttgga | taagatcaac | gcggacccgg | tcctcctgcc | caacatcacc | ctgggcagtg | 780 |
| agatccggga | ctcctgctgg | cactcttccg | tggctctgga | acagagcatt | gagttcatta | 840 |
| gggactctct | gatttccatt | cgagatgaga | aggatgggat | caaccggtgt | ctgcctgacg | 900 |
| gccagtccct | ccccccaggc | aggactaaga | agcccattgc | gggagtgatc | ggtcccggct | 960 |
| ccagctctgt | agccattcaa | gtgcagaacc | tgctccagct | cttcgacatc | ccccagatcg | 1020 |
| cttattcagc | cacaagcatc | gacctgagtg | acaaaacttt | gtacaaatac | ttcctgaggg | 1080 |
| ttgtcccttc | tgacactttg | caggcaaggg | ccatgcttga | catagtcaaa | cgttacaatt | 1140 |
| ggacctatgt | ctctgcagtc | cacacggaag | ggaattatgg | ggagagcgga | atggacgctt | 1200 |
| tcaaagagct | ggctgcccag | gaaggcctct | gtatcgccca | ttctgacaaa | atctacagca | 1260 |
| acgctgggga | gaagagcttt | gaccgactct | tgcgcaaact | ccgagagagg | cttcccaagg | 1320 |
| ctagagtggt | ggtctgcttc | tgtgaaggca | tgacagtgcg | aggactcctg | agcgccatgc | 1380 |
| ggcgccttgg | cgtcgtgggc | gagttctcac | tcattggaag | tgatgatgg | gcagacagag | 1440 |
| atgaagtcat | tgaaggttat | gaggtggaag | ccaacggggg | aatcacgata | aagctgcagt | 1500 |
| ctccagaggt | caggtcattt | gatgattatt | tcctgaaact | gaggctggac | actaacacga | 1560 |
| ggaatccctg | gttccctgag | ttctggcaac | atcggttcca | gtgccgcctt | ccaggacacc | 1620 |
| ttctggaaaa | tcccaacttt | aaacgaatct | gcacaggcaa | tgaaagctta | gaagaaaact | 1680 |
| atgtccagga | cagtaagatg | gggttttgtca | tcaatgccat | ctatgccatg | gcacatgggc | 1740 |
| tgcagaacat | gcaccatgcc | ctctgccctg | gccacgtggg | cctctgcgat | gccatgaagc | 1800 |
| ccatcgacgg | cagcaagctg | ctggacttcc | tcatcaagtc | ctcattcatt | ggagtatctg | 1860 |
| gagaggaggt | gtggtttgat | gagaaaggag | acgctcctgg | aagttatgat | atcatgaatc | 1920 |
| tgcagtacac | tgaagctaat | cgctatgact | atgtgcacgt | tggaacctgg | catgaaggag | 1980 |
| tgctgaacat | tgatgattac | aaaatccaga | tgaacaagag | tggagtggtg | cggtctgtgt | 2040 |
| gcagtgagcc | ttgcttaaag | ggccagatta | aggttatacg | gaaggagaa | gtgagctgct | 2100 |
| gctggatttg | cacggcctgc | aaagagaatg | aatatgtgca | agatgagttc | acctgcaaag | 2160 |

```
cttgtgactt gggatggtgg cccaatgcag atctaacagg ctgtgagccc attcctgtgc    2220
gctatcttga gtggagcaac atcgaatcca ttatagccat cgccttttca tgcctgggaa    2280
tccttgttac cttgtttgtc accctaatct ttgtactgta ccgggacaca ccagtggtca    2340
aatcctccag tcgggagctc tgctacatca tcctagctgg catcttcctt ggttatgtgt    2400
gcccattcac tctcattgcc aaacctacta ccacctcctg ctacctccag cgcctcttgg    2460
ttggcctctc ctctgcgatg tgctactctg ctttagtgac taaaaccaat cgtattgcac    2520
gcatcctggc tggcagcaag aagaagatct gcacccggaa gcccaggttc atgagtgcct    2580
gggctcaggt gatcattgcc tcaattctga ttagtgtgca actaaccctg gtggtaaccc    2640
tgatcatcat ggaaccccct atgcccattc tgtcctaccc aagtatcaag gaagtctacc    2700
ttatctgcaa taccagcaac ctgggtgtgg tggccccttt gggctacaat ggactcctca    2760
tcatgagctg tacctactat gccttcaaga cccgcaacgt gcccgccaac ttcaacgagg    2820
ccaaatatat cgcgttcacc atgtacacca cctgtatcat ctggctagct tttgtgccca    2880
tttactttgg gagcaactac aagatcatca aacttgctt tgcagtgagt ctcagtgtaa    2940
cagtggctct ggggtgcatg ttcactccca agatgtacat cattattgcc aagcctgaga    3000
ggaatgtccg cagtgccttc accacctctg atgttgtccg catgcatgtt ggcgatggca    3060
agctgccctg ccgctccaac actttcctca acatcttccg aagaaagaag gcaggggcag    3120
ggaatgccaa gaagaggcag ccagaattct cgcccaccag ccaatgtccg tcggcacatg    3180
tgcagctttg aaaaccccca cactgcagtg aatgtttcta atggcaagtc tgtgtcatgg    3240
tctgaaccag gtgaaggaca ggtgcccaag ggacagcata tgtggcaccg cctctctgtg    3300
cacgtgaaga ccaatgagac ggcctgcaac caaacagccg tcatcaagcc cctcactaaa    3360
agttaccaag gctctggcaa gagcctgacc ttttcagata ccagcaccaa gacccttttac   3420 aacgtagagg aggaggagga tgcccagccg attcgcttta gcccgcctgg tagcccttcc    3480
atggtggtgc acaggcgcgt gccaagcgcg gcgaccactc cgcctctgcc gtcccacctg    3540
accgcagagg agaccccccct cttcctggcc gaaccagccc tccccaaggg cttgccccct    3600
cctctccagc agcagcagca accccctcca cagcagaaat cgctgatgga ccagctccag    3660
ggagtggtca gcaacttcag taccgcgatc ccggattttc acgcggtgct ggcaggcccc    3720
ggtggtcccg ggaacgggct gcggtccctg tacccgcccc cgccacctcc gcagcacctg    3780
cagatgctgc cgctgcagct gagcaccttt ggggaggagc tggtctcccc gcccgcggac    3840
gacgacgacg acagcgagag gtttaagctc ctccaggagt acgtgtatga gcacgagcgg    3900
gaagggaaca cggaagaaga cgaactggaa gaggaggagg aggacctgca ggcggccagc    3960
aaactgaccc cggatgattc gcctcgcgtg acgcctccgt cgccttttccg cgactcggtg    4020 gcctcgggca gctcggtgcc cagctccccc gtgtccgagt cggtgctctg cacccctccc    4080
aacgtatcct acgcctctgt cattctgcgg gactacaagc aaagctcttc caccctgtaa    4140
gggggaaggg tccacataga aaagcaagac aagccagaga tctcccacac ctccagagat    4200
gtgcaaacag ctgggaggaa aagcctggga gtgggggggcc tcgtcgggag gacaggagac    4260
cgctgctgct gctgccgcta ctgctgctgc tgccttaagt aggaagagag ggaaggacac    4320
caagcaaaaa atgttccagg ccaggattcg gattcttgaa ttactcgaag ccttctctgg    4380
gaagaaaggg aattctgaca aagcacaatt ccatatggta tgtaactttt atcacaaatc    4440
aaatagtgac atcacaaaca taatgtcctc ttttgcacaa ttgtgcatag atatatatat    4500
gcccacacac actgggccat gcttgccaag gaacagccca cgtggacatg ccagtcggat    4560
```

```
catgagttca cctgatggca ttcggagtga gctggtggag ccagacagag caggtgcggg    4620
gaagggaagg gcccaggcca gacccatccc aaacggatga tgggatgatg ggacagcagc    4680
tccttgctca gaagcccttc tccccgctgg gctgacagac tcctcatctt caggagactc    4740
aggaatggag cggcacaggg gtctctcttc atccactgca acccatccag tgccagcttt    4800
gagattgcac ttgaagaaag gtgcatggac cccctgctgc tctgcagatt ccctttattt    4860
aggaaaacag gaataagagc aaaattatca ccaaaaagtg cttcatcagg cgtgctacag    4920
gaggaaggag ctagaaatag aacaatccat cagcatgaga ctttgaaaaa aaaacacatg    4980
atcagcttct catgttccat attcacttat tggcgatttg gggaaaaggc cggaacaaga    5040
gattgttacg agagtggcag aaacccttt gtagattgac ttgtgtttgt gccaagcggg    5100
cttccattg accttcagtt aaagaacaaa ccatgtgaca aaattgttac cttccactta    5160
ctgtagcaaa taatacctac aagttgaact tctaagatgc gtatatgtac aatttggtgc    5220
cattatttct cctacgtatt agagaaacaa atccatcttt gaatctaatg gtgtactcat    5280
agcaactatt actggtttaa atgacaaata attctatcct attgtcactg aagtccttgt    5340
aactagcgag tgaatgtgtt cctgtgtcct tgtatatgtg cgatcgtaaa atttgtgcaa    5400
tgtaatgtca aattgactgg tcaatgtcaa cctagtagtc aatctaactg caattagaaa    5460
ttgtcttttg aatatactat atatatttt tatgttccaa taatgttttg tacatcattg    5520
tcatcaatat ctacagaagc tctttgacgg tttgaatact atggctcaag gttttcatat    5580
gcagctcgga tggacatttt tcttctaaga tggaacttat ttttcagata ttttctgatg    5640
tggagatatg ttattaatga agtggtttga aaatttgtta tattaaaagt gcacaaaaac    5700
tgagagtgaa aataaaaggt acattttata agcttgcaca cattattaac acataagatt    5760
gaacaaagca tttagattat tccaggttat atcattttt taaagatttt ccacagctac    5820
ttgagtgtct aacatacagt aacatctaac tcagctaata atttgtaaaa tctttatcaa    5880
tcacattttg ccttctttta atttttatgt tcatggactt ttattcctgt gtcttggctg    5940
tcataacttt ttatttctgc tatttgctgt tgtgtaatat ccatggacat gtaatccact    6000
tactccatct ttacaatccc tttttaccac caataaaagg attttcttg ctgttttgat    6060
ttcttctatt atttgtggaa tgaattatac ccccttaaa tatctttgtt tatgccttat    6120
gttcagtcat attttaatat gcttccttca tattgaagct gctgatttct cagccaaaaa    6180
tcatcttaga atctttaaat atccattgca tcatttgttc agaatttaac atccattcca    6240
atgttggagg cttgtattac ttatatttca tcatattcta ttgccaagtt tagtcagttc    6300
cacaccaaga atgaactgca tttcctttaa aaattatttt aaaacacctt tattgaaaag    6360
atctcatgac tgagatgtgg actttggttc catgttttca ttgtaagaaa gcagagagcg    6420
gaaaatcaat ggctccagtg attaatagat gggtttttag taattgacaa attcatgagg    6480
gaaagcatat gatctctta ttagtgaatc atgcttattt tttactctta atgccactaa    6540
tatacatccc taatatcaca gggcttgtgc attcagattt ttaaaaaatt aggatagata    6600
aggaaacaac ttatattcaa gtgtaagatg atatcaggtt ggtctaagac ttttggtgaa    6660
cacgttcatt caactgtgat cactttatta ctctgaatgc ctactattat cctgattatg    6720
gggtctcctg aataaataga gtattagtcc ttatgtcatc attgttcaaa attggagatg    6780
tacacataca tacccatatac caagagggcc gaaactcttc accttgatgt atgttctgat    6840
acaagttgtt cagcttcttg taaatgtgtt ttccttcggc ttgttactgc ctttgtcaa    6900
ataatcttga caatgctgta taataaatat tttctattt                           6939
```

<210> SEQ ID NO 4
<211> LENGTH: 829
<212> TYPE: DNA
<213> ORGANISM: Homo sapiens

<400> SEQUENCE: 4

```
cccccccgagc gccgctccgg ctgcaccgcg ctcgctccga gtttcaggct cgtgctaagc      60
tagcgccgtc gtcgtctccc ttcagtcgcc atcatgatta tctaccggga cctcatcagc     120
cacgatgaga tgttctccga catctacaag atccgggaga tcgcggacgg gttgtgcctg     180
gaggtggagg ggaagatggt cagtaggaca gaaggtaaca ttgatgactc gctcattggt     240
ggaaatgcct ccgctgaagg ccccgagggc gaaggtaccg aaagcacagt aatcactggt     300
gtcgatattg tcatgaacca tcacctgcag gaaacaagtt tcacaaaaga gcctacaag      360
aagtacatca agattacat gaatcaatc aaagggaaac ttgaagaaca gagaccagaa       420
agagtaaaac cttttatgac aggggctgca gaacaaatca gcacatcct tgctaatttc      480
aaaaactacc agttctttat tggtgaaaac atgaatccag atggcatggt tgctctattg     540
gactaccgtg aggatggtgt gaccccatat atgatttct ttaaggatgg tttagaaatg      600
gaaaaatgtt aacaaatgtg gcaattattt tggatctatc acctgtcatc ataactggct     660
tctgcttgtc atccacacaa caccaggact taagacaaat gggactgatg tcatcttgag    720
ctcttcattt atttttgactg tgatttattt ggagtggagg cattgttttt aagaaaaaca   780
tgtcatgtag gttgtctaaa aataaaatgc atttaaactc atttgagag                 829
```

<210> SEQ ID NO 5
<211> LENGTH: 3231
<212> TYPE: DNA
<213> ORGANISM: Homo sapiens

<400> SEQUENCE: 5

```
agagcccctg caccaactca ccctgtaccc tctctccttc ttcgttagtc ttctttcccc      60
cttttccctc ctctgtctgt gcctatcccc cgacttttgc atctgaccaa aggacgaatg     120
agggagacgt tcctgcagat cggggcagca actttcctca gctggtctct gggctccggg     180
agccagagag cgctgatcct ccgcggtctg cggcccatgg aagaggagga ggaggagccg     240
tgatgggcta gcgacagcac tgaggagccc cgagagagct cagccttgcc agccagctcc     300
gcggtcccac gcgggttccc tcgagctcgc tccgtgggga gcgcgcagcg tgcttggaac     360
cggagcatcc agagaggatg aggcggggac ccggcccaag ttgggtgcat ctctcgggcg     420
tccggcagcg gctgtatctc ggcatgaatt aagaagctag gaagatggag cacggcacac     480
tcctcgccca gccgggctc tggaccaggg acaccagctg gcactcctc tatttcctct       540
gctatatcct ccctcagacc gccccgcaag tactcaggat cggagggatt tttgaaacag     600
tggaaaatga gcctgttaat gttgaagaat tagctttcaa gtttgcagtc accagcatta     660
acagaaaccg aaccctgatg cctaacacca cattaaccta tgacatccag agaattaacc     720
ttttttgatag ttttgaagcc tcgcggagag catgtgacca gctggctctt ggtgtggctg     780
ctctctttgg cccttcccat agctcctccg tcagtgctgt gcagtctatt tgcaatgctc     840
tcgaagttcc acacatacag acccgctgga aacaccctc ggtggacaac aaagatttgt      900
tttacatcaa ccttttaccca gattatgcag ctatcagcag ggcgatcctg gatctggtcc    960
tctattacaa ctggaaaaca gtgacagtgg tgtatgaaga cagcacaggt ctaattcgtc   1020
tacaagagct catcaaagct ccctccagat ataatattaa aatcaaaatc cgccagctgc   1080
```

```
cctctgggaa taaagatgcc aagcctttac tcaaggagat gaagaaaggc aaggagttct    1140
atgtgatatt tgattgttca catgaaacag ccgctgaaat ccttaagcag attctgttca    1200
tgggcatgat gaccgagtac tatcactact ttttcacaac cctggactta tttgctttgg    1260
atctggaact ctataggtac agtggcgtaa acatgaccgg gtttcggctg cttaacattg    1320
acaaccctca cgtgtcatcc atcattgaga agtggtccat ggagagactg caggccccac    1380
ccaggcccga ctggccttt tggatggca tgatgacaac tgaagcggct ctgatgtacg       1440
atgctgtgta catggtggcc attgcctcgc accgggcatc ccagctgacc gtcagctccc    1500
tgcagtgcca tagacataag ccatggcgcc tcggacccag atttatgaac ctgatcaaag    1560
aggcccggtg ggatggcttg actgggcata tcaccttttaa taaaaccaat ggcttgagga    1620
aggattttga tctggacatt attagtctca aagaggaagg aactgaaaag ctgctggcg     1680
aagtgtctaa acacttgtat aaagtgtgga gaagattgg gatttggaat ccaacagtg      1740
ggcttaacat gacggacagc aacaaagaca agtccagcaa tatcactgat tcattggcca    1800
acagaacact cattgtcacc accattctgg aagaacccta tgttatgtac aggaaatctg    1860
ataagcctct atatggaaat gacagatttg aaggatattg cctagacctg ttgaaagaat    1920
tgtcaaacat cctgggtttc atttatgatg ttaaactagt tcccgatggc aaatatgggg    1980
cccagaatga caaaggggag tggaacggga tggttaaaga actcatagat cacagggctg    2040
acctggcagt ggctcctctt accatcacct acgtgcggga gaaagtcatt gacttctcca    2100
aaccccttcat gaccctaggc atcagcattc tctaccggaa gcccaatggt accaatccag    2160
gcgtttctc cttcctcaac cccctgtctc cagatatttg gatgtatgtg ctcttagcct     2220
gcttgggagt cagctgtgta ctctttgtga ttgcaaggtt tacaccctac gagtggtata    2280
accccaccc atgcaaccct gactcagacg tggtggaaaa caatttttact ttactaaata    2340
gttttctggtt tggagttgga gctctcatgc agcaaggatc agagctgatg cccaaagctc    2400
tatcgaccag aatagttgga gggatatggt ggttttttcac cctaatcatc atttcatcct    2460
acacggccaa tctggctgcc ttcttgacag tagagagaat ggaatccccc atagattcgg    2520
cagatgatct ggcaaagcaa accaagatag aatatggggc ggttagagat ggatcaacaa    2580
tgaccttctt caagaaatca aaaatctcca cctatgagaa gatgtgggct ttcatgagca    2640
gcaggcagca gaccgccctg gtaagaaaca gtgatgaggg gatccagaga gtgctcacca    2700
cagactacgc gctgctgatg gagtccacca gcattgagta tgtgacgcag agaaactgca    2760
acctcactca gatcggggc ctcattgact ccaaaggtta cggagtggga acacctattg      2820
gttctcctta ccgggataaa attactattg ctattcttca actccaagaa gaagggaagc    2880
tgcatatgat gaaagagaag tggtggcgtg ggaatggctg ccccgaggaa gacaacaaag    2940
aagccagtgc cctgggagtg gaaaatattg gaggcatctt cattgttctg gctgccggac    3000
tggtcctttc tgtatttgta gctattggag aattcatata caaatcacgg aagaataatg    3060
atattgaaca ggcttttttgt ttcttttatg gactgcaatg taagcaaaacc catccaacca    3120
actccacttc tggaactact ttatctacgg atttagaatg tggtaaatta attcgagagg    3180
agagagggat tcgaaaacag tcctcagttc atactgtgta atcagtttaa a             3231
```

<210> SEQ ID NO 6
<211> LENGTH: 9093
<212> TYPE: DNA
<213> ORGANISM: Homo sapiens

```
<400> SEQUENCE: 6
tgaggcctga ggcctggggc ggggtggcgg ccgggctggc cttggcctcg cgccttcccc      60
tgcggccgcc gcgggctccg cgggcggtat cggagtgtcg tgcggcgcgt ggccgcgtga     120
cacgcgcact tgtcggagtg acgggccctg cggaagagga ggtgcggccc agggcgcagg     180
ggagccctcg ggagcgggcc cggccctcag cgccgccccg gccgtgtccc ggaggagcgg     240
cctgcgccgc cgcgcgagag gaagcaccca ggcatgtgga atatgctcat agtggcgatg     300
tgcttggccc ttctgggctg cctgcaagcc caggagctcc agggacatgt ctccataatc     360
ctgctgggag caactgggga cctggctaag aagtacttat ggcagggact gttccagctg     420
tacctggatg aagcggggag gggtcacagt tttagcttcc atggagctgc tctgacagcc     480
ccaagcaggg tcaagagctc atggccaagg ccctggaatc cctctcctgc ccaaggact     540 ggcacccagt cactgtgcag agcacaagga tcagttcctg cagctgagcc agtaccgcaa     600
ctgaagacgg ccgaggacta tcaggccctg aacaaggaca tcgaggcaca gctccagacg     660
caggcctccg ggaggctggc aggatcttct acttctcagt gccacccttc gcctataaga     720
cattgcccgc aacatcaaca gtagctgccg gccaggcccg ggcgcctggc tgcggttgtc     780
cttgagaaac cctttggcca tgaccacttc tcagcccagc agctggccac agaatcggga     840 ccttttcca ggaggaggag atgtaccggg tggaccatta cttaggcaag cagctgtggc     900
gcagatcctg cctttccgag accagaaccg caaggctttg acggcctct ggaccggcac     960 catgtggagc gggtggagat catcatgaaa gagaccgtgg atgctgaagg cgcaccagct    1020
tctatgagga gtacggtgtc attcgcgacg tcctccagaa ccatctgacg aggtcctcac    1080
cctcgtggcc atggagctgc cccacaatgt cagcagtgcg gaggctgtgc tgcggcacaa    1140
gcttcaggtc ttccaggcgc tgcggggcct gcagaggggc agtgccgtct gggccagtac    1200
cagtcttaca gtgagcaggt gcgcagagag ctgcagaagc cagacagctc cacagcctga    1260
cgccgacctt cgcagccgtc ctagtgcaca ttgacaacct tcgctggagg gcgtgccttt    1320
catcctgatg tctggcaaag ccttggacga gagagtgggc tacgctggat cttgttcaag    1380
aaccaggcct gctgtgtgca gagcgaaaag cactgggccg cggcgagagc cagtgcctgc    1440
cccggcagct cgtcttccac atcggccatg gcgacctggg cagcctgccg tgctggtcag    1500
caggaacctg ttcaggccct ccctgccctc cagctggaag gaatggaggg accacctggg    1560
ctccgccttt tcggcagccc tctgtccgat tactacgcct acgccctgtg cgggagcggg    1620
acgcccactc cgtcctctta tcccatatct tccatggccg gagaatttct tcatcaccac    1680
agagaacttg ctggcctcct ggaacttctg gaccctctg tggagagcct ggcccataag    1740
gccccacgcc tctaccctgg aggagctgag aatggccgtc tgttggactt tgagttcagt    1800
agcggccggt tgttctttc ccagcagcag ccggagcagc tggtgccagg gccagggccg    1860
gccccaatgc ccagtgactt ccaggtcctc agggccaagt accgagagag cccgctggtc    1920
tccgcctggt ccgaggagct gatctctaag ctggctaatg acatcgaggc caccgctgtg    1980
cgagccgtgc ggcgctttgg ccagttccac ctggcactgt cgggggctc gagcccgtg     2040 gccctgttcc agcagctggc cacggcgcac tatggcttcc cctgggccca cacgcacctg    2100
tggctggttg acgagcgctg cgtcccactc tcagacccgg agtccaactt ccagggcctg    2160
caggcccacc tgctgcagca cgtccggatc ccctactaca acatccaccc catgcctgtg    2220
cacctgcagc agcggctctg cgccgaggag gaccagggcg cccagatcta tgccaggag    2280 atctcagccc tggtggccaa cagcagcttc gacctggtgc tgctgggcat gggtgccgac    2340
```

| | | | | |
|---|---|---|---|---|
| gggcacacag | cctccctctt | cccacagtca | cccactggcc | tggatggcga gcagctggtc | 2400 |
| gtgctgacca | cgagcccctc | ccagccacac | cgccgcatga | gccttagcct gcctctcatc | 2460 |
| aaccgcgcca | agaaggtggc | agtcctggtc | atgggcagga | tgaagcgtga gatcaccacg | 2520 |
| ctggtgagcc | gggtgggcca | tgagcccaag | aagtggccca | tctcgggtgt cctgccgcac | 2580 |
| tccggccagc | tggtgtggta | catggactac | gacgccttcc | tgggatgagg gcgcctgtgc | 2640 |
| cccttgcccg | cttcgctcct | gtgctttcct | tcgcccgtgt | cttccctccc ttctcggccc | 2700 |
| cgccacctgc | ccagcgtgcc | ctggctctcc | agaaccttct | atcccacagt caggcccag | 2760 |
| agagggcagg | acaagccttg | tcccgatgcc | tttgaccggc | agctctgtgt attggtggat | 2820 |
| agatgcagaa | acaaggaaga | aatggagtct | gctcctgaga | agcttcaaat tcaggccagg | 2880 |
| agagaagtct | taagaaaaga | cctccagcag | ttacacattc | atatcaacca gcacaacacg | 2940 |
| ggatggcgcc | caaactccgg | cgttcacaag | aggagacgtg | acgtggtggg ctgaggttaa | 3000 |
| tcagggaagg | tttcctgggg | gaggtgatcc | ttgaactggc | tcccggggaa cattcagagc | 3060 |
| atgattggta | gacagaaggg | tgcagaggcg | cccaggggag | tacattgccc cgtgcaaagc | 3120 |
| agggcattg | gggactgtct | tgagaccctg | aggggtcaa | gcccctcctt ccccagctgc | 3180 |
| ccctccttct | agaacctctg | cacatctagc | ctctggccct | cctcttcact gcctccacct | 3240 |
| gctcccgctt | gccatccctg | tctcctccat | cctggctgtg | cagtaggaat tccaggctcc | 3300 |
| tccctgtgtc | tttgctgttc | ttcagactcc | atttatagag | aatgagggct gataacagga | 3360 |
| atacagtggc | aaagactaga | ctgtggaaag | ggttccagaa | atctttttc ttttttaatt | 3420 |
| aaaaaaaata | tttgcagaga | tgagctcttg | ctatgttgcc | caggctggtc tcaaactcct | 3480 |
| gggctcaagc | gatcctccca | tctcagcctc | ccagagtgct | gggattacag gtgtgagcta | 3540 |
| ctgcgcccag | ccccagaaat | ctcagtgctg | tttggagctc | catttctcat ttgatgactt | 3600 |
| gctctgcgtg | gggaggtggg | gtctcattcc | cccaacttcc | tcagggagga ccctgccct | 3660 |
| ccgctgctcc | tctgtcctgc | tagccttcct | ccaggaagca | cactgggtgc agataatcag | 3720 |
| gacattccag | agatccccaa | tttaagaggg | tcatttccat | ctcaggggac tcccggatgg | 3780 |
| gtgtttccgc | tctcaatagc | ccctcttgtt | ttaccaggaa | agatccagtt aaatcaccca | 3840 |
| ctgaggtgac | agctcattag | cggggagaga | gatggagcat | cgagtgacac tgggccatcc | 3900 |
| aggcggctct | gctcccacca | gacaggagct | aggcctcact | ggcagggggg ctgcccacag | 3960 |
| ccttttcagg | ggctcgcttg | gcgggtgacg | gggccgcagc | caggccttct ctccctgccc | 4020 |
| cttggtgacc | ccgtggcttc | ctgtctgctg | gcctctcctg | ctacttatca cttcaccacg | 4080 |
| aactctctgc | ctgagactgg | ggaagtaagc | gggtatcttc | tcagtgagca taggttgggg | 4140 |
| actgtgatct | tgagaagcca | tgggccagca | atacctgctt | ttctgaagcc cccaaggagg | 4200 |
| gctctgacat | tctttttaaa | aacaccacaa | agcaaaattc | ccaggacatg tgtagttttg | 4260 |
| tttgttcagt | atcccacaac | ttaaggctgg | gagatggaac | tcttggttaa ggtcgatttt | 4320 |
| tctgtctggc | ttctccgcac | cttccacttg | ctctctggat | caggcagata taaactttct | 4380 |
| agcgcatttt | gagagagggc | tttcttgggt | gagggagcat | ggcaaagtcg gtttctctct | 4440 |
| ggactgttta | cacttcaagg | cggtggattt | agaggaatcc | tggctttcat tttcaatgcc | 4500 |
| agtctgagac | atgttcccaa | gccggggctc | ttgttcacac | cacttactct ggccaccaac | 4560 |
| aacaacccag | gccagacaga | gcatctcttt | tttttttttt | tgagacagag tctctgtcgc | 4620 |
| ccaggctgga | gcccagtggc | gagatcttgg | ctcactacaa | cctccacctc ccgggttcag | 4680 |
| gcaattctcg | tgcctaagcc | tcccgagtag | ctgcgactac | aggcgccggc cagcatgcct | 4740 |

```
gtctaattttt tgtattttag tagagacagg gtttcaccat gttgcccagg ctggtctcga   4800
actcctgagc tcaggcagtc tacccacctc agcctcccaa agtgctggga ttacaggcgt   4860
gagccaccgc gcccagccag aacatctgtt tttacaccca gagagcgccc ctcgttagga   4920
cagaaccacg gtgcccagag ccaggaagcc gccctcctgg cgcccagcat ctgagcttct   4980
acacgtgatg ggcgggctca ggagaggaca gggagtcgtg gtggaagttc cacagctggc   5040
cgcgtggggg ggcccttgca ccgcactgcc gcctcctgac tgcccctatc cccgcagccc   5100
ctgtgccgga tttcatttcc ctcctctctc ccagggtacc tggccccagc actctcccat   5160
ctgttcttca ggaaccgact cctctccagt tgcaacacca gggagaaagg ggcctccaca   5220
tgcccaagta cccctgcagg atgaagggca ggccggccct tgatgtgcca tttctgaata   5280
atagtcactg ccgccgagtc taggatgtcc tgttctaact cagccctgcc tcggatgcac   5340
caccgatctg tgcagagtgg gtgtgggagt gtgggtgagg gtcgaaatgc caaaggtcta   5400 cttttccagaa tcaagtgcct tctgcaaatc atgttggaaa agtccaaacc tggagatgtc   5460
cctgtgcctc cgcccctacc caccccttt ccttcagctg tgttaggaag agaagttt   5520 cagaaccctc taggctggtg gctttcaaac ttcagaccag atctgcagca agaaacgtgc   5580
cttccatcat aaatcagtcc atttgtttac aactgtgtcc aagcaggttt cataaagaaa   5640
ttcttaacct tagaacctcg gatatcctct atgttttagt tttcattttt ttaaaatgct   5700
tcttaaaatt cactaaattg ggctaggtgt ggctcatgcc tgtaatccca gcactatggg   5760
aggctgaggt gagaggatca cttgagccca aaggttgaa accagcctgg caacatagt   5820 gagacccat ctctacaaaa agttttaaaa ccaggtatgg tggtgccctc ctgtggtccc   5880
agctactcgg gagtctgagg tgggaggatc acctgagccc aggagactga ggctgcagta   5940
aggtgtgatt gcactattgc tctctagcct ggaaaacaga gtgagaccct atctcaaaaa   6000
aaaaaaaaaa aaaaaggaa agagtgatga caacagccca gggagcagcc ccgctcagaa   6060
cccaagtccc aagttccagc actgtgttcc caggcaggct gttgcctct tcctggtctg   6120 gaagcccttg ggtcctatgg tggcggcagc tcccacatcc aggttccctg gtggggacca   6180
atgattccat ccgcatggaa gcccacgtgt gcacttaggg gcccataaat ggcagaaggg   6240
cccctccttt gggagacctt gtcagtcagc atctctaggg caaccgtgat tgccatttgt   6300
agaggggaag gaatcaaggg actttaagct agatcaaaat ctggggacaa attctcctgc   6360
taactgcaag ttaaaatagg ccccttcttac tgaatttccc tgtttgtttc tctgcagaca   6420
atgctttagc cctactcttg ggcccccaag ttagcagagt aatcaaagct tcctaccgtt   6480
tggcctacta ttccagacta gtccctcgag gggttcccctt ccaaaatatg cagggctcag   6540
gctcccaatt ccgggcctgt ctgctttgct tgtgtttctc ctgtccctgt tctcccggag   6600
ggcccaggtg gaactcacga cagggaggga gacgcttccc aaaaacctgc agggctattt   6660
cccagaattt ggttttcaag tacaaaactt tttgtcctgt aagatatatg cagcctcaca   6720
gaagcagcct ctgcctccac tttaccagct acgttttat cttaagcaca tggggctccc   6780
ttagaactta ctccactgat ttaaaaaaaa aaaactgcct ggcagcatct cagtgtcaga   6840
gtgagcacgg cacaggaaag gcccgtggtg acgagggtga ggtggccaca gtgaccggac   6900
gacaaatgag actctgcaaa tgagactcca gagggtgaag atctgcggtc tccagacatc   6960
ataggccatg tgacccacta ggggccgctt acccctggcc gtccgctggc tgaactgaac   7020
gcattccctc tctccgcaac tctcccgtga ggctgcaccc gtgtgggtag cactggaagc   7080
ggcactgttt gcattgtaca taggaaggaa ggaagttctt ccagcctcac cagcacctgg   7140
```

| | | |
|---|---|---|
| cagcgagtca gagcctgtga gggcatccga agcagtgatg cagtgtcaac ctcccagctg | 7200 | |
| gtgccactct gccctcgggg gctccaagca ttgtaactca gtcatgggag ctgcctcttt | 7260 | |
| ggaagtgcag atttattcct gtaataatcc tgcctgcttt tacctctcgt ccactgacca | 7320 | |
| gcaagtgtga gtcccggtgt cagtcggcac agtccagtgt ccatctgcat ttgctcatgc | 7380 | |
| agaggggtg agttgggcac tccctgttgt tggttttcct tttgcagcac actgggcagt | 7440 | |
| ctccctataa aacaaaaacc ccaccttctg tgccttctgc tttagagcag agctccccct | 7500 | |
| cccatttcct cagtcttccc tgcaaaatct gtccaccggg gaaggcagca ggaaccctgg | 7560 | |
| gcagcgggtg ttctgggaag gctagtgaca gcagatgtca tccaggaaca gccacacacg | 7620 | |
| gttctccagg ccgccgtcag cagctcaagg tggggtatga gtgagaagct gaggatctcg | 7680 | |
| cagcttgttg ctgagcaagg tgcaaccggg ctcatgctgt catcagcaca agacgggatg | 7740 | |
| gcaagggctt tcagacgcat ttccaagagt ccagcaagcc agggggaaga tgatcccttt | 7800 | |
| gccgaagtgt accctctagc caacttttgg gagcgcttct gtttgcaaag cgctggggat | 7860 | |
| gtgcctgtct ctgtgtgacc cacgaacggg aagggagagc actggagtaa tgacacttct | 7920 | |
| gctgctgctt tgattctcaa ggctgatctt taaaaccctc gccttgctga caggtgcttt | 7980 | |
| aaaggcagtc tgcatctttt cttcccttgg tgtgggagag gtaaacactt tgatttgctg | 8040 | |
| aaagctgtat ggagtatatt tgaacagcta gtagttagct ttgaaagtgg aagtgtgaac | 8100 | |
| agacactact tgtgtcgctt tgggtccttc actttacccc cacagaagtc tagaggcgtc | 8160 | |
| tgttataaag cgttacgggg cgcctgcatg caggaggaag gacctgtatt agctggaaat | 8220 | |
| catcaggaac ccagcttgcc tccatctctc tgagatgtgc tgggtacagc ctgcccctcc | 8280 | |
| tagttctgtc caccgggaag agccggctgg cggcagatcc ccaggggcag agcccctgct | 8340 | |
| ggatcctggg agctcatctt tacctgtgcc ggagtgggaa ctgtgattcc agccgggcag | 8400 | |
| gtcagagtgg agcagtgcta agaggctgtt gcaggagaac tagacgggcg gggcctgctg | 8460 | |
| catctggatc atgtttctgt gctctgcccc gcgctaggga ctcagggtct gggcttctgc | 8520 | |
| caggtgagga gcagagagac tgttcccttg ggtggagagg tgtgggcatg agagccaccc | 8580 | |
| attgccaagc agcaagaatg ttcgtgcttt tttccagaga ggggaacccc actggttttt | 8640 | |
| gtggaaacaa tggaaactta cagatgcctg cctgggatga tgaggcacat tcagaacaaa | 8700 | |
| tgcttttttt ttttgagac agagtctcgc tctgacgccc aggctggagt gcagtggcgc | 8760 | |
| gatctcggct cactgcaaac tttgcctccc aggttcaagt gattctccta cctcagcctc | 8820 | |
| ccgagtagct gggattacac caccatgccc agcaaatttt tgtgttttta gtagagacgg | 8880 | |
| agtttcacca tgttggccag gctggtctcg aactcctgac ctcaggtgat ccatccgcct | 8940 | |
| tggcctccca aagtgctggg attacaggcg ggagccacca tgcctggcca gaacaaatgc | 9000 | |
| cttttaaac cttttaagaa cattttaaa atgtcttttt ctatgtcaaa tgtaacgttt | 9060 | |
| atttttttaa acaataaaat tgatttgcca aaa | 9093 | |

<210> SEQ ID NO 7
<211> LENGTH: 8347
<212> TYPE: DNA
<213> ORGANISM: Homo sapiens

<400> SEQUENCE: 7

| | | |
|---|---|---|
| atttagaggc ggcgccaggg cggccgcgga gaaacgtgac acaccagccc tctcggaggg | 60 | |
| gtttcggacc gaagggaaga agctgcgccg tgtcgtccgt ctccctgcgc gccgcgggca | 120 | |
| cttctcctgg gctctccccg aactctcccg cgacctctgc gcgccctcag gccgccttcc | 180 | |

```
ccgccctggg ctcgggacaa cttctggggt ggggtgcaaa gaaagtttgc ggctcctgcc      240
gccggcctct ccgcctcttg gcctaggagg ctcgccgccc gcgcccgctc gttcggcctt      300
gcccgggacc gcgtcctgcc ccgagaccgc caccatgaac aagctttaca tcggcaacct      360
caacgagagc gtgaccccccg cggacttgga gaaagtgttt gcggagcaca agatctccta      420
cagcggccag ttcttggtca atccggcta cgccttcgtg gactgccgg acgagcactg       480 ggcgatgaag gccatcgaaa cttcctccgg gaaagtagaa ttacaaggaa aacgcttaga      540
gattgaacat tcggtgccca aaaaacaaag gagccggaaa attcaaatcc gaaatattcc      600
accccagctc cgatgggaag tactggacag cctgctggct cagtatggta cagtagagaa      660
ctgtgagcaa gtgaacaccg agagtgagac ggcagtggtg aatgtcacct attccaaccg      720
ggagcagacc aggcaggctg acgaggttcc cctgaagatc ctggcccata taactttgt       780 agggcgtctc attggcaagg aaggacgaa cctgaagaag gtagagcaag ataccgagac       840
aaaaatcacc atctcctcgt tgcaagacct tacccttttac aaccctgaga ggaccatcac      900
tgtgaagggg gccatcgaga attgttcag ggccgagcag gaaataatga agaaagttcg       960
ggaggcctat gagaatgatg tggctgccat gagcctgcag tctcacctga tccctgggcct     1020 gaacctggct gctgtaggtc ttttcccagc ttcatccagc gcagtccgc cgcctcccag       1080 cagcgttact ggggctgctc cctatagctc ctttatgcag gctcccgagc aggagatggt      1140
gcaggtgttt atccccgccc aggcagtggg cgccatcatc ggcaagaagg ggcagcacat      1200
caaacagctc tcccggtttg ccagcgcctc catcaagatt gcaccacccg aaacacctga      1260
ctccaaagtt cgtatggtta tcatcactgg accgccagag gcccaattca aggctcaggg      1320
aagaatctat ggcaaactca aggaggagaa cttctttggt cccaaggagg aagtgaagct      1380
ggagacccac atacgtgtgc cagcatcagc agctggccgg gtcattggca aaggtggaaa      1440
aacggtgaac gagttgcaga atttgacggc agctgaggtg gtagtaccaa gagaccagac      1500
ccctgatgag aacgaccagg tcatcgtgaa aatcatcgga catttctatg ccagtcagat      1560
ggctcaacgg aagatccgag acatcctggc ccaggttaag cagcagcatc agaagggaca     1620
gagtaaccag gcccaggcac ggaggaagtg accagcccct ccctgtccct tcgagtccag     1680
gacaacaacg ggcagaaatc gagagtgtgc tctccccggc aggcctgaga atgagtggga     1740
atccgggaca cctgggccgg gctgtagatc aggtttgccc acttgattga gaaagatgtt      1800
ccagtgagga accctgatct ctcagcccca acacccacc caattggccc aacactgtct       1860 gccccctcggg gtgtcagaaa ttctagcgca aggcactttt aaacgtggat tgtttaaaga     1920
agctctccag gccccaccaa gagggtggat cacacctcag tgggaagaaa aataaaattt      1980
ccttcaggtt ttaaaaacat gcagagaggt gttttaatca gccttaaagg atggttcatt      2040
tcttgacctt aatgtttttc caatcttctt ccccctactt gggtaattga ttaaaatacc      2100
tccatttacg gcctctttct atatttacac taattttttt atctttattg ctaccagaaa      2160
aaaatgcgaa cgaatgcatt gctttgctta cagtattgac tcaagggaaa agaactgtca      2220
gtatctgtag attaattcca atcactccct aaccaatagg tacaatacgg aatgaagaag      2280 agggaaaat ggggagaaag atggttaaaa tacataataa tccacgttta aaaggagcgc       2340
acttgtggct gatctatgcc agatcaccat cttcaaattg gcacaactga aatttcccca     2400
ctctgttggg gcttccccac cacattcatg tccctctccc gtgtaggttt cacattatgt      2460 ccaggtcac ataggtggta ttgaatgctc agcagggtag gggctgacca ctgtccctga       2520
ttcccatcgt tctcaggcgg atttatatt tttttaaagt ctatttaat gattggatat        2580
```

```
gagcactggg aagggacgc taactcccct tgataaagtc tcggttccat ggaggacttg    2640
agtggcccca aaggctgcca cggtgccctc acccagccc atgtgctccc ataagggctg    2700
gttcctagag gcaggggttg tgggcactc ccagccacgg cactgttacc ttggtggtgg    2760
gacttggaac ccaaccctga gctcccgata aagctaaagt ccatcatctg gcaaattcag    2820
taaattggag agtacttgct tctgtttgta tctgagagga atttttaact gacggcttct    2880
gtctccatga atcattatca gcatgatgaa aggtgtgtct aaaaaacaat tcagaatacc    2940
agcagcattg tacagcaagg ggtaaataag cttaatttat taatttacca ggcttaatta    3000
agatcccatg gagtgtttag cccttgtggg agacagaagc catcagttaa atgaggttag    3060
gcctctcctc ctaatatact gattgacaat gcatattagc caggtaatgc actttagcta    3120
ccctggacaa tgctatcaag tgtgctggga agggaggaag gcctctctac atatggaaaa    3180
gcccatgcgt ggagttcccc tccttcaac attgcaacaa cagtaacaac aagacaaccg    3240
caacatgtgg gcgtagtcag gcaatgctgt gtgcgaagta aactacctca aggtatgaag    3300
ttacctcagc aattattttc cttttgttc ccccaaccc cattaaaaaa attttttttt    3360
gatttttgtt tttttgcagc ttgctgatat tttatataaa aagaaaagc aaagcaaaag    3420 agaagctgat agtcttgaat atttttatttt tttaatgaaa agaaaaaaca agaaagttat    3480
gtttcataat ttcttacaac atgagccagt aacctttag gaactctcta tggagaacag    3540
gcctggtggg aaaggctttg ggggctgccc ccttaggagg aggctagtgc taagagggaa    3600
ggcccaggtt tgagagagcc cagaggggca gagcccagag ccttgtttgg ccctgatctc    3660
tgacttctag agccccagct gctggcggct gctggaatat cctacctgat aggattaaaa    3720
ggcctagtgg agctgggggc tctcagtggt taaacaatgc ccaacaacca accagctggc    3780
cttggtctcc tctcttcct cctttggtta aagagcatct cagccagctt tcccaccag    3840 tggtgctgtt gagatatttt aaaatattgc ctccgtttta tcgaggagag aaataataac    3900
taaaaaatat accctttaaa aaacctata tttctctgtc taaaaatatg ggagctgaga    3960
ttccgttcgt ggaaaaaaga caaggccacc ctctcgccct cagagaggtc cacctggttt    4020
gtcattgcaa tgctttcat tttttttttt tgttattgtt tcatttcagt tccgtcttgt    4080
attcttccta atctatatcc atagatctaa ggggcaaaca gatactagtt aactgcccca    4140
cctctgtctc cctgtcttct ttagatcggt ctgattgatt ttaaaagtgg acccaaatta    4200
gggaattctt gatttagggt ggctggtggc aaggaggggc aggggatatg gggacgtgac    4260
tgggacaggt tcctgcctta tcatttctc cctaggacat tcccttgtag cccccagaat    4320
tgtctggccc aaattgaata gaagcagaaa acatttagg gataacatca ggccagtaga    4380
attaagcctc tccacctgtc ccaaccataa aaagggtctc ccagctttcc atctctggct    4440
ctatatgctt tatcccaaaa caaagcagat aacgttcaga cgtcggccat ttagtaattt    4500
aaagcgaatt ccagcagca agcatgcttt gatatctggt tcagactatc atcaggaaga    4560
aaaaaaaatc ccacagtacc tgaaatgtga ttgttgcagt gttcagtttc cttggggcc    4620 tgctcccttc acaccttgag cccaagtcct tttccgttgg ctgattcagc tcccagaaga    4680
gacgaggaag tgtgtggcaa gggactggaa aacttcactt gcttggatta ggcaaggctc    4740
cactcattgt tgatatttgc ccagcaggaa aatcatgtaa gttataccac cagaaagcaa    4800
aaggagcatg gtttggtggt taaggtttag tgggatgaag gacctgtctt ggtgggccgg    4860
gccctcttgt gccccgtagg ctaggtctta gggcaactcc ttgccctcct gctcagcacc    4920
tccatttccc catccttggt gagataacaa gctatcgcga aaagcacttg ggagatttgg    4980
```

```
atgatttgag aagagtgact taaaaaaaat gcttctgtgc tctaagatat atatgtgtgt    5040
gtgtgtgcta catatatatt tttaagaaag gaccatctct ttaggatata tttttaaatt    5100
ctttgaaaca cataaccaaa atggtttgat tcactgactg actttgaagc tgcatctgcc    5160
agttacaccc caaatggctt taatcccctc tcgggtctgg ttgccttttg cagtttgggt    5220
tgtggactca gctcctgtga ggggtctggt taggagagag ccattttaa ggacagggag     5280
tttttatagcc cttttctact ttcctcccct cctcccagtc cttatcaatc ttttttcctt   5340
tttcctgacc ccctccttct ggaggcagtt gggagctatc cttgtttatg cctcactatt    5400
ggcagaaaag accccattta aacccagag aacactggag ggggatgctc tagttggttc     5460
tgtgtccatt ttcctctgtg ccaaagacag acagacagag gctgagagag gctgttcctg    5520
aatcaaagca atagccagct ttcgacacat acctggctgt ctgaggagga aggcctcctg    5580
gaaactggga gctaagggcg aggcccttcc cttcagaggc tcctggggga ttagggtgtg    5640
gtgtttgcca agccaagggg tagggagccg agaaattggt ctgtcggctc ctggttgcac    5700
tttggggaag gagaggaagt ttggggctcc aggtagctcc ctgttgtggg actgctctgt    5760
cccctgcccc tactcagag atagcactgc cgagttccct tcaggcctgg cagacgggca     5820
gtgaggaggg gcctcagtta gctctcaagg gtgccttccc ctcctcccaa cccagacata    5880
ccctctgcca aactgggaac cagcagtgct agtaactacc tcacagagcc ccagagggcc    5940
tgcttgagcc ttcttgctcc acaggagaag ctggtgcctc taggcaaccc cttcctccca    6000
cctctcatca ggggtggggg ttctccttc tttcccctga agtgtttatg gggagatcct     6060
agtggctttg ccattcaaac cactcgactg tttgcctgtt tcttgaaaac cagtagaagg    6120
gaaacagcac agcctgtcac agtaattgca ggaagattga agaaaaatcc tcatcaatgc    6180
caggggacat aaaagccatt tcccttccaa atactcgaca atttagatgc agaacatttc    6240
tctgtattca gacttagagt aacaccagct gaaaactgca gtttctttcc tttggataca    6300
taaggcttct ctatcggggt acgggacagg gaggaggcct catgtctgaa ggggattag    6360
gggcgagagc cccagccctg accctcggtc ctgtgcaccg ctttggggca cagtctgatg    6420
gcgccttttgc tggcgcctta gtatggttga ctccggatgg acaaaagaaa aaaattttt    6480
tttcttgaat gaaatagcag gaagctcctc gggagcatgt gttttgatta accgcaggtg    6540
atggatgcta cgagtataaa tggattaact acctcaatcc ttacagtaag attgaaacta    6600
agggcaggga ctcatgcata agggtatgaa tcccagccag gacaagtgag ttgaggcttg    6660
tgccacaaaa ggtttgtcct tggggaacag gcaggcctgc caggatcccc cccatatcga    6720
ttgggctggg agggctggcc atgaggtccc cactttctgc tttccttgcc catgtgtcac    6780
cccttttggcc tccagcttgt ccctctctca ctttctatag ctttgttgga ccagatggtg    6840
aggaaaggaa tggcctcttc ccttctagag ggggctggct ggagtgagac ctggggcttg    6900
gcctggaacc caccacacag ccccaaagtc aggaagcctg gggaaaccag agctgagacc    6960
tcttcaacag ggtttctttg agatcctaca cctccattgg gccctttttc agtcttcaat    7020
gggggcccag ttggctctag aaggagaaga ggtgaagcag gatcctttgc cctgggggag    7080
tctgagggcg cggtccttgg actcattcag gccgtctttg tagttggggg agttccactg    7140
ggcgatccca gccctcccc acccaccctc taatggacct cctcatagaa gccccatttc     7200
acttttgttt tatctacctc ttagcaaaac aatagataaa ttaggtagtg gcagctccac    7260
ttgcttaggt taggggggga aaagatttc ttttccaaa ggaaaaaaat attaccttga      7320
gaatactttc caaaaaataa aattaaaaaa aaaaaaacca aaaaaaaaa tttttttta     7380
```

```
aaagggagac attttccagt gaccactgga ttgttttaat ttcccaagct ttttttttccc    7440 ccataaataa gtttcactct ttggcgattt tcttcacttg tttaagataa cgtgctagct    7500
attccaacag gtaacagctt tcacagtctg ccctggcct gtctcacccc atccccacc     7560 ctattcctgc cagtgagtcc ttcctgtgct tctctccctt ctcccctccc agccagctga    7620
cttcagtcac ccctgtcccc cctccctgc caataagctc cccaggaat aaaggctttg     7680 ttttggggat gcttaaatct tgactggcac ttcccggctg tgggggctgg ggagccactt    7740
gtaacatttc tgtgcagatt ttatgttagc cactgctatg taaaagcacg ttcaaaatga    7800
atttcagcag attatgtgtt accataatga ataaacgtcc tctatcacca tttggagtct    7860
cccttttctc caggatcttg atcctggtcc ccaaaaccag agtgaatcaa aagagcttcc    7920 tccccctgagg caaagtggat tgtaagcag ttctgaaaca tcacttactc agaagaggga    7980
acgatgtatt ttgatgagtg caaattggga agagctggag gcctactgct tgggacagtt    8040
tttttttttt tttttttttt aaatatgagt gctagcttat tctgtaattg cggcaacttt    8100
gaaaattgta ttttactgga aatctgccag ccatcaccac ccgattttga ttgtatcctt    8160
cctcccatcc tttaatctgt tcattgcttt gggggaggtg gggcagctgg ctcacacgtt    8220
ggagtttgtt ctttgatgga tgaacgaaca ctccagttt ctttcccgtg aaggttgttt     8280
cagccacaaa ccacttcatt ttgctgtttc aattttcaaaa taaaggaaaa cttatattga    8340
aagacaa                                                             8347

<210> SEQ ID NO 8
<211> LENGTH: 10072
<212> TYPE: DNA
<213> ORGANISM: Homo sapiens

<400> SEQUENCE: 8
gggaggccgg aagttgcggc ttcattactc gccatttcaa aatgctgccg aggccctagg      60
atctgtgact gccaccccte ccccacccg ggctcggcgg gggagcgact catggagctg     120
ccgtaagttt taccaacaga ctgcagtttc ttcactacca aaatgacatc attttccacc    180
tctgctcagt gttcaacatc tgacagtgct tgcaggatcc ctcctggaca aatcaatcag    240
gtacgaccaa aactgccgct tttgaagatt ttgcatgcag caggtgcgca aggtgaaatg    300
ttcactgtta aagaggtcat gcactattta ggtcagtaca taatggtgaa gcaactttat    360
gatcagcagg agcagcatat ggtatattgt ggtggagatc ttttgggaga actactggga    420
cgtcagagct tctccgtgaa agacccaagc cctctctatg atatgctaag aaagaatctt    480
gtcactttag ccactgctac tacagatgct gctcagactc tcgctctcgc acaggatcac    540
agtatggata ttccaagtca agaccaactg aagcaaagtg cagaggaaag ttccacttcc    600
agaaaaagaa ctacagaaga cgatatcccc acactgccta cctcagagca taaatgcata    660
cattctagag aagatgaaga cttaattgaa aatttagccc aagatgaaac atctaggctg    720
gaccttggat tgaggagtg ggatgtagct ggcctgcctt ggtggttttt aggaaacttg      780
agaagcaact atacacctag aagtaatggc tcaactgatt tacagacaaa tcaggatgtg    840
ggtactgcca ttgtttcaga tactacagat gacttgtggt ttttgaatga gtcagtatca    900
gagcagttag gtgttggaat aaaagttgaa gctgctgata ctgaacaaac aagtgaagaa    960
gtagggaaag taagtgacaa aaaggtgatt gaagtgggaa aaaatgatga cctggaggac    1020
tctaagtcct taagtgatga taccgatgta gaggttacct ctgaggatga gtggcagtgt    1080
actgaatgca agaaatttaa ctctccaagc aagaggtact gttttcgttg ttgggccttg    1140
```

```
aggaaggatt ggtattcaga ttgttcaaag ttaacccatt ctctctccac gtctgatatc   1200
actgccatac ctgaaaagga aaatgaagga aatgatgtcc ctgattgtcg aagaaccatt   1260
tcggctcctg tcgttagacc taaagatgcg tatataaaga aagaaaactc caaactttt    1320 gatccctgca actcagtgga attcttggat ttggctcaca gttctgaaag ccaagagacc   1380
atctcaagca tgggagaaca gttagataac ctttctgaac agagaacaga tacagaaaac   1440
atggaggatt gccagaatct cttgaagcca tgtagcttat gtgagaaaag accacgagac   1500
gggaacatta ttcatggaag gacgggccat cttgtcactt gttttcactg tgccagaaga   1560
ctaaagaagg ctggggcttc atgccctatt tgcaagaaag agattcagct ggttattaag   1620 gttttttatag cataatggta gtacgaacat aaaaatgcat ttattccgtt cacttaccac   1680
attatttgaa aatcaatcct ttatttaatt ttatttccaa cctgtcagag aatgttctta   1740
ggcatcaaaa tccaaggtag ctgtaagaaa aatactggag ctaacaatga agaacagaag   1800
taatctgatt agtcaaatta ttaagtgcca tggattactt tatgcagcag tcaggtacat   1860
agttaggtga acccaaaaga aaaactcttg aaaacaagag atttcttcca tgcacattta   1920
caatattgag gtataattaa catgataaag tgtttccttc taacgagttg tagaaatctg   1980
agtaaccacc caaaaagca atagaatgtt tctgtcaccc caaaacactc ccttctgccc    2040
ctcttcagac agtccttcag ctatttcatg gctctcaccc tagttttttt ttttttttgca   2100 cttttttttt tccgggggta taggggaggt gtgggcgac agggtctgtc ttgttctgtc    2160
tcccaggctg aagtgcagtg cagtggtatg atcatggctc actgcagcct tggtttcctg   2220
ggcataagtg gtcttcccac ttcagcctcc tgagtagctg agactataga ctagcataac   2280
cacactggct aatttttgt ggagatgaag tctcactatg ttgcccaggc tggtctcgaa    2340
ctcctgggct caaacaatcc tcccgcctca gccttccaaa ttgctgggat tatagtcatg   2400
aggcacctag tctggccctt ttgcaagact ttaatctgaa atctaaattt ttaaaattta   2460
agtacttaca aaggatatac tatccaacat attgcatatt atatatgtgc tttaaagttt   2520 ttttttttt ttgagagacg gtctcacttt gtcatccaag ctggagtgca gtggtgcaaa    2580
cacggcccac ctcctgggct caagtgatcc tccagcctca gcttccctca caggcattca   2640
ctatcactcc cagctaatta aaataatttg tagacggtgt ctcgttatgt tgcccaggct   2700
ggtctcgaac tcctgggttt aagtgattcc cccgcctcag cctcccaaag tgttgggctt   2760
acagccttga gccactatgc ttggctcaaa gatatttta tgaaagccct gggactatag    2820
atttagctga ttaaatttat agaaaaagtc ctgtcatata aactggcaaa gtctgttctt   2880
aatttaatta gccaaatcag acttaacttc cgtcagaaca tgtcttggtt ttaattcaga   2940
taaacacaca aacatacttc tctggcacag ccttcagaag catcagtttt tgttttgttt   3000
tgttttgttt tttgagacag ggtcttgctc tgtcgcccag gctggagtgc actggcacaa   3060
tcacagttca ctgcagcctc gacctcccag atccaagcaa tcctcccacc taagcctccc   3120
aagtagctgg gtctataggc gcgtgccacc accatgccca gctgaatttt gtatttttg    3180 tacagacagc attttgccat gttgcccagg ctggtcccaa acttctagcc tcaagcaacc   3240
ctcctgcctc agcctctcaa agtgctagga ttgcagtcct gagctactgc ccctacccct   3300
ctttgcgtct taggagtcat ttagattttt tttgatcctt ttgtttagtg cctctggagc   3360
tgcttacacc aaggcaatac gccttgatat actggatggt tgagaggcag cctctttttt   3420
tttttttttt tttttttttt tttggaggat agggagtatg gctgttgtga aagggaggt    3480 aaagagaaat ggtagatctg aagaggcctc atcagagcac atattttagg acaacacata   3540
```

-continued

| | | |
|---|---|---|
| tggaaattgg acatctttaa gttggttttcc atagagctat gcatgtatcc ttaccccat | 3600 |
| gggaaaatgt tggtgtgttc tcaagggtat gcatgtgtca ttttgaagac caaggccta | 3660 |
| gaattgtcaa acttaaggat cataaaaatc atgagggttg cttgttaaaa atgtccaaac | 3720 |
| gtgcagagac tgatctttga gatctggacc aggaatttgc atttgaacaa gtgttcctgg | 3780 |
| aatctctatg caagttttat acagaacata cttttggaat ccttgcccta gacagggtg | 3840 |
| tccaatcttt tggcttccct ggtccacaat ggaagaagaa ttgtcttgga ccacacataa | 3900 |
| aatacactaa cactaacaat agctgatgag ctaaaaaaaa aaaaaaaaaa aatcgtggac | 3960 |
| cgggcgtagt ggctcacgcc tgtaatccca cactttggg agatcaccta ggtcgggagt | 4020 |
| ttgagaccag cctgaccgac atggagaaac cccattttta ctaaaaatac aaaaaattag | 4080 |
| ctgggcatgg tggtgcatgc ctgtagtccc agctactcag gaggctgagg caggagaatc | 4140 |
| gcttgaacct gagaggggga gattgcggtg agctgagatt gcgccattgc accccagcct | 4200 |
| gggcaacaat agcgaaactg tctcagaaaa agaaaaaaa aaatcgcaaa agaaaaatc | 4260 |
| tcataatgtc gttgttggtt ttttttttt ttttgagac agtctcactc tgttgcccag | 4320 |
| gctggagtgc aatggcatga tctctgctca ccgcaacctc tgcctcccgg gttcaggtga | 4380 |
| ttctcctgcc tcagcctccc agatagctgg gactacaggc ataccacc atgcctggct | 4440 |
| aattttgta tttttagtag agatgggggt ttcactgtgt tggccaggct ggtctcgaac | 4500 |
| tcctgacctc atgatccaca cacctcggcc tcccaaagtc ctgcgattac aggcgtgagc | 4560 |
| taccgcaccc agccaagttg aattttttaa taaaacttaa gaagtaaaca ttttacttat | 4620 |
| gtttataggt atttgatcct aaatttgaca catcattgcc catgaaagaa tcctcttagg | 4680 |
| ctgctcagct tcactcttcc tgcttgccca ccggggtttt tcactgcttc tgttagcact | 4740 |
| aagtacttag acgatcctaa gatatgtgct tgagccgaat ttcatctttta cttgtaggaa | 4800 |
| actttaaaact atttcttttc ttttcttttt ttttttttt tacttgagat ggagttttgc | 4860 |
| tcttgtcgcc caggctggag tgcagtggag tgatctcggc tcactgcaac ctctgcctcc | 4920 |
| cgggttcaaa tgattctcct gcctcagcct cccaagtagc tgggattaca ggtgtgcacc | 4980 |
| accatgtctg gctaattttg tattttagt agagatggtt tcaccatgtt ggtcaggctg | 5040 |
| gtctcgaact cctgacctca ggtcatccac ccacctcagc ctcgcaaagt gctgagatta | 5100 |
| caggcatgag ccacagcgcc cagcttaaac tattttcttg gtctgttttt gattttcttt | 5160 |
| tttccttgcc actgcggtac agattttttt tactcactgc cactaaacta aagcaaggca | 5220 |
| tagtttatat gtgaagtgtt cagagtttac tgctataagg aaacttccaa atactgacat | 5280 |
| ttaccttta gctgtagtta ttgggaccat gtgctctggt tttctggaga ctgccaaatt | 5340 |
| gctcccattt ttctgcatcc cacctggttt ctttctgcat gtccccttttc actttcaaac | 5400 |
| ctcttcattt ggatgttaaa ttatatggtc acctagttat aggtaagcct tgttcgagtt | 5460 |
| gatatcttga ttgtgaggaa ggatctgtgt cattggagct tgtttctgct gcaacgtgct | 5520 |
| gtagactatg aataatgaaa tcacaccaca ttaccatcag atttcttgtt ttagttgtca | 5580 |
| aattaatatt tatgattgtt atcttgggcg aaaagttcag agcagagatg acaaatcatt | 5640 |
| agaacaacga tgaatttcag tattacggct aaaaagttct tctgtctgaa tattaactca | 5700 |
| ctctccttcc agtgtacttc acagtaattg gtatgctttt ttatttaatg cttaaatcaa | 5760 |
| actttataaa aatcttagac cagatcttta atatggtatg ccatttcccc agtctaccaa | 5820 |
| tggaatagta tgggtttcta atcctaggct tgtacaatgg attggagttg agccatgcca | 5880 |
| gcctccacac tgccactaac ttctgtaatg taagattgag tcactgccaa gcatttgaaa | 5940 |

```
tatgcagttg tgttttaatt ataatttatg tatagttaga tgtatgtagt gcattgtgtg    6000
gtattatttg gtttgtaaga atttattttt aagggtcaag gtcatttgta acattttgtg    6060
tgtgtcaatt caatgcaatg ttggctgcct tttgaagtct ttgatatatt ggtgaatatt    6120
cttctgatct ataatacaaa gctatgtaat gttacctctt gactcgcttt tgaaaggaag    6180
acaattgtta actagatatt tgagtttttt cccctcagaa ttatgtgaat ttctgatata    6240
tggctttaga tactgtgaat ctgttttcca tttagtcagt tatctgctta aattgttcag    6300
aactatatcc taacgagcaa ttagttctga tggttctccc agtcatgagt gtgcatgtgt    6360
gcaagcatgt tttgatcctg atgctacctt tgctaaaaat ggccatagat taggaactag    6420
ctatgttttt agaatcaaag atgaaccggt aagctgtctc atgtaccaaa cgtgaaattt    6480
acagtgttta caaatgtctg gaattttgca ctgccatagg gaatgttaag gttacttggc    6540
tggaatttat cagacttgtg agtaaacaag ttgaagttta gcagatgagg gggaatattg    6600
aggcccctaa ggctaaacaa aataatcagt atctgagata gtggctaatg tggctcccca    6660
ggcctaattt gggaacagtt tttcctgatt gctttgagaa gtactttctt ttgacagaaa    6720
ttttcattct gcttgccatt gctatattct ccctttatag gagccattgg atttctttcc    6780
ttttgtggga aatgtcccat tagcatttc agatcttttg atgtgcacta atgccattat    6840
tggtaatgcc gttattggtg aatacagcat agttaaataa actgttacag taaatctaca    6900
cttggatttg ctgcacctct accaatagcc ttttgaatga ctgaaagtgt taacagagaa    6960
agaggcatgt ctgcagaaag agatagctaa tattttttgg tactttatct gaaatccaag    7020
atgctgcttc ccctgcaggt tgttttcctt cttacgatcc tcattgaatc ccctctggga    7080
gcacaggaca gttagtagaa ctctccattt cttttttttt tttttttagac ggagtctctc    7140 tctgtcgccc cggctggagt gcagtggcgc gatctcggct cactgcaacc tccgcctccc    7200
gggttcaccc cattctcctg cctcagcctc cctagtagct gggactatag gcgcccgcca    7260
ccacgcctgg ctaattttg tattttatt ggagacgggg tttcaccgtc ttagccagga    7320
tggtcttgat ctcctgacct cgtgatctgc ccacctcagc ctcccaaagt actgggatta    7380
caggcgtgag ccaccgcgcc cggccggaac tctccatttc ttaaggtaaa gagggtcaag    7440
gatacctaaa aagggtcaaa taatgctaga agagcaattc ctctttcaga gcagttgctg    7500
taatttggca aatgctttat cgaagattga tattaggcta ggggcggtgg cttacgcctg    7560
taatcccagc actttgggag gccgaggtgg gtggattgcc tgagctcagg agttcgagac    7620
cagtctgacc agtatggtga aaccctgtct ctactaaaaa tacaaaaatt agccggtcgt    7680
ggtggcgtgc acctgtagtc ccagctactt ggcaggttga gacaggagaa tcgcttgaac    7740
ctgggaggtg gaggttgcag tgagccgaga ctgcaccact gcgctccac ctgggtgaca    7800 gagactctgt ctcaaaaaaa aggacattta tcattataac atcttattag agccctaat    7860 ttcttatctg aaggcactgt ttttttttt aaacagttaa gtactgatgt caacagacaa    7920
atatttctga tcagatagtc ccctgtcaac agtagcaaat gtggtttcat aaagtgggaa    7980
gaaaacagca ttttaaagta acttttggg agactgattt gagtaataat aaaactctgg    8040
tctcccttaa gaaaaaaaaa ccttccacc tttactgtgt catttatatc cccttagttc    8100
caaagttaat tatcttattt ctggatattg cttttatacc aaagaccctt atcagccctt    8160
gtaactacag tatctttaga taagattcct ctttccagtc agtcctggga aatgtttctg    8220
ttgcagagtt aggcggtaga tgggaagctg tgatggcaga gctactatct aataaagtaa    8280
caactcgtag ttgaggcttc ctttctgtgt gtgatggggg atagggagtt agctcccctg    8340
```

```
ttgtctcagc actaagaaat tgaggtcagg ccaggcgcgg tggttcactc ctgttattcc    8400
agcactgggg tggccaaagt gggcagattg cttgcgctct ggagctcgag accagcctgg    8460
gcaacatggt gaaaccctgt ctctaccaaa aatacaaaaa aaaagctggg catggtgggt    8520
gcatgcttgt cccagctact gaggaggctg aggtgggagg atcgcttgag cctgggaggt    8580
ggaggttgca gtgagctgag atggcaccac tgcaatccaa ggtgggtgac agagacgctg    8640
tctcaaagaa attgaggtca ggcttccttc ttacagaatt atttttttct ctgtagtttg    8700
cctcattttt tcactttctt ttcaatgaga atcgaagtgt ttcttttggg ttttttttc    8760 cccctttaa aatcaacagg aaatgtttca aggagggat gaaatgcttc ttggcttcct    8820
cagcacttgg caaggtagac ctcatagcaa ccttgaatat gactttcttt agtctctagc    8880
tatgcactat taagtgcctc ttgggtagag gtagagttaa gtattgagtg ccagtcttga    8940
cgtccgtatg cctcagtttt tctcatatat aaaaagcagt atacatacct acccttttct    9000
acctcatcat ttgttgtagg gattaaatcc gggagagcaa ttctgaagcc tataaatttc    9060
cttgaagaga tctaagaacc tattatgctc ttggtgtacc aagctctggg gtatatattc    9120 agaataccte atgttctgga agctgagcac tagctcccct ttattgcctg cctggcagag    9180
cctgtttgat tactgcaggc cttttaccc atgcttctag tttaggtatt ctttctttga    9240
tatgaggctc ttgaccagaa aagagttctt tctctaggtg ttctgagaga agtttgtaaa    9300
tttggatagt acattctatc ctgataaaac caccttgctg tggtcttgat gtacaaaaaa    9360
aaattttttt tttgagacag agtcttactc tgtcacccag gctggaatgc agtggcgcaa    9420
tcttggttca ctgcaacccc cgcctcctgg gttcaagcga tcctcctgcc tcaacctctc    9480
aagtagctgg gactacaggc gtgcaccacc acacctggct aattttgtat ttttagtaga    9540
gacagggttt caccatgttg gccaggctgg tcttgaactc ctgacctcag gcgatctgcc    9600
cgccttggcc tcccaaagta ctgggattac aggcgtgagc aactgctcct ggcccaaaac    9660
atctctttct acatacactt gagtaggtgg cataaaatgc actgtcaata tatagaaaac    9720
atgaaatttt ccaaatattt ccgatcagag aatcacaaga gcagcaaatg tggtttcata    9780
agtgggaaga aagcagcaat ttaaaataac ttttgggag actgaattga gtaataataa    9840
aacttcagtc tttcgctaat aataataata ataataataa taacaacaac ttattgaatg    9900
tggccagctc actagatgag gaaagaggaa ggcattttct gcattcttgc ctagtttcc    9960 ttataagcac cactaagtta atagctctgt cttttggtg tttgcactat gtaatgcttt   10020
taatactttt taattgtgct tttttatgta ttaaatgttt ttccttttgc ca           10072
```

<210> SEQ ID NO 9
<211> LENGTH: 308
<212> TYPE: PRT
<213> ORGANISM: Homo sapiens

<400> SEQUENCE: 9

Met Arg Ala Leu Val Leu Leu Ser Leu Phe Leu Leu Gly Gly Gln
1               5                   10                  15

Ala Gln His Val Ser Asp Trp Thr Tyr Ser Glu Gly Ala Leu Asp Glu
            20                  25                  30

Ala His Trp Pro Gln His Tyr Pro Ala Cys Gly Gly Gln Arg Gln Ser
        35                  40                  45

Pro Ile Asn Leu Gln Arg Thr Lys Val Arg Tyr Asn Pro Ser Leu Lys
    50                  55                  60

-continued

```
Gly Leu Asn Met Thr Gly Tyr Glu Thr Gln Ala Gly Glu Phe Pro Met
 65                  70                  75                  80

Val Asn Asn Gly His Thr Val Gln Ile Ser Leu Pro Ser Thr Met Arg
                 85                  90                  95

Met Thr Val Ala Asp Gly Thr Val Tyr Ile Ala Gln Gln Met His Phe
            100                 105                 110

His Trp Gly Gly Ala Ser Ser Glu Ile Ser Gly Ser Glu His Thr Val
        115                 120                 125

Asp Gly Ile Arg His Val Glu Ile His Ile Val His Tyr Asn Ser
    130                 135                 140

Lys Tyr Lys Ser Tyr Asp Ile Ala Gln Asp Ala Pro Asp Gly Leu Ala
145                 150                 155                 160

Val Leu Ala Ala Phe Val Glu Val Lys Asn Tyr Pro Glu Asn Thr Tyr
                165                 170                 175

Tyr Ser Asn Phe Ile Ser His Leu Ala Asn Ile Lys Tyr Pro Gly Gln
                180                 185                 190

Arg Thr Thr Leu Thr Gly Leu Asp Val Gln Asp Met Leu Pro Arg Asn
            195                 200                 205

Leu Gln His Tyr Tyr Thr Tyr His Gly Ser Leu Thr Thr Pro Pro Cys
    210                 215                 220

Thr Glu Asn Val His Trp Phe Val Leu Ala Asp Phe Val Lys Leu Ser
225                 230                 235                 240

Arg Thr Gln Val Trp Lys Leu Glu Asn Ser Leu Leu Asp His Arg Asn
                245                 250                 255

Lys Thr Ile His Asn Asp Tyr Arg Arg Thr Gln Pro Leu Asn His Arg
            260                 265                 270

Val Val Glu Ser Asn Phe Pro Asn Gln Glu Tyr Thr Leu Gly Ser Glu
        275                 280                 285

Phe Gln Phe Tyr Leu His Lys Ile Glu Glu Ile Leu Asp Tyr Leu Arg
    290                 295                 300

Arg Ala Leu Asn
305
```

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
gaaaaacagc agcaaaagca                                                 20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
gggggaccta tcaggacaga                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
caagtgctcc tgaactggtg                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
ccaagtgctc ctgaactggt                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
ccggactggt cctttctgta                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ccggactggt cctttctgta                                               20

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
agcgttgaaa gagagacact g                                             21

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
cagtgagatt cccagttctt cc                                            22

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gcagggaatg ccaattctaa                                               20

```
<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
tggcaagtct gtgtcatggt                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
gccacatatg ctgtcccttg                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
gccgtctcat tggtcttcac                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
taccgtgagg atggtgtgac                                               20

<210> SEQ ID NO 23
<211> LENGTH: 22
<212> TYPE: DNA
<213> ORGANISM: Artificial Sequence
<220> FEATURE:
<223> OTHER INFORMATION: Synthetic

<400> SEQUENCE: 23
caaatgtggc aattattttg ga                                            22

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
gatgacaagc agaagccagt t                                             21

<210> SEQ ID NO 25
<211> LENGTH: 20
<212> TYPE: DNA
<213> ORGANISM: Artificial Sequence
<220> FEATURE:
<223> OTHER INFORMATION: Synthetic
```

<400> SEQUENCE: 25
gatgacaagc agaagccagt                                           20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
ctcacggtgg agcagaattt                                           20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
ctcacggtgg agcagaattt                                           20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
gggactgtgg ctggatgtaa                                           20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
tgggttcctg aatgttcctg                                           20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
tcaggaaaaa gggtgcagac                                           20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
tcaggaaaaa gggtgcagac                                           20

```
<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
tggaagttaa ctgcaccatc a                                              21

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
acgcccatct ttatcaccag                                                20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
ttgtaccccg gaaccaagta                                                20

<210> SEQ ID NO 35
<211> LENGTH: 19
<212> TYPE: DNA
<213> ORGANISM: Artificial Sequence
<220> FEATURE:
<223> OTHER INFORMATION: Synthetic

<400> SEQUENCE: 35
cggaaccaag tacgagctg                                                 19

<210> SEQ ID NO 36
<211> LENGTH: 19
<212> TYPE: DNA
<213> ORGANISM: Artificial Sequence
<220> FEATURE:
<223> OTHER INFORMATION: Synthetic

<400> SEQUENCE: 36
acccaggatg gagatcagt                                                 19

<210> SEQ ID NO 37
<211> LENGTH: 18
<212> TYPE: DNA
<213> ORGANISM: Artificial Sequence
<220> FEATURE:
<223> OTHER INFORMATION: Synthetic

<400> SEQUENCE: 37
ctgggtcctc gtcagagc                                                  18

<210> SEQ ID NO 38
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 38
agaatttgac ggcagctgag                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
ccaggtcatc gtgaaaatca                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
atcttccgtt gagccatctg                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
atgtctcgga tcttccgttg                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
acggaaaatt ggaagctgtg                                              20

<210> SEQ ID NO 43
<211> LENGTH: 21
<212> TYPE: DNA
<213> ORGANISM: Artificial Sequence
<220> FEATURE:
<223> OTHER INFORMATION: Synthetic

<400> SEQUENCE: 43
cattaaggta cgagcaggtg a                                            21

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
tttgtccggg aagacttttg                                              20
```

-continued

```
<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
tttgtccggg aagactttg                                                    20

<210> SEQ ID NO 46
<211> LENGTH: 21
<212> TYPE: DNA
<213> ORGANISM: Artificial Sequence
<220> FEATURE:
<223> OTHER INFORMATION: Synthetic

<400> SEQUENCE: 46
gtggcagtgt actgaatgca a                                                 21

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
tggcagtgta ctgaatgcaa                                                   20

<210> SEQ ID NO 48
<211> LENGTH: 19
<212> TYPE: DNA
<213> ORGANISM: Artificial Sequence
<220> FEATURE:
<223> OTHER INFORMATION: Synthetic

<400> SEQUENCE: 48
aaggcccaac aacgaaaac                                                    19

<210> SEQ ID NO 49
<211> LENGTH: 21
<212> TYPE: DNA
<213> ORGANISM: Artificial Sequence
<220> FEATURE:
<223> OTHER INFORMATION: Synthetic

<400> SEQUENCE: 49
tcagacgtgg agagagaatg g                                                 21

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
ggcacaagct tcaggtcttc                                                   20

<210> SEQ ID NO 51
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 51
gtcgtgggcc agtaccagt                                                    19

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
gtggaagctg tctggcttct                                                   20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
gtggaagctg tctggcttct                                                   20

<210> SEQ ID NO 54
<211> LENGTH: 21
<212> TYPE: DNA
<213> ORGANISM: Artificial Sequence
<220> FEATURE:
<223> OTHER INFORMATION: Synthetic

<400> SEQUENCE: 54
cattgccctc aacgaccact t                                                 21

<210> SEQ ID NO 55
<211> LENGTH: 24
<212> TYPE: DNA
<213> ORGANISM: Artificial Sequence
<220> FEATURE:
<223> OTHER INFORMATION: Synthetic

<400> SEQUENCE: 55
accactttgt caagctcatt tcct                                              24

<210> SEQ ID NO 56
<211> LENGTH: 22
<212> TYPE: DNA
<213> ORGANISM: Artificial Sequence
<220> FEATURE:
<223> OTHER INFORMATION: Synthetic

<400> SEQUENCE: 56
caccctgttg ctgtagccaa at                                                22

<210> SEQ ID NO 57
<211> LENGTH: 19
<212> TYPE: DNA
<213> ORGANISM: Artificial Sequence
<220> FEATURE:
<223> OTHER INFORMATION: Synthetic

<400> SEQUENCE: 57
atgtgggcca tgaggtcca                                                    19
```

SALIVARY TRANSCRIPTOMIC AND PROTEOMIC BIOMARKERS FOR BREAST CANCER DETECTION

CROSS-REFERENCES TO RELATED APPLICATIONS

The present application claims priority to provisional application U.S. Ser. No. 61/303,200, filed Feb. 10, 2010, herein incorporated by reference in its entirety.

STATEMENT AS TO RIGHTS TO INVENTIONS MADE UNDER FEDERALLY SPONSORED RESEARCH OR DEVELOPMENT

This invention was made with Government support under Grant No. DE016275, awarded by the National Institutes of Health. The Government has certain rights in this invention.

BACKGROUND

Breast cancer is the most frequent neoplasm and the leading cause of cancer mortality in women worldwide. According to estimates, approximately 41,000 women in the United States and 130,000 women in the European Union die from breast cancer yearly.

Detection of breast cancer at the earliest stages results in a much greater favorable outcome, with 10-year disease-free survival rate as high as 98% in patients in which the tumor stage is pT1a,bN0M0 (measuring 1 cm or less, with disease-free axillary lymph nodes and no distant metastasis). Needless to say, early detection is of paramount importance in reducing mortality from this major public health burden.

Current breast cancer detection methods are based on physical examination and imaging (for example, mammography, ultrasound, and MRI). These methods can produce a substantial percentage of false positive and false negative results especially in women with dense parenchymal breast tissue. Consequently, screening results in a number of negative biopsy results yielding a high percentage of false positives. There is also a demonstrated lack of sensitivity in detecting cancerous lesions in younger women yielding a significant percentage of false negatives. Accordingly, a clear need exists for added modalities of screening for breast cancer.

In the last decade, biomarker discoveries for breast cancer detection have focused on blood/or tissue, using proteomic, transcriptomic, and genomic approaches. In comparison to prognostic biomarkers, the development of detection biomarkers has been limited, mainly due to a lack of sensitivity and specificity for this clinical context. Most importantly, the use of tissue biomarkers for early detection will be limited to patients at very high risk because they rely on invasive procedures.

As such, a need exists for methods useful for detecting breast cancer, and in particular biomarkers that can detect early stages of the disease and are largely non-invasive.

BRIEF SUMMARY OF THE INVENTION

In accordance with some embodiments of the invention, a method of determining the likelihood of the presence or occurrence of breast cancer in a test subject is provided. The disclosed method includes analyzing a saliva sample from the subject with an assay that specifically detects at least two biomarkers in the saliva sample. The biomarkers are selected from the group of: S100A8 (S100 calcium binding protein A8) (SEQ ID NO: 1), CSTA (cystatin A) (SEQ ID NO:2), GRM1 (glutamate receptor, metabotropic 1) (SEQ ID NO: 3), TPT1 (tumor protein, translationally-controlled 1) (SEQ ID NO:4), GRIK1 (glutamate receptor, ionotropic, kainate 1) (SEQ ID NO: 5), H6PD (hexose-6-phosphate dehydrogenase) (SEQ ID NO: 6), IGF2BP1 (insulin-like growth factor 2 mRNA binding protein 1) (SEQ ID NO: 7), MDM4 (3T3 cell double minute 4) (SEQ ID NO: 8), and CA6 (carbonic anhydrase VI) (SEQ ID NO: 9). The relative occurrence of at least two of these biomarkers is determined and compared to a control, thereby allowing the breast cancer status of the test subject to be determined.

In some embodiments, one of the biomarkers of the at least two biomarkers is cystatin A (CSTA). In other embodiments, two of the at least two biomarkers is CSTA and transformed 3T3 cell double minute 4 (MDM4). The relative occurrence of these biomarkers or these biomakers and others in these instances is determined and compared to a control, for example, thereby allowing the breast cancer status of the test subject to be determined.

In some embodiments, the method of determining the likelihood of the presence or occurrence of breast cancer entails measuring at least three biomarkers. In some embodiments, two of the at least three biomarkers are CSTA and MDM4. The relative occurrence of these biomarkers or these biomakers and others in these instances is determined and compared to a control, for example, thereby allowing the breast cancer status of the test subject to be determined.

In some embodiments, one of the biomarkers of the at least two biomarkers is anhydrase VI (CA6) polypeptide.

In other embodiments, the method of determining the likelihood of the presence or occurrence of breast cancer in a test subject includes an assay in which a nucleic acid encoding at least one biomarker is detected. The nucleic acid can be detected by, for example, mass spectroscopy, polymerase chain reaction (PCR), microarray hybridization, thermal sequencing, capillary array sequencing, or solid phase sequencing.

In other embodiments, the method of determining the likelihood of the presence or occurrence of breast cancer in a test subject includes an assay in which a polypeptide encoding at least one biomarker is detected. The polypeptide can be detected by, for example, enzyme-linked immunosorbent assay (ELISA), Western blot, flow cytometry, immunofluorescence, immunohistochemistry, or mass spectroscopy.

In accordance with other embodiments of the invention, a method for assessing the efficacy of a therapy is disclosed. This method includes analyzing a first saliva sample from the subject with an assay that specifically detects at least two biomarkers selected from the group consisting of S100A8, CSTA, GRM1, TPT1, GRIK1, H6PD, IGF2BP1, MDM4, and CA6. This first analysis provides a first expression profile. A therapy is applied to a subject. An analysis of a second saliva sample from the subject is undertaken with an assay that specifically detects at least two biomarkers selected from the group consisting of S100A8, CSTA, GRM1, TPT1, GRIK1, H6PD, IGF2BP1, MDM4, and CA6 thereby providing a second expression profile. The first and second expression profiles are compared in order to assess the efficacy of a therapy.

In another embodiment, a solid support is provided, wherein the solid support includes a capture binding probe selective for at least two biomarkers selected from the group of S100A8, CSTA, GRM1, TPT1, GRIK1, H6PD, IGF2BP1, MDM4. In some embodiments, a first and a second solid support are provided, wherein the first solid support includes a capture binding probe selective for at least two biomarkers selected from the group consisting of S100A8, CSTA, GRM1, TPT1, GRIK1, H6PD, IGF2BP1, MDM4, and wherein the second solid support includes a capture binding ligand for CA6.

In some embodiments, the capture binding ligand of the kit is an antibody. In another embodiment the kit provides one or more primers for the selective amplification of at least two biomarkers, wherein at least two of the biomarkers are selected from the group of: S100A8, CSTA, GRM1, TPT1, GRIK1, H6PD, IGF2BP1, MDM4. In some embodiments one or more of the primers possess a detectable label.

In accordance with some embodiments of the invention, a method of determining the likelihood of the presence or occurrence of breast cancer in a test subject is provided. The disclosed method includes analyzing a saliva sample from the subject with an assay that specifically detects at least nine biomarkers in the saliva sample. The biomarkers are selected from the group of: S100A8 (S100 calcium binding protein A8) (SEQ ID NO: 1), CSTA (cystatin A) (SEQ ID NO:2), GRM1 (glutamate receptor, metabotropic 1) (SEQ ID NO: 3), TPT1 (tumor protein, translationally-controlled 1) (SEQ ID NO:4), GRIK1 (glutamate receptor, ionotropic, kainate 1) (SEQ ID NO: 5), H6PD (hexose-6-phosphate dehydrogenase) (SEQ ID NO: 6), IGF2BP1 (insulin-like growth factor 2 mRNA binding protein 1) (SEQ ID NO: 7), MDM4 (3T3 cell double minute 4) (SEQ ID NO: 8), and CA6 (carbonic anhydrase VI) (SEQ ID NO: 9). The relative occurrence of at least nine biomarkers is determined and compared to a control, thereby allowing the breast cancer status of the test subject to be determined.

In any of the embodiments above, wherein a method for determining the likelihood of the presence or occurrence of breast cancer in a test subject, the number of biomarkers used can be 2, 3, 4, 5, 6, 7, 8, 9, or more.

These and other embodiments, features and potential advantages will become apparent with reference to the following description and drawings.

BRIEF DESCRIPTION OF THE DRAWINGS

FIG. 3 represents the demographic information of all the subjects used.

FIG. 4 represents biomarkers for breast cancer detection and effect of confounding factors (sample set n=93). The Mann-Whitney rank sum test was used to determine marker validation. Possible confounding factors, including age, ethnicity, smoking status, menopausal status, and HRT treatment, were evaluated for the biomarkers by logistic regression model. Linear regression model was constructed for each marker and used the factors cancer/normal and one of the confounders. cv.err:cross validation error rate.

FIG. 6 represents cross-disease comparisons of the salivary mRNA biomarkers. The identified mRNA biomarkers for breast cancer detection were checked against other microarray datasets. t-test p-values were calculated for the identified breast cancer genes to other microarray datasets to check for significant variation (*after Boneferonni correction, P<0.0006) between patients and controls in those diseases. Sample sizes were 10 versus 10 for oral cancer, 10 versus 10 for lung cancer, 12 versus 12 for pancreatic cancer, 11 versus 11 for ovarian cancer, 13 versus 13 for diabetes, 8 versus 10 for primary Sjögren's Syndrome, and 10 versus 10 for breast cancer.

DETAILED DESCRIPTION OF THE INVENTION

Introduction

Figure 1:
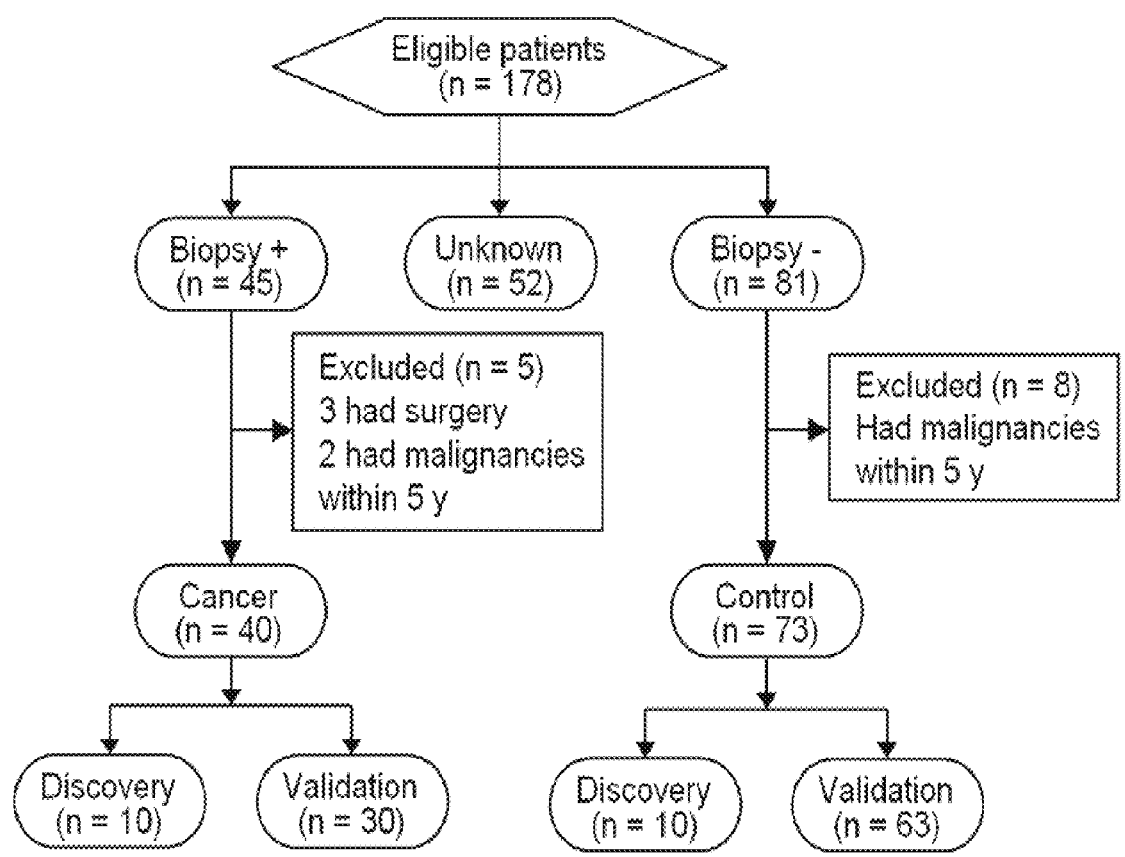
FIG. 1 is a schematic of the study designed to identify and validate biomarkers associated with breast cancer.
Figure 2:
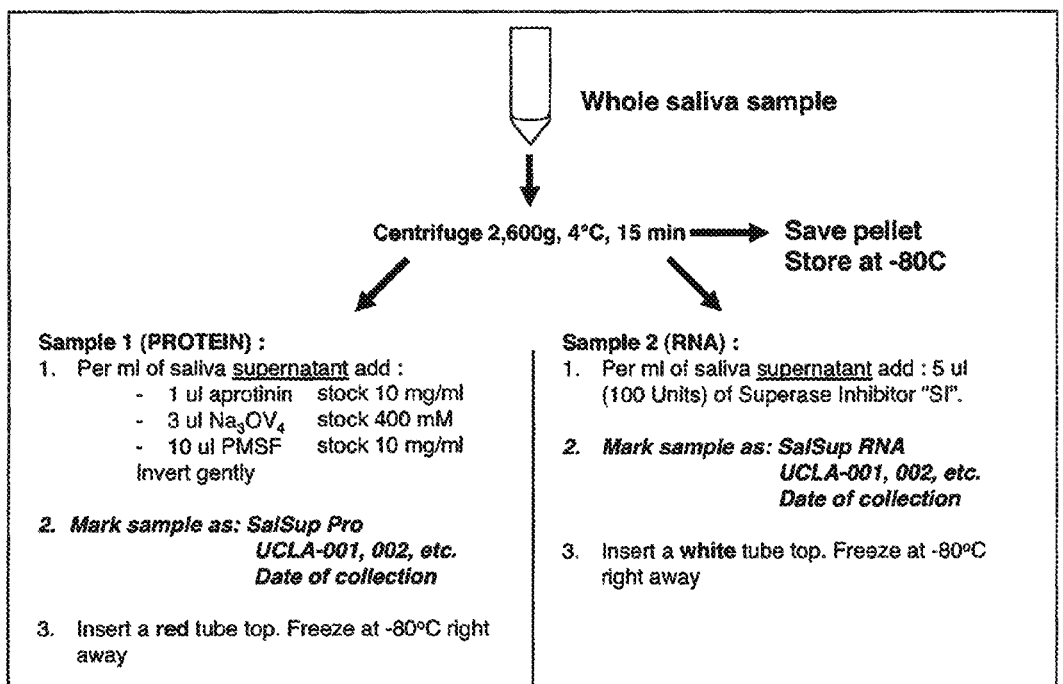
FIG. 2 is a schematic representation of the protocol for saliva collection.
Figure 5:
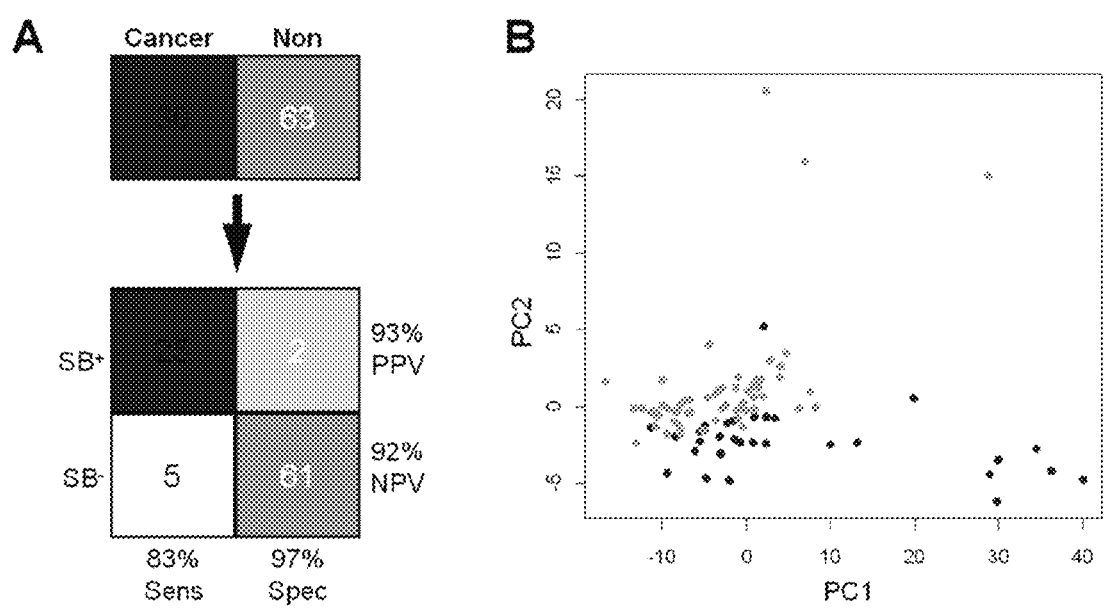
FIG. 5 demonstrates the sensitivity achieved using a combination of the identified biomarkers. (A) The shading of the contingency table boxes reflects the fraction of each samples type in each quadrant. "Cancer" and "Non' headings indicate subjects with and without cancer, respectively. SB+ and SB−, salivary biomarker test positive or negative; NPV, negative predictive value; PPV, positive predictive value; Sen, sensitivity; Spec, specificity. (B) Score plot of principle component analysis (PCA). Combining the nine biomarkers, the control subjects (light shaded) separate from breast cancer patients (dark shading) with cumulative proportions of 66.9% for PC1 and 21.6% for PC2.

Early detection of breast cancer offers the promise of easier treatment (smaller surgeries, less radiation or chemotherapy) and improved survival. Conventional screening (physical examination and mammography) has a less-than desirable sensitivity and specificity. A sensitive assay to identify biomarkers using non-invasively collected specimens is therefore ideal for breast cancer detection.

While saliva is a source of easily accessible bodily fluids, there has been little effort to study its value in cancer diagnosis. Protein, as well as RNA, can be detected in saliva.

The present invention discloses the diagnostic/prognostic significance of nine salivary biomarkers S100A8 (SEQ ID NO: 1)(S100 calcium binding protein A8, also referred to as myloid-related protein 8 (MRP8) or S100A9 (MRP14)), CSTA (SEQ ID NO: 2)(cystatin A), GRM1 (SEQ ID NO: 3)(glutamate receptor, metabotropic 1), TPT1 (SEQ ID NO: 4)(tumor protein, translationally-controlled 1), GRIK1 (SEQ ID NO: 5)(glutamate receptor, ionotropic, kainate 1), H6PD (SEQ ID NO: 6)(hexose-6-phosphate dehydrogenase or glucose 1-dehydrogenase), IGF2BP1 (SEQ ID NO: 7)(insulin-like growth factor 2 mRNA binding protein 1), MDM4 (SEQ ID NO: 8)(Mdm4, transformed 3T3 cell double minute 4; HDMX; MDMX; MRP1; MGC132766; DKFZp781B1423), and CA6 (carbonic anhydrase VI) (SEQ ID NO: 9), and combinations thereof, in breast cancer detection. Detection of these and other biomarkers in saliva are useful for diagnosis and prognosis of breast cancer.

Methods for detecting salivary biomarkers (proteins and nucleic acids) include techniques such as ELISA, PCR, for example, RT-PCR or mass spectroscopy, alone or in combination with other markers. Any specific probe can be used for detection, such as an antibody, a receptor, a ligand, RT-PCR etc. Mass spectroscopy can also be used for protein detection. Thus, the present invention can be used alone or as a complement to traditional antigen analysis to enhance the diagnosis of breast and other cancers.

DEFINITIONS

"S100A8," "CSTA," "GRM1," "TPT1," "GRIK1," "H6PD," "IGF2BP1," "MDM4," and "CA6" refer to nucleic acids, e.g., gene, pre-mRNA, mRNA, and polypeptides, polymorphic variants, alleles, mutants, and interspecies homologs that have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a referenced nucleic acid or an amino acid sequence described herein. The nucleic acids and proteins of the invention include both naturally occurring or recombinant molecules. The nucleic acid or protein sequence is provided, for example, in SEQ ID NOs: 1-9.

"Cancer" refers to human cancers and carcinomas, sarcomas, adenocarcinomas, lymphomas, leukemias, etc., including solid and lymphoid cancers, kidney, breast, lung, kidney, bladder, colon, ovarian, prostate, pancreas, stomach, brain, head and neck, skin, uterine, testicular, esophagus, and liver cancer, including hepatocarcinoma, lymphoma, including non-Hodgkin's lymphomas (e.g., Burkitt's, Small Cell, and Large Cell lymphomas) and Hodgkin's lymphoma, leukemia, and multiple myeloma.

"Therapeutic treatment" and "cancer therapies" refers to chemotherapy, hormonal therapy, radiotherapy, and immunotherapy.

The terms "overexpress," "overexpression" or "overexpressed" interchangeably refer to a protein that is transcribed or translated at a detectably greater level, usually in a cancer cell, in comparison to a normal cell. The term includes overexpression due to transcription, post transcriptional processing, translation, post-translational processing, cellular localization (e.g, organelle, cytoplasm, nucleus, cell surface), and RNA and protein stability, as compared to a normal cell. Overexpression can be detected using conventional techniques for detecting mRNA (i.e., RT-PCR, PCR, hybridization) or proteins (i.e., ELISA, immunohistochemical techniques, mass spectroscopy). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a normal cell.

The terms "cancer-associated antigen" or "tumor-specific marker" or "tumor marker" interchangeably refers to a molecule (typically protein or nucleic acid such as RNA) that is expressed in the cell, expressed on the surface of a cancer cell or secreted by a cancer cell in comparison to a normal cell, and which is useful for the diagnosis of cancer, for providing a prognosis, and for preferential targeting of a pharmacological agent to the cancer cell. Oftentimes, a cancer-associated antigen is overexpressed in a cancer cell in comparison to a normal cell, for instance, about 1.2-fold over expression, about 2-fold overexpression, about 3-fold overexpression or more in comparison to a normal cell. Oftentimes, a cancer-associated antigen is a cell surface molecule that is inappropriately synthesized in the cancer cell, for instance, a molecule that contains deletions, additions or mutations in comparison to the molecule expressed on a normal cell. Oftentimes, a cancer-associated antigen will be expressed exclusively on the cell surface of a cancer cell and not synthesized or expressed on the surface of a normal cell. Exemplified cell surface tumor markers include the proteins c-erbB-2 and human epidermal growth factor receptor (HER) for breast cancer, PSMA for prostate cancer, and carbohydrate mucins in numerous cancers, including breast, ovarian and colorectal.

It will be understood by the skilled artisan that markers may be used singly or in combination with other markers for any of the uses, e.g., diagnosis or prognosis of breast cancer, disclosed herein.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site hypertext transfer protocol:// www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1987-2005, Wiley Interscience)).

An example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (hypertext transfer protocol://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof.

Unless otherwise indicated, a particular nucleic acid sequence also implicitly encompasses conservatively modified variants thereof (for example, degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of cancer antigens. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7)

Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include fluorescent dyes, electron-dense reagents, enzymes (for example, as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min, an annealing phase lasting 30 sec.-2 min, and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

"Antibody" means a protein comprising one or more polypeptides substantially encoded by all or part of the recognized immunoglobulin genes. The recognized immunoglobulin genes, for example in humans, include the kappa (κ), lambda (λ) and heavy chain genetic loci, which together compose the myriad variable region genes, and the constant region genes mu (μ), delta (δ), gamma (γ), epsilon (ε) and alpha (α), which encode the IgM, IgD, IgG, IgE, and IgA isotypes respectively. Antibody herein is meant to include full length antibodies and antibody fragments, and may refer to a natural antibody from any organism, an engineered antibody or an antibody generated recombinantly for experimental, therapeutic or other purposes as further defined below. Antibody fragments include Fab, Fab', F(ab')$_2$, Fv, scFv or other antigen-binding subsequences of antibodies and can include those produced by the modification of whole antibodies or those synthesized de novo using recombinant DNA technologies. The term "antibody" refers to both monoclonal and polyclonal antibodies. Antibodies can be antagonists, agonists, neutralizing, inhibitory or stimulatory.

Biomarkers

Biomarkers may originate from epidemiological studies, animal studies, pathophysiological considerations and end-organ experiments. Ideally, a biomarker will have a high predictive value for a meaningful outcome measure, can be or is validated in appropriately designed prospective trials, reflects therapeutic success by corresponding changes in the surrogate marker results, and should be easy to assess in clinical practice.

Biomarkers can be used in conjunction with other diagnostic tools or used alone.

The term "surrogate marker," "biomolecular marker," "biomarker" or "marker" (also sometimes referred to herein as a "target analyte," "target species" or "target sequence") refers to a molecule whose measurement provides information as to the state of a subject. In various exemplary embodiments, the biomarker is used to assess a pathological state. Measurements of the biomarker may be used alone or combined with other data obtained regarding a subject in order to determine the state of the subject. In one embodiment, the biomarker is "differentially present" in a sample taken from a subject of one phenotypic status (e.g., having a disease) as compared with another phenotypic status (e.g., not having the disease). In one embodiment, the biomarker is "differentially present" in a sample taken from a subject undergoing no therapy or one type of therapy as compared with another type of therapy. Alternatively, the biomarker may be "differentially present" even if there is no phenotypic difference, e.g. the biomarkers may allow the detection of asymptomatic risk.

A biomarker may be over-expressed (over-abundant) or under-expressed (under abundant) relative to a control. The biomarker can be an allelic variant, truncated or mutated form of a wild-type nucleic acid or protein. The biomarker can be a splice variant.

A biomarker may be determined to be "differentially present" in a variety of ways, for example, between different phenotypic statuses if the mean or median level (particularly the expression level of the associated mRNAs as described below) of the biomarker in the different groups is calculated to be statistically significant. Common tests for statistical significance include, among others, t-test, ANOVA, Kruskal-Wallis, Wilcoxon, Mann-Whitney and odds ratio.

As described herein, a biomarker may be, for example, a small molecule, an analyte or target analyte, a nucleic acid, a protein, a metabolite or any derivative thereof or any and all combinations of these molecules, with proteins and nucleic acids finding particular use in the invention. As will be appreciated by those in the art, a large number of analytes may be detected using the present methods; basically, any biomarker for which a binding ligand, described below, may be made may be detected using the methods of the invention.

In various embodiments, the biomarkers used in the panels of the invention can be detected either as proteins or as nucleic acids (e.g. mRNA or cDNA transcripts) in any combination. In various embodiments, the protein form of a biomarker is measured. As will be appreciated by those in the art, protein assays may be done using standard techniques such as ELISA assays. In various embodiments, the nucleic acid form of a biomarker (e.g., the corresponding mRNA) is measured. In various exemplary embodiments, one or more biomarkers from a particular panel are measured using a protein assay and one or more biomarkers from the same panel are measured using a nucleic acid assay.

As will be appreciated by those in the art, there are a large number of possible proteinaceous target analytes and target species that may be detected using the present invention. The term "protein," "polypeptide" or "oligopeptide" refers to at least two or more peptides or amino acids joined by one or more peptide bonds. A protein or an amino acid may be naturally or nonnaturally occurring and may be also be an analog, a derivative or a peptidomimetic structure. The term "protein" refers to wild-type sequences, variants of wild-type sequences and either of these containing analogs or derivatized amino acids. In various embodiments, variants of the sequences described herein, including proteins and nucleic acids based on e.g. splice variants, variants comprising a deletion, addition, substitution, fragments, preproprotein, processed preproprotein (e.g. without a signaling peptide), processed proprotein (e.g. resulting in an active form), nonhuman sequences and variant nonhuman sequences may be used as biomarkers.

In various embodiments, the biomarker is a nucleic acid. The term "nucleic acid" or "oligonucleotide" or grammatical equivalents herein means at least two nucleotides covalently linked together. A nucleic acid of the present invention will generally contain phosphodiester bonds, although in some cases, as outlined below, for example in the use of binding ligand probes, nucleic acid analogs are included that may have alternate backbones.

Biomarkers can also be bacterial nucleic acids or proteins. Over 700 species of bacteria have been identified to exist within the mouth. The presence, absence, or level of 16S rRNA from bacteria in a sample may correlate with a disease or condition. "Bacteria" refers to small prokaryotic organisms (linear dimensions of around 1 μm) with non-compartmentalized circular DNA and ribosomes of about 70 S. "16S RNA" refers to a nucleic acid component of the 30S subunit of prokaryotic ribosomes; the gene that encodes the 16S rRNA or the 16S rRNA itself. Bacterial strains of species or phylotypes have less than about a 2% difference in 16S rRNA. Closely related species or phylotypes generally have between about a 2% and about a 4% difference in 16S rRNA, whereas a genus often has between about a 5% and about a 10% difference in 16S rRNA.

To resolve the identity of bacterial populations, probes on a microarray can be designed, for example, to take advantage of conserved features of the 16S rRNA gene. For example, probes complementary to the more conserved features regions identify species in a large phylogenetic group, each group corresponding to a higher taxon (for example, domain, phylum, class, order, or family). Probes complementary to more variable regions distinguish genera and species.

Biomarkers can also include micro RNAs. "MicroRNAs" (miRs) refers to a class of small naturally occurring non-coding RNAs (18-24 nucleotides) that regulate gene expression. Many microRNAs are well conserved across species and they are present in a broad range of species: plants, nematodes, fruit flies and humans. MicroRNAs have partially or perfect complementary sequence to one or more messenger RNA molecules (mRNAs) and their main function is to negatively regulate the expression of genes. In particular, microRNAs bind to the 3' untranslated regions of mRNAs (3-UTR) thus leading to down regulation of mRNAs in a variety of ways such as mRNA cleavage, translational repression and deadenylation.

A variety of experimental approaches and different techniques have been used to identify new microRNAs, as well as to study their expression pattern in the different biological processes. The cloning and identification of new microRNAs have been successfully done from size fractioned RNA samples using small RNA cloning approaches. Other approaches is as putative microRNAs homologues to microRNAs that already have been described in other species or using computational approaches alone or in combination with microarray analysis and sequence-directed cloning.

One of the first techniques used for detection and profiling of microRNAs was Northern Blotting, where hybridization is done with a complementary 32P, digoxigenin-labeled oligo or modified Locked-nucleic-acid (LNA) oligonucleotides after gel separation.

Other techniques that have been developed to specifically detect microRNAs are a modified invader assay (a synthetic oligonucleotide, the probe, which is in an appropriate overlap-flap structure is enzymatically cleavage by a structure-specific 5*nuclease) and in situ hybridization (using fluorescent-labeled complementary probes containing chemically modified nucleotides e.g. LNAs). Another widely used technique for detection and profiling of microRNAs is the use of oligonucleotide micro-array based detection platforms either with DNA capture probes or using modified Locked-nucleic-acid (LNA) oligonucleotides in which the ribose moiety is modified with an extra bridge that connects the 2'-0 and 4'-C atoms.

In addition, quantitative real-time PCR (reverse transcriptase/polymerase chain reaction using Taqman or SYBR green technology) has been used for detection and profiling of precursor or mature microRNAs. This technique is sensitive and requires low amounts of starting material for the detection of individual mature microRNAs. Taqman microRNA arrays have been developed that provide the sensitivity of the qRT-PCR, while at the same time enables the simultaneously detection of different microRNAs in one sample.

Biomarkers can also include metabolites. "Metabolite" or "small molecule" refers to organic and inorganic molecules which are present in a sample. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000).

The metabolites of the cell are generally found free in solution. A "metabolic profile", or "small molecule profile", means a complete or partial inventory of small molecules within a targeted cell, tissue, organ, organism, or fraction thereof (e.g., cellular compartment). The inventory may include the quantity and/or type of small molecules present. The "small molecule profile" may be determined using a single technique or multiple different techniques.

A metabolic profile can be developed by analyzing a sample using for example, techniques such as GC-MS (gas chromatography-mass spectrometry) and LC-MS (liquid chromatography-mass spectrometry).

Biomarker Panels

Any combination of the biomarkers described herein is used to assemble a biomarker panel, which is detected or measured as described herein. As is generally understood in the art, a combination may refer to an entire set or any subset or subcombination thereof. The term "biomarker panel," "biomarker profile," or "biomarker fingerprint" refers to a set of biomarkers. As used herein, these terms can also refer to any form of the biomarker that is measured. Thus, if cystatin A is part of a biomarker panel, then either cystatin A mRNA, for example, or protein could be considered to be part of the panel. While individual biomarkers are useful as diagnostics, combination of biomarkers can sometimes provide greater value in determining a particular status than single biomarkers alone. Specifically, the detection of a plurality of biomarkers in a sample can increase the sensitivity and/or specificity of the test. Thus, in various embodiments, a biomarker panel may include 1, 2, 3, 4, 5, 6, 7, 8, 9, 10 or more types of biomarkers. In various exemplary embodiments, the biomarker panel consists of a minimum number of biomarkers to generate a maximum amount of information. Thus, in various embodiments, the biomarker panel consists of 2, 3, 4, 5, 6, 7, 8, 9 or more types of biomarkers. Where a biomarker panel "consists of" a set of biomarkers, no biomarkers other than those of the set are present. In exemplary embodiments, the biomarker panel consists of 2 biomarkers disclosed herein. In various embodiments, the biomarker panel consists of 3 biomarkers disclosed herein. In various embodiments, the biomarker panel consists of 4 biomarkers disclosed herein. In various embodiments, the biomarker panel consists of 5 biomarkers disclosed herein.

In various exemplary embodiments, the biomarker panel comprises cystatin A. In various exemplary embodiments, the biomarker panel comprises carbonic anhydrase VI.

In various exemplary embodiments, the biomarker panel comprises or consists of two or more of the biomarkers selected from the group of S100A8, CSTA, GRM1, TPT1, GRIK1, H6PD, IGF2BP1, MDM4, and CA6. In various exemplary embodiments two or more of the biomarkers selected from the group of S100A8, CSTA, GRM1, TPT1, GRIK1, H6PD, IGF2BP1, MDM4, and CA6 can be combined with 1, 2, 3, 4 or more additional biomarkers. It should be understood that in this embodiment, the biomarker panel can include any combination of S100A8, CSTA, GRM1, TPT1, GRIK1, H6PD, IGF2BP1, MDM4 and the remainder of these markers.

A biomarker can also be a clinical parameter. The term "clinical parameter" refers to all non-sample or non-analyte biomarkers of subject health status or other characteristics, such as, without limitation, age, ethnicity, gender, family history, height, and weight.

The biomarkers of the invention show a statistically significant difference in breast cancer diagnosis. In various embodiments, diagnostic tests that use these biomarkers alone or in combination show a sensitivity and specificity of at least about 85%, at least about 90%, at least about 95%, at least about 98% and about 100%.

Measurement and Detection of Biomarkers

Biomarkers generally can be measured and detected through a variety of assays, methods and detection systems known to one of skill in the art. The term "measuring," "detecting," or "taking a measurement" refers to a quantitative or qualitative determination of a property of an entity, for example, quantifying the amount or concentration of a molecule or the activity level of a molecule. The term "concentration" or "level" can refer to an absolute or relative quantity. Measuring a molecule may also include determining the absence or presence of the molecule. Various methods include but are not limited to refractive index spectroscopy (RI), ultra-violet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance (such as according to systems provided by Biacore Life Sciences). See also PCT Publications WO/2004/056456 and WO/2004/088309. In this regard, biomarkers can be measured using the above-mentioned detection methods, or other methods known to the skilled artisan. Other biomarkers can be similarly detected using reagents that are specifically designed or tailored to detect them.

Different types of biomarkers and their measurements can be combined in the compositions and methods of the present invention. In various embodiments, the protein form of the biomarkers is measured. In various embodiments, the nucleic acid form of the biomarkers is measured. In exemplary embodiments, the nucleic acid form is mRNA. In various embodiments, measurements of protein biomarkers are used in conjunction with measurements of nucleic acid biomarkers.

Methods for detecting mRNA, such as RT-PCR, real time PCR, branch DNA, NASBA and others, are well known in the art. Using sequence information provided by the database entries for the biomarker sequences, expression of the biomarker sequences can be detected (if present) and measured using techniques well known to one of ordinary skill in the art. For example, sequences in sequence database entries or sequences disclosed herein can be used to construct probes for detecting biomarker RNA sequences in, e.g., Northern blot hybridization analyses or methods which specifically, and, preferably, quantitatively amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms and mutations, sequence comparisons in test and reference populations can be made by comparing relative amounts of the examined DNA sequences in the test and reference cell populations. In addition to Northern blot and RT-PCR, RNA can also be measured using, for example, other target amplification methods (e.g., TMA, SDA, NASBA), signal amplification methods (e.g., bDNA), nuclease protection assays, in situ hybridization and the like.

In one embodiment in the present invention are biochip assays. By "biochip" or "chip" herein is meant a composition generally comprising a solid support or substrate to which a capture binding ligand (also called an adsorbent, affinity reagent or binding ligand, or when nucleic acid is measured, a capture probe) is attached and can bind either proteins, nucleic acids or both. Generally, where a biochip is used for measurements of protein and nucleic acid biomarkers, the protein biomarkers are measured on a chip separate from that used to measure the nucleic acid biomarkers. For nonlimiting examples of additional platforms and methods useful for measuring nucleic acids, see Publications US/2006/0275782, US/2005/0064469 and DE10201463. In various embodiments, biomarkers are measured on the same platform, such as on one chip. In various embodiments, biomarkers are measured using different platforms and/or different experimental runs.

By "binding ligand," "capture binding ligand," "capture binding species," "capture probe" or grammatical equivalents herein is meant a compound that is used to detect the presence of or to quantify, relatively or absolutely, a target analyte, target species or target sequence (all used interchangeably) and that will bind to the target analyte, target species or target sequence. Generally, the capture binding ligand or capture probe allows the attachment of a target species or target sequence to a solid support for the purposes of detection as further described herein. Attachment of the target species to the capture binding ligand may be direct or indirect. In exemplary embodiments, the target species is a biomarker. As will be appreciated by those in the art, the composition of the binding ligand will depend on the composition of the biomarker. Binding ligands for a wide variety of biomarkers are known or can be readily found using known techniques. For example, when the biomarker is a protein, the binding ligands include proteins (particularly including antibodies or fragments thereof ($F_{ab}$s, etc.) as discussed further below) or small molecules. The binding ligand may also have cross-reactivity with proteins of other species. Antigen-antibody pairs, receptor-ligands, and carbohydrates and their binding partners are also suitable analyte-binding ligand pairs. In various embodiments, the binding ligand may be nucleic acid. Nucleic acid binding ligands find particular use when proteins are the targets; alternatively, as is generally described in U.S. Pat. Nos. 5,270,163; 5,475,096; 5,567,588; 5,595,877; 5,637,459; 5,683,867; 5,705,337 and related patents, hereby incorporated by reference, nucleic acid "aptamers" can be developed for binding to virtually any biomarker. Nucleic acid binding ligands also find particular use when nucleic acids are binding targets. There is a wide body of literature relating to the development of binding partners based on combinatorial chemistry methods. In these embodiments, when the binding ligand is a nucleic acid, preferred compositions and techniques are outlined in PCT Publication WO/1998/020162, hereby incorporated by reference.

In various exemplary embodiments, the capture binding ligand is an antibody. These embodiments are particularly useful for the detection of the protein form of a biomarker.

Detecting or measuring the level (e.g. the transcription level) of a biomarker involves binding of the biomarker to a capture binding ligand, generally referred to herein as a "capture probe" when the mRNA of the biomarker is to be detected on a solid support. In that sense, the biomarker is a target sequence. The term "target sequence" or "target nucleic acid" or grammatical equivalents herein means a nucleic acid sequence that may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction such as PCR etc. In some embodiments, measuring a nucleic acid can thus refer to measuring the complement of the nucleic acid. It may be any length, with the understanding that longer sequences are more specific.

The target sequence may also comprise different target domains; for example, a first target domain of the sample target sequence may hybridize to a first capture probe, a second target domain may hybridize to a label probe (e.g. a "sandwich assay" format), etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the target sequence, the first target domain may be located either 5' to the second domain, or 3' to the second domain.

When nucleic acids are used as the target analyte, the assays of the invention can take on a number of embodiments. In one embodiment, the assays are done in solution format, using any number of solution based formats. In one embodiment, end-point or real time PCR formats are used, as are well known in the art. These assays can be done either as a panel, in individual tubes or wells, or as multiplex assays, using sets of primers and different labels within a single tube or well. In addition to PCR-based solution formats, other formats can be utilized, including, but not limited to for example ligation based assays utilizing FRET dye pairs. In this embodiment, only upon ligation of two (or more) probes hybridized to the target sequence is a signal generated.

In many embodiments, the assays are done on a solid support, utilizing a capture probe associated with the surface. As discussed herein, the capture probes (or capture binding ligands, as they are sometimes referred to) can be covalently attached to the surface, for example using capture probes terminally modified with functional groups, for example amino groups, that are attached to modified surfaces such as silanized glass. Alternatively, non-covalent attachment, such as electrostatic, hydrophobic/hydrophilic adhesion can be utilized. As is appreciated by those in the art and discussed herein, a large number of attachments are possible on a wide variety of surfaces.

In this embodiment, the assays can take on a number of formats. In one embodiment, the target sequence comprises a detectable label, as described herein. In this embodiment, the label is generally added to the target sequence during amplification of the target in one of two ways: either labeled primers are utilized during the amplification step or labeled dNTPs are used, both of which are well known in the art. The label can either be a primary or secondary label as discussed herein. For example, in one embodiment, the label on the primer and/or a dNTP is a primary label such as a fluorophore. Alternatively, the label may be a secondary label such as biotin or an enzyme; for example, in one embodiment, the primers or dNTPs are labeled with biotin, and then a streptavidin/label complex is added. In one embodiment, the streptavidin/label complex contains a label such as a fluorophore. In an alternative embodiment, the streptavidin/label complex comprises an enzymatic label. For example, the complex can comprise horseradish peroxidase, and upon addition of TMB, the action of the horseradish peroxidase causes the TMB to precipitate, causing an optically detectable event. This has a particular benefit in that the optics for detection does not require the use of a fluorimeter.

In alternate embodiments, the solid phase assay relies on the use of a labeled soluble capture ligand, sometimes referred to as a "label probe" or "signaling probe" when the target analyte is a nucleic acid. In this format, the assay is a "sandwich" type assay, where the capture probe binds to a first domain of the target sequence and the label probe binds to a second domain. In this embodiment, the label probe can also be either a primary (e.g. a fluorophore) or a secondary (biotin or enzyme) label. In one embodiment, the label probe comprises biotin, and a streptavidin/enzyme complex is used, as discussed herein. As above, for example, the complex can comprise horseradish peroxidase, and upon addition of TMB, the action of the horseradish peroxidase causes the TMB to precipitate, causing an optically detectable event.

Detection of a target species in some embodiments requires a "label" or "detectable marker" (as described below) that can be incorporated in a variety of ways. Thus, in various embodiments, the composition comprises a "label" or a "detectable marker." In one embodiment, the target species (or target analyte or target sequence) is labeled; binding of the target species thus provides the label at the surface of the solid support.

In embodiments finding particular use herein, a sandwich format is utilized, in which target species are unlabeled. In these embodiments, a "capture" or "anchor" binding ligand is attached to the detection surface as described herein, and a soluble binding ligand (frequently referred to herein as a "signaling probe," "label probe" or "soluble capture ligand") binds independently to the target species and either directly or indirectly comprises at least one label or detectable marker.

By "label" or "labeled" herein is meant that a compound has at least one molecule, element, isotope or chemical compound attached to enable the detection of the compound. In general, labels fall into four classes: a) isotopic labels, which may be radioactive or heavy isotopes; b) magnetic, electrical, thermal; c) colored or luminescent dyes; and d) enzymes; although labels include particles such as magnetic particles as well. The dyes may be chromophores or phosphors but are preferably fluorescent dyes, which due to their strong signals provide a good signal-to-noise ratio for decoding. Suitable dyes for use in the invention include, but are not limited to, fluorescent lanthanide complexes, including those of Europium and Terbium, fluorescein, rhodamine, tetramethylrhodamine, eosin, erythrosin, coumarin, methylcoumarins, pyrene, Malacite green, stilbene, Lucifer Yellow, Cascade Blue, Texas Red, Alexa dyes and others described in the 6th Edition of the Molecular Probes Handbook by Richard P. Haugland, hereby expressly incorporated by reference. Additional labels include nanocrystals or Q-dots as described in U.S. Pat. No. 6,544,732 incorporated by reference.

In various embodiments, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels include, but are not limited to, one of a binding partner pair; chemically modifiable moieties; nuclease inhibitors, enzymes such as horseradish peroxidase, alkaline phosphatases, luciferases, etc. Secondary labels can also include additional labels.

In various embodiments, the secondary label is a binding partner pair. For example, the label may be a hapten or antigen, which will bind its binding partner. For example, suitable binding partner pairs include, but are not limited to: antigens (such as proteins (including peptides)) and antibodies (including fragments thereof ($F_{ab}$s, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents.

In the sandwich formats of the invention, an enzyme serves as the secondary label, bound to the soluble capture ligand. Of particular use in some embodiments is the use of horseradish peroxidase, which when combined with 3,3',5, 5'-tetramethylbenzidine (TMB) forms a colored precipitate which is then detected. In some cases, the soluble capture ligand comprises biotin, which is then bound to a enzyme-streptavidin complex and forms a colored precipitate with the addition of TMB.

In various embodiments, the label or detectable marker is a conjugated enzyme (for example, horseradish peroxidase). In various embodiments, the system relies on detecting the precipitation of a reaction product or on a change in, for example, electronic properties for detection. In various embodiments, none of the compounds comprises a label.

As used herein, the term "fluorescent signal generating moiety" or "fluorophore" refers to a molecule or part of a molecule that absorbs energy at one wavelength and re-emits energy at another wavelength. Fluorescent properties that can be measured include fluorescence intensity, fluorescence lifetime, emission spectrum characteristics, energy transfer, and the like.

Signals from single molecules can be generated and detected by a number of detection systems, including, but not limited to, scanning electron microscopy, near field scanning optical microscopy (NSOM), total internal reflection fluorescence microscopy (TIRFM), and the like. Abundant guidance is found in the literature for applying such techniques for analyzing and detecting nanoscale structures on surfaces, as evidenced by the following references that are incorporated by reference: Reimer et al, editors, *Scanning Electron Microscopy: Physics of Image Formation and Microanalysis,* 2nd Edition (Springer, 1998); Nie et al, *Anal. Chem.,* 78: 1528-1534 (2006); Hecht et al, *Journal Chemical Physics,* 112: 7761-7774 (2000); Zhu et al, editors, *Near-Field Optics: Principles and Applications* (World Scientific Publishing, Singapore, 1999); Drmanac, PCT Publication WO/2004/076683; Lehr et al, *Anal. Chem.,* 75: 2414-

2420 (2003); Neuschafer et al, *Biosensors & Bioelectronics*, 18: 489-497 (2003); Neuschafer et al, U.S. Pat. No. 6,289,144; and the like.

Thus, a detection system for fluorophores includes any device that can be used to measure fluorescent properties as discussed above. In various embodiments, the detection system comprises an excitation source, a fluorophore, a wavelength filter to isolate emission photons from excitation photons and a detector that registers emission photons and produces a recordable output, in some embodiments as an electrical signal or a photographic image. Examples of detection devices include without limitation spectrofluorometers and microplate readers, fluorescence microscopes, fluorescence scanners (including e.g. microarray readers) and flow cytometers.

In various exemplary embodiments, the binding of the biomarker to the binding ligand is specific or selective, and the binding ligand is part of a binding pair. By "specifically bind" or "selectively bind" or "selective for" a biomarker herein is meant that the ligand binds the biomarker with specificity sufficient to differentiate between the biomarker and other components or contaminants of the test sample.

The term "solid support" or "substrate" refers to any material that can be modified to contain discrete individual sites appropriate for the attachment or association of a capture binding ligand. Suitable substrates include metal surfaces such as gold, electrodes, glass and modified or functionalized glass, plastics (including acrylics, polystyrene and copolymers of styrene and other materials, polypropylene, polyethylene, polybutylene, polycarbonate, polyurethanes, Teflon, derivatives thereof, etc.), polysaccharides, nylon or nitrocellulose, resins, mica, silica or silica-based materials including silicon and modified silicon, carbon, metals, inorganic glasses, fiberglass, ceramics, GETEK (a blend of polypropylene oxide and fiberglass) and a variety of other polymers. Of particular use in the present invention are the ClonDiag materials described below.

Frequently, the surface of a biochip comprises a plurality of addressable locations, each of which comprises a capture binding ligand. An "array location," "addressable location," "pad" or "site" herein means a location on the substrate that comprises a covalently attached capture binding ligand. An "array" herein means a plurality of capture binding ligands in a regular, ordered format, such as a matrix. The size of the array will depend on the composition and end use of the array. Arrays containing from about two or more different capture binding ligands to many thousands can be made. Generally, the array will comprise 3, 4, 5, 6, 7 or more types of capture binding ligands depending on the end use of the array. In the present invention, the array can include controls, replicates of the markers and the like. Exemplary ranges are from about 3 to about 50. In some embodiments, the compositions of the invention may not be in array format; that is, for some embodiments, compositions comprising a single capture ligand may be made as well. In addition, in some arrays, multiple substrates may be used, either of different or identical compositions. Thus for example, large arrays may comprise a plurality of smaller substrates.

Accordingly, in one aspect, the invention provides a composition comprising a solid support comprising a capture binding ligand for each biomarker of a biomarker panel. In various embodiments, the capture ligand is a nucleic acid. In various embodiments, the capture binding ligand is an antibody. In various embodiments, the composition further comprises a soluble binding ligand for each biomarker of a biomarker panel.

A number of different biochip array platforms as known in the art may be used. For example, the compositions and methods of the present invention can be implemented with array platforms such as GeneChip® (Affymetrix), CodeLink™ Bioarray (Amersham), Expression Array System (Applied Biosystems), SurePrint microarrays (Agilent), Sentrix® LD BeadChip or Sentrix® Array Matrix (Illumina) and Verigene (Nanosphere).

In various exemplary embodiments, detection and measurement of biomarkers utilizes colorimetric methods and systems in order to provide an indication of binding of a target analyte or target species. In colorimetric methods, the presence of a bound target species such as a biomarker will result in a change in the absorbance or transmission of light by a sample or substrate at one or more wavelengths. Detection of the absorbance or transmission of light at such wavelengths thus provides an indication of the presence of the target species.

A detection system for colorimetric methods includes any device that can be used to measure colorimetric properties as discussed above. Generally, the device is a spectrophotometer, a colorimeter or any device that measures absorbance or transmission of light at one or more wavelengths. In various embodiments, the detection system comprises a light source; a wavelength filter or monochromator; a sample container such as a cuvette or a reaction vial; a detector, such as a photoresistor, that registers transmitted light; and a display or imaging element.

In various exemplary embodiments, a ClonDiag chip platform is used for the colorimetric detection of biomarkers. In various embodiments, a ClonDiag ArrayTube (AT) is used. One unique feature of the ArrayTube is the combination of a micro probe array (the biochip) and micro reaction vial. In various embodiments, where a target sequence is a nucleic acid, detection of the target sequence is done by amplifying and biotinylating the target sequence contained in a sample and optionally digesting the amplification products. The amplification product is then allowed to hybridize with probes contained on the ClonDiag chip. A solution of a streptavidin-enzyme conjugate, such as Poly horseradish peroxidase (HRP) conjugate solution, is contacted with the ClonDiag chip. After washing, a dye solution such as o-dianisidine substrate solution is contacted with the chip. Oxidation of the dye results in precipitation that can be detected colorimetrically. Further description of the ClonDiag platform is found in Monecke S, Slickers P, Hotzel H et al., *Clin Microbiol Infect* 2006, 12: 718-728; Monecke S, Berger-Bächi B, Coombs C et al., *Clin Microbiol Infect* 2007, 13: 236-249; Monecke S, Leube I and Ehricht R, *Genome Lett* 2003, 2: 106-118; Monecke S and Ehricht R, *Clin Microbiol Infect* 2005, 11: 825-833; German Patent DE 10201463; US Publication US/2005/0064469 and ClonDiag, *ArrayTube (AT) Experiment Guideline for DNA-Based Applications*, version 1.2, 2007, all incorporated by reference in their entirety. One of skill in the art will appreciate that numerous other dyes that react with a peroxidase can be utilized to produce a colorimetric change, such as 3,3',5,5'-tetramethylbenzidine (TMB). For information on specific assay protocols, see www.clondiag.com/technologies/publications.php.

In various embodiments, where a target species is a protein, the ArrayTube biochip comprises capture binding ligands such as antibodies. A sample is contacted with the biochip, and any target species present in the sample is allowed to bind to the capture binding ligand antibodies. A soluble capture binding ligand or a detection compound such as a horseradish peroxidase conjugated antibody is allowed to bind to the target species. A dye, such as TMB, is then added and allowed to react with the horseradish peroxidase, causing precipitation and a color change that is detected by a suitable detection device. Further description of protein detection using ArrayTube is found in, for example, Huelseweh B, Ehricht R and Marschall H-J, *Proteomics*, 2006, 6, 2972-2981; and ClonDiag, *ArrayTube (AT) Experiment Guideline for Protein-Based Applications*, version 1.2, 2007, all incorporated by reference in their entirety.

Transmission detection and analysis is performed with a ClonDiag AT reader instrument. Suitable reader instruments and detection devices include the ArrayTube Workstation ATS and the ATR 03.

In addition to ArrayTube, the ClonDiag ArrayStrip (AS) can be used. The ArrayStrip provides a 96-well format for high volume testing. Each ArrayStrip consists of a standard 8-well strip with a microarray integrated into the bottom of each well. Up to 12 ArrayStrips can be inserted into one microplate frame enabling the parallel multiparameter testing of up to 96 samples. The ArrayStrip can be processed using the ArrayStrip Processor ASP, which performs all liquid handling, incubation, and detection steps required in array based analysis. In various embodiments, where a protein is detected, a method of using the ArrayStrip to detect the protein comprises conditioning the AS array with buffer or blocking solution; loading of up to 96 sample solutions in the AS wells to allow for binding of the protein; 3× washing; conjugating with a secondary antibody linked to HRP; 3× washing; precipitation staining with TMB; and AS array imaging and optional data storage.

Those skilled in the art will be familiar with numerous additional immunoassay formats and variations thereof which may be useful for carrying out the method disclosed herein. See generally E. Maggio, *Enzyme-Immunoassay*, (CRC Press, Inc., Boca Raton, Fla., 1980); see also U.S. Pat. Nos. 4,727,022; 4,659,678; 4,376,110; 4,275,149; 4,233,402; and 4,230,767.

In general, immunoassays carried out in accordance with the present invention may be homogeneous assays or heterogeneous assays. In a homogeneous assay the immunological reaction usually involves the specific antibody (e.g., anti-biomarker protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays include immunoblotting, immunofluorescence methods, immunoprecipitation, chemiluminescence methods, electrochemiluminescence (ECL) or enzyme-linked immunoassays.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}S$, $^{125}I$, $^{131}I$), enzyme labels (e.g., horseradish peroxidase, alkaline phosphatase), and fluorescent labels (e.g., fluorescein, Alexa, green fluorescent protein, rhodamine) in accordance with known techniques.

Using any of the methods and compositions described herein, a sample can be assayed to determine levels of a biomarker panel. Thus, in one aspect, the invention provides a method of assaying a sample from a patient to determine concentrations of a biomarker panel in the sample. In some embodiments, the method comprises contacting the sample with a composition comprising a solid support comprising a capture binding ligand or capture probe for each biomarker of a biomarker panel.

The invention further provides kits for use in determining breast health or breast cancer status for a number of medical (including diagnostic and therapeutic), industrial, forensic and research applications. Kits may comprise a carrier, such as a box, carton, tube or the like, having in close confinement therein one or more containers, such as vials, tubes, ampoules, bottles, pouches, envelopes and the like. In various embodiments, the kits comprise one or more components selected from one or more media or media ingredients and reagents for the measurement of the various biomarkers and biomarker panels disclosed herein. For example, kits of the invention may also comprise, in the same or different containers, one or more DNA polymerases, one or more primers, one or more suitable buffers, one or more nucleotides (such as deoxynucleoside triphosphates (dNTPs) and preferably fluorescently labeled dNTPs) and labeling components. The one or more components may be contained within the same container, or may be in separate containers to be admixed prior to use. The kits of the present invention may also comprise one or more instructions or protocols for carrying out the methods of the present invention. The kits may also comprise a computer or a component of a computer, such as a computer-readable storage medium or device. Examples of storage media include, without limitation, optical disks such as CD, DVD and Blu-ray Discs (BD); magneto-optical disks; magnetic media such as magnetic tape and internal hard disks and removable disks; semi-conductor memory devices such as EPROM, EEPROM and flash memory; and RAM. The computer-readable storage medium may comprise software encoding references to the various therapies and treatment regimens disclosed herein. The software may be interpreted by a computer to provide the practitioner with treatments according to various measured concentrations of biomarkers as provided herein. In various embodiments, the kit comprises a biomarker assay involving a lateral-flow-based point-of-care rapid test with detection of risk thresholds, or a biochip with quantitative assays for the constituent biomarkers.

Methods of Diagnosing and Treating

The compositions and methods of the present invention can be used in the prognosis, diagnosis and treatment of disease in a subject. The invention provides compositions and methods for laboratory and point-of-care tests for measuring biomarkers in a sample from a subject. The invention can be generally applied for a number of different diseases. In exemplary embodiments, the disease is breast cancer.

The biomarkers and biomarker panels disclosed herein can be used in methods to diagnose, identify or screen subjects that have, do not have or are at risk for having disease; to monitor subjects that are undergoing therapies for disease; to determine or suggest a new therapy or a change in therapy; to differentially diagnose disease states associated with the disease from other diseases or within subclassifications of disease; to evaluate the severity or changes in severity of disease in a patient; to stage a subject with the disease and to select or modify therapies or interventions for use in treating subjects with the disease. In an exemplary embodiment, the methods of the present invention are used to identify and/or diagnose subjects who are asymptomatic or presymptomatic for a disease. In this context, "asymptomatic" or "presymptomatic" means not exhibiting the traditional symptoms or enough abnormality for disease.

In various embodiments, a method of determining a prognosis of a disease in a subject, diagnosing a disease in a subject, or treating a disease in a subject comprises taking a measurement of a biomarker panel in a sample from the subject. In various exemplary embodiments, the biomarker panel consists of two or more of S100A8, CSTA, GRM1, TPT1, GRIK1, H6PD, IGF2BP1, MDM4, and/or CA6.

The term "disease status" includes any distinguishable manifestation of the disease, including non-disease. For example, disease status includes, without limitation, the presence or absence of disease, the risk of developing disease, the stage of the disease, the progression of disease (e.g., progress of disease or remission of disease over time), the severity of disease and the effectiveness or response to treatment of disease.

A "subject" in the context of the present invention is an animal, preferably a mammal. The mammal can be a human, non-human primate, mouse, rat, dog, cat, horse, or cow, but are not limited to these examples. In various exemplary embodiments, a subject is human and may be referred to as a patient. Mammals other than humans can be advantageously used as subjects that represent animal models of a disease or for veterinarian applications. A subject can be one who has been previously diagnosed or identified as having a disease, and optionally has already undergone, or is undergoing, a therapeutic intervention for a disease. Alternatively, a subject can also be one who has not been previously diagnosed as having a disease. For example, a subject can be one who exhibits one or more risk factors for a disease, or one who does not exhibit a disease risk factor, or one who is asymptomatic for a disease. A subject can also be one who is suffering from or at risk of developing a disease. In certain embodiments, the subject can be already undergoing therapy or can be a candidate for therapy.

As will be appreciated by those in the art, the biomarkers may be measured in using several techniques designed to achieve more predictable subject and analytical variability.

The term "sample" refers to a specimen or culture obtained from a subject and includes fluids, gases and solids including for example tissue. In various exemplary embodiments, the sample comprises saliva. As will be appreciated by those in the art, virtually any experimental manipulation or sample preparation steps may have been done on the sample. For example, wash steps and/or fragmentation may be applied to a sample. In various embodiments, a biomarker panel is measured directly in a subject without the need to obtain a separate sample from the patient.

In one aspect, the invention provides a method of diagnosing a subject for a disease comprising taking a measurement of a biomarker panel; and correlating the measurement with the disease. The term "correlating" generally refers to determining a relationship between one type of data with another or with a state. In various embodiments, correlating the measurement with disease comprises comparing the measurement with a reference biomarker profile or some other reference value. In various embodiments, correlating the measurement with disease comprises determining whether the subject is currently in a state of disease.

The quantity or activity measurements of a biomarker panel can be compared to a reference value. Differences in the measurements of biomarkers in the subject sample compared to the reference value are then identified. In exemplary embodiments, the reference value is given by a risk category as described further below.

In various embodiments, the reference value is a baseline value. A baseline value is a composite sample of an effective amount of biomarkers from one or more subjects who do not have a disease, who are asymptomatic for a disease or who have a certain level of a disease. A baseline value can also comprise the amounts of biomarkers in a sample derived from a subject who has shown an improvement in risk factors of a disease as a result of treatments or therapies. In these embodiments, to make comparisons to the subject-derived sample, the amounts of biomarkers are similarly calculated. A reference value can also comprise the amounts of biomarkers derived from subjects who have a disease confirmed by an invasive or non-invasive technique, or are at high risk for developing a disease. Optionally, subjects identified as having a disease, or being at increased risk of developing a disease are chosen to receive a therapeutic regimen to slow the progression of a disease, or decrease or prevent the risk of developing a disease. A disease is considered to be progressive (or, alternatively, the treatment does not prevent progression) if the amount of biomarker changes over time relative to the reference value, whereas a disease is not progressive if the amount of biomarkers remains constant over time (relative to the reference population, or "constant" as used herein). The term "constant" as used in the context of the present invention is construed to include changes over time with respect to the reference value.

The biomarkers of the present invention can be used to generate a "reference biomarker profile" of those subjects who do not have a disease according to a certain threshold, are not at risk of having a disease or would not be expected to develop a disease. The biomarkers disclosed herein can also be used to generate a "subject biomarker profile" taken from subjects who have a disease or are at risk for having a disease. The subject biomarker profiles can be compared to a reference biomarker profile to diagnose or identify subjects at risk for developing a disease, to monitor the progression of disease, as well as the rate of progression of disease, and to monitor the effectiveness of disease treatment modalities. The reference and subject biomarker profiles of the present invention can be contained in a machine-readable medium, such as but not limited to, analog tapes like those readable by a VCR; optical media such as CD-ROM, DVD-ROM and the like; and solid state memory, among others.

Measurements of the biomarker panels of the invention can lead a practitioner to affect a therapy with respect to a subject. Thus, the invention provides methods of treating a disease in a subject comprising taking a measurement of a biomarker panel in a sample from the subject, and affecting a therapy with respect to the subject. The terms "therapy"

and "treatment" may be used interchangeably. In certain embodiments, the therapy can be selected from, without limitation, initiating therapy, continuing therapy, modifying therapy or ending therapy. A therapy also includes any prophylactic measures that may be taken to prevent disease.

In certain embodiments, treatment comprises administering a disease-modulating drug to a subject. The drug can be a therapeutic or prophylactic used in subjects diagnosed or identified with a disease or at risk of having the disease. In certain embodiments, modifying therapy refers to altering the duration, frequency or intensity of therapy, for example, altering dosage levels.

In various embodiments, effecting a therapy comprises causing a subject to or communicating to a subject the need to make a change in lifestyle, for example, increasing exercise, changing diet, reducing or eliminating smoking and so on. The therapy can also include surgery, for example, mastectomy.

Measurement of biomarker levels allow for the course of treatment of a disease to be monitored. The effectiveness of a treatment regimen for a disease can be monitored by detecting one or more biomarkers in an effective amount from samples obtained from a subject over time and comparing the amount of biomarkers detected. For example, a first sample can be obtained prior to the subject receiving treatment and one or more subsequent samples are taken after or during treatment of the subject. Changes in biomarker levels across the samples may provide an indication as to the effectiveness of the therapy.

To identify therapeutics or drugs that are appropriate for a specific subject, a test sample from the subject can also be exposed to a therapeutic agent or a drug, and the level of one or more biomarkers can be determined Biomarker levels can be compared to a sample derived from the subject before and after treatment or exposure to a therapeutic agent or a drug, or can be compared to samples derived from one or more subjects who have shown improvements relative to a disease as a result of such treatment or exposure. Thus, in one aspect, the invention provides a method of assessing the efficacy of a therapy with respect to a subject comprising taking a first measurement of a biomarker panel in a first sample from the subject; effecting the therapy with respect to the subject; taking a second measurement of the biomarker panel in a second sample from the subject and comparing the first and second measurements to assess the efficacy of the therapy.

Additionally, therapeutic or prophylactic agents suitable for administration to a particular subject can be identified by detecting a biomarker (which may be two or more) in an effective amount from a sample obtained from a subject and exposing the subject-derived sample to a test compound that determines the amount of the biomarker(s) in the subject-derived sample. Accordingly, treatments or therapeutic regimens for use in subjects having a disease or subjects at risk for developing a disease can be selected based on the amounts of biomarkers in samples obtained from the subjects and compared to a reference value. Two or more treatments or therapeutic regimens can be evaluated in parallel to determine which treatment or therapeutic regimen would be the most efficacious for use in a subject to delay onset, or slow progression of a disease. In various embodiments, a recommendation is made on whether to initiate or continue treatment of a disease.

Drug Treatments

In various exemplary embodiments, effecting a therapy comprises administering a disease-modulating drug to the subject. The subject may be treated with one or more disease-modulating drugs until altered levels of the measured biomarkers return to a baseline value measured in a population not suffering from the disease, experiencing a less severe stage or form of a disease or showing improvements in disease biomarkers as a result of treatment with a disease-modulating drug. Additionally, improvements related to a changed level of a biomarker or clinical parameter may be the result of treatment with a disease-modulating drug.

A number of compounds such as a disease-modulating drug may be used to treat a subject and to monitor progress using the methods of the invention. In certain embodiments, the disease-modulating drug comprises The beneficial effects of these and other drugs can be visualized by assessment of clinical and laboratory biomarkers.

Any drug or combination of drugs disclosed herein may be administered to a subject to treat a disease. The drugs herein can be formulated in any number of ways, often according to various known formulations in the art or as disclosed or referenced herein.

In various embodiments, any drug or combination of drugs disclosed herein is not administered to a subject to treat a disease. In these embodiments, the practitioner may refrain from administering the drug or combination of drugs, may recommend that the subject not be administered the drug or combination of drugs or may prevent the subject from being administered the drug or combination of drugs.

In various embodiments, one or more additional drugs may be optionally administered in addition to those that are recommended or have been administered. An additional drug will typically not be any drug that is not recommended or that should be avoided. In exemplary embodiments, one or more additional drugs comprise one or more glucose lowering drugs.

Decision Matrices

The therapy chosen by a practitioner can depend on the concentrations of biomarkers determined in a sample. In various exemplary embodiments, the therapy depends on which category from a range of categories particular to each biomarker the measured concentration of each biomarker falls in. In various exemplary embodiments, the therapy depends on the combination of risk levels for different symptoms or diseases that are indicated by a biomarker panel.

With respect to concentration measurements of a biomarker, the term "category" refers to a subset of a partition of the possible concentrations that a biomarker may have. Each category may be associated with a label or classification chosen by the practitioner. The labels may be refer to, for example, the risk level of an individual for having or being subject to a disease state. The categories and labels may be derived from the current literature or according to the findings of the practitioner.

Each biomarker of a biomarker panel can thus be associated with a discrete set of categories, for example, risk categories. Combining one category from each biomarker forms a "decision point." In various exemplary embodiments, the complete set of decision points comprises all possible n-tuples of categories, wherein n is the number of biomarkers in the biomarker panel. This complete set will have $m_1 \times m_2 \times \ldots m_n$ possible decision points, wherein $m_i$ is the number of categories for biomarker i.

Every decision point can be associated with a condition or a disease state, which is not necessarily unique. That is, one or more decision points can be associated with the same disease state. The association of every possible decision point with a condition or disease state can be referred to as a "disease classification matrix" or a "disease classification tree." Thus, by correlating a measurement of a biomarker panel with a decision point, the practitioner can classify the condition or disease state of a patient.

Every decision point can also be associated with a particular therapy, which is not necessarily unique. That is, one or more decision points can be associated with the same therapy. The association of every possible decision point with one or more therapies can be referred to as a "therapy decision matrix" or "therapy decision tree."

Each decision point can be associated with more than one type of information. For example, both disease state and therapy can be indicated by a decision point.

The articles "a," "an" and "the" as used herein do not exclude a plural number of the referent, unless context clearly dictates otherwise. The conjunction "or" is not mutually exclusive, unless context clearly dictates otherwise. The term "include" is used to refer to non-limiting examples.

EXAMPLES

The following examples are offered to illustrate, but not to limit the invention.

Example 1

Salivary Transciptomic Profiling and Analysis

Saliva Collection

Unstimulated whole saliva samples were collected with previously established protocols. Subjects were asked to refrain from eating, drinking, smoking, or oral hygiene procedures for at least 30 minutes before the collection. Lipstick was wiped off, and the subject rinsed her mouth once with plain water. Typically, patients donated approximately 5-10 ml of saliva. Samples were then centrifuged at 2,600 g for 15 minutes at 4° C. The supernatant was then stored at −80° C. until use. Of note, protease inhibitors cocktail, containing 1 μl aprotinin, 10 μl PMSF (phenylmethanesulfonyl fluoride) and 3 μl sodium orthovanadate (all from Sigma, St. Louis, Mo.) were added to each 1 ml saliva sample.

mRNA Isolation and Analysis

RNA was isolated from 330 μl of saliva supernatant using MagMax™ Viral RNA Isolation Kit (Ambion, Austin, Tex.). This process was automated using KingFisher® mL technology (Thermo Fisher Scientific, Waltham, Mass.), followed by TURBO™ DNase treatment (Ambion, Austin, Tex.) to remove contaminating DNA. 90 μl of extracted RNA (out of 100 μl) was concentrated to 11 μl and was linearly amplified using the RiboAmp® RNA Amplification kit (Molecular Devices, Sunnyvale, Calif.). After purification, cDNA was transcribed and biotinylated using GeneChip® Expression 3'-Amplification Reagents for in vitro transcription labeling (Affymetrix, Santa Clara, Calif.). Approximately 20 μg of labeled RNA were subsequently submitted for GeneChip® analysis using an Affymetrix Human Genome U133 Plus 2.0 Array. Chip hybridization and scanning were performed using the MIAME (Minimum Information About a Microarray Experiment) criteria. All Affymetrix Human Genome U133 Plus 2.0 Array data generated in this study were uploaded to the GEO database, accession number GSE20266.

Gene Array Statistical Analysis

The CEL files from all databases were imported into the statistical R 2.7.0 (hypertext transfer protocol://www.r-project.org) with samr and ROC packages. The Probe Logarithmic Intensity Error Estimation (PLIER) expression measures were computed after background correction and quantile normalization for each microarray dataset. Probeset-level quantile normalization was performed across all samples to make the effect sizes similar among all datasets. Finally, for every probeset, significance analysis of microarray (SAM) was applied to identify differential expression between the cancer and healthy control samples. The probesets were then ranked by the false discovery rate (FDR) corrected p-values.

Screening of Biomarker Candidates

The biomarker candidates generated by microarray profiling were subjected to further screening by real-time quantitative RT-PCR (qPCR) on the same set of samples used for the microarray analysis. To accomplish this, total RNA was reverse-transcribed using reverse transcriptase and gene-specific primers using the following thermal cycling conditions: 1 min at 60° C., 30 min at 50° C., 2 min at 95° C., followed by 15 cycles of 15 s at 95° C., 30 s at 50° C., 10 s at 72° C. These steps were followed with a final extension of 5 min at 72° C. and then cooling to 4° C. The preamplified product was cleaned using ExoSAP-IT (USB Corporation) and diluted 1/40 in water. 2 μl of the cDNA was used for qPCR.

qPCR was carried out in a 96-well plate in a reaction volume of 10 μl using power SYBR®-Green Master Mix (Applied Biosystems, Foster City, Calif.) for 15 min at 95° C. for initial denaturing, followed by 40 cycles of 95° C. for 30 s and 60° C. for 30 in the ABI 7500HT Fast Real Time PCR system (Applied Biosystems, Foster City, Calif.). All qPCRS were performed in duplicate for all candidate mRNA. The specificity of the PCR was confirmed according to the melting curve of each gene, and the average threshold cycle (Ct) was examined.

Amplicon lengths were around 100-130 bp for the outer primer pairs used in preamplification and 60-80 bp for the inner primer pairs used in qPCR. RT-qPCR primers were designed using Primer Express 3.0 software (Applied Biosystems, Foster City, Calif.). All primers were synthesized by Sigma-Genosys (Woodlands, Tex.), and the amplicons were intron spanning whenever possible.

Raw data were normalized by subtracting GAPDH Ct values from the biomarker Ct values to generate ΔCt. The Mann-Whitney rank sum test was used for between-group biomarker comparisons.

| Primers for 11 candidate biomarkers and GAPDH | | |
|---|---|---|
| Gene symbol | Primer name | Primer sequences (5'-3') |
| SEQ ID NO: 10 | ATXN3 ATXN3-OF | GAAAAACAGCAGCAAAAGCA |
| SEQ ID NO: 11 | ATXN3-IF | GGGGGACCTATCAGGACAGA |
| SEQ ID NO: 12 | ATXN3-IR | CAAGTGCTCCTGAACTGGTG |
| SEQ ID NO: 13 | ATXN3-OR | CCAAGTGCTCCTGAACTGGT |
| SEQ ID NO: 14 | GRIK1 GRIK1-OF | CCGGACTGGTCCTTTCTGTA |
| SEQ ID NO: 15 | GRIK1-IF | CCGGACTGGTCCTTTCTGTA |

Primers for 11 candidate biomarkers and GAPDH

| Gene symbol | Primer name | Primer sequences (5'-3') |
|---|---|---|
| SEQ ID NO: 16 | GRIK1-IR | AGCGTTGAAAGAGAGACACTG |
| SEQ ID NO: 17 | GRIK1-OR | CAGTGAGATTCCCAGTTCTTCC |
| SEQ ID NO: 18 | GRM1 GRM1-OF | GCAGGGAATGCCAATTCTAA |
| SEQ ID NO: 19 | GRM1-IF | TGGCAAGTCTGTGTCATGGT |
| SEQ ID NO: 20 | GRM1-IR | GCCACATATGCTGTCCCTTG |
| SEQ ID NO: 21 | GRM1-OR | GCCGTCTCATTGGTCTTCAC |
| SEQ ID NO: 22 | TPT1 TPT1-OF | TACCGTGAGGATGGTGTGAC |
| SEQ ID NO: 23 | TPT1-IF | CAAATGTGGCAATTATTTTGGA |
| SEQ ID NO: 24 | TPT1-IR | GATGACAAGCAGAAGCCAGTT |
| SEQ ID NO: 25 | TPT1-OR | GATGACAAGCAGAAGCCAGT |
| SEQ ID NO: 26 | RGS13 RGS13-OF | CTCACGGTGGAGCAGAATTT |
| SEQ ID NO: 27 | RGS13-IF | CTCACGGTGGAGCAGAATTT |
| SEQ ID NO: 28 | RGS13-IR | GGGACTGTGGCTGGATGTAA |
| SEQ ID NO: 29 | RGS13-OR | TGGGTTCCTGAATGTTCCTG |
| SEQ ID NO: 30 | S100A8 S100A8-OF | TCAGGAAAAGGGTGCAGAC |
| SEQ ID NO: 31 | S100A8-IF | TCAGGAAAAGGGTGCAGAC |
| SEQ ID NO: 32 | S100A8-IR | TGGAAGTTAACTGCACCATCA |
| SEQ ID NO: 33 | S100A8-OR | ACGCCCATCTTTATCACCAG |
| SEQ ID NO: 34 | CLDN15 CLDN15-OF | TTGTACCCCGGAACCAAGTA |
| SEQ ID NO: 35 | CLDN15-IF | CGGAACCAAGTACGAGCTG |
| SEQ ID NO: 36 | CLDN15-IR | CACCCAGGATGGAGATCAGT |
| SEQ ID NO: 37 | CLDN15-OR | CTGGGTCCTCGTCAGAGC |
| SEQ ID NO: 38 | IGF2BP1 IGF2BP1-OF | AGAATTTGACGGCAGCTGAG |
| SEQ ID NO: 39 | IGF2BP1-IF | CCAGGTCATCGTGAAAATCA |
| SEQ ID NO: 40 | IGF2BP1-IR | ATCTTCCGTTGAGCCATCTG |
| SEQ ID NO: 41 | IGF2BP1-OR | ATGTCTCGGATCTTCCGTTG |
| SEQ ID NO: 42 | CSTA CSTA-OF | ACGGAAAATTGGAAGCTGTG |
| SEQ ID NO: 43 | CSTA-IF | CATTAAGGTACGAGCAGGTGA |
| SEQ ID NO: 44 | CSTA-IR | TTTGTCCGGGAAGACTTTTG |
| SEQ ID NO: 45 | CSTA-OR | TTTGTCCGGGAAGACTTTTG |
| SEQ ID NO: 46 | MDM4 MDM4-OF | GTGGCAGTGTACTGAATGCAA |
| SEQ ID NO: 47 | MDM4-IF | TGGCAGTGTACTGAATGCAA |
| SEQ ID NO: 48 | MDM4-IR | AAGGCCCAACAACGAAAAC |
| SEQ ID NO: 49 | MDM4-OR | TCAGACGTGGAGAGAGAATGG |
| SEQ ID NO: 50 | H6PD H6PD-OF | GGCACAAGCTTCAGGTCTTC |
| SEQ ID NO: 51 | H6PD-IF | GTCGTGGGCCAGTACCAGT |
| SEQ ID NO: 52 | H6PD-IR | GTGGAAGCTGTCTGGCTTCT |
| SEQ ID NO: 53 | H6PD-OR | GTGGAAGCTGTCTGGCTTCT |
| SEQ ID NO: 54 | GAPDH GAPDH-OF | CATTGCCCTCAACGACCACTT |
| SEQ ID NO: 55 | GAPDH-IF | ACCACTTTGTCAAGCTCATTTCCT |
| SEQ ID NO: 56 | GAPDH-IR | CACCCTGTTGCTGTAGCCAAAT |
| SEQ ID NO: 57 | GAPDH-OR | ATGTGGGCCATGAGGTCCA |

OF = Outer forward,
IF = Inner forward,
IR = Inner reverse,
OR = Outer reverse.
All primers were designed using Primer Express 3.0 software (Applied Biosystems, FosterCity, CA).
The specificity of primers was checked using NCBI's GenBank BLAST search.

The data analysis for qPCR was performed using the $2^{-Ct}$ method, where GAPDH is used as the reference gene. The qPCR based gene expression values between two groups were compared using the non-parametric Wilcoxon test. To normalize for RNA input, qPCR was also performed for GAPDH. Raw data were normalized by subtracting GAPDH Ct values from the marker Ct values to provide ΔCt and then analyze with the stats, utilities packages from R 2.7.0 (world wide web.r-project.org) and the ROC package from Bioconductor 2.2 (world wide web.bioconductor.org). Statistical comparisons were made with the use of the Mann-Whitney U test with consideration of two different distributions for control and pancreatic cancer groups. Biomarkers that differentiated between groups of subjects (P value<0.05) were identified and compared by Area Under Curve (AUC) value. The AUC is based on constructing a receiver operating characteristic (ROC) curve which plots the sensitivity versus one minus the specificity. The AUC value is computed by numerical integration of the ROC curve. The range of this value can be 0.5 to 1.0. A value of 0.5 indicates that the biomarker is no better that a coin toss, while 1.0 indicates the relatively best diagnostic accuracy.

Example 2

Salivary Proteomic Profiling and Analysis

Protein Isolation and Analysis

Saliva from 13 healthy control subjects and 13 breast cancer subjects were centrifuged at 2600 g at 4° C. for 15 minutes. Saliva supernatant from the 13 health control subjects and 13 breast cancer subjects were pooled to form a control sample and a cancer sample for proteomic profiling. 250 μg of proteins in the pooled saliva samples were precipitated by methanol and then resuspended in 2-D cell lysis buffer (30 mM Tris-HCl, pH 8.8, containing 7M urea, 2M thiourea and 4% CHAPS detergent). The total proteins of each pooled sample, breast cancer and control, were labeled with the cyanine dyes Cy2 and Cy5 respectively. The two labeled sample sets were then combined and subjected to two-dimensional difference gel electrophoresis. After loading the labeled samples, isoelectric focusing (IEF) (pH3-10) was run following the protocol provided by Amersham BioSciences. The IPG strips were rinses in the SDS-gel running buffer before transferring to 13.5% SDS-gels. The SDS-gels were run at 15° C. until the dye front ran out of the gels. Gel images were scanned immediately following the SDS-PAGE using Typhoon TRIO™ (Amersham BioSciences). The fold change of the protein expression levels was obtained from in-gel DeCyder™ analysis.

Spots with fold changes larger than 1.5 on the gel were cut and then were washed multiple times to remove staining dye and other chemicals. Gel spots were dried to absorb maximum volume of digestion buffer. Dried 2D gel spots were rehydrated in digestion buffer containing sequencing grade modified trypsin (Promega, USA). Proteins were digested in-gel at 37° C. overnight. Digested peptides were extracted from the gel with TFA extraction buffer and with shaking. The digested tryptic peptides were desalted using C-18 Zip-tips (Millipore). The desalted peptides were mixed with CHCA matrix (α-cyano-4-hydroxycinnamic acid) and spotted into wells of a MALDI plate for MALDI-TOF MS (ABI4800) identification. Protein identification was based on peptide fingerprint mass mapping (using MS spectra) and peptide fragmentation mapping (using MS/MS spectra). Combined MS and MS/MS spectra were submitted for database search using GPS Explorer software equipped with the MASCOT search engine to identify proteins from primary sequence databases.

Screening of Biomarker Candidates

Four proteins (carbonic anhydrase VI, psoriasin, Transthyretin and Cyclophilin A) identified in the 2-D gel analysis (above) were subjected to Western blot analysis on the original sample set. Reduced protein samples (15 µg total protein per lane) were loaded onto a 10% bis-Tris gel and run at 150V in MES SDS running buffer for one hour. Pre-stained protein standard (Invitrogen) was used to track protein migration. The proteins were transferred to nitrocellulose membrane by using iBlot® (Invitrogen). The membrane was then washed in wash buffer containing 10 mM Tris-HCl, pH 7.6, 150 mM NaCl, and 0.1% (v/v) Tween®-20 (Sigma-Aldrich) before blocking for one hour in wash buffer containing 5% non-fat dry milk. After further washes in wash buffer, the membrane was incubated with primary antibody (mouse anti-human carbonic anhydrase VI (Lifespan Biotech) at 1 µg/ml, mouse anti-psoriasin (Abcam) at 1 µg/ml, mouse anti-actin (Sigma-Aldrich) at 1 µg/ml according to manufacturers instructions in blocking buffer at room temperature for 2 h. The membrane was then washed before applying the secondary antibody (anti-mouse IgG peroxidase-linked species specific whole antibody from sheep, GE Healthcare) according to manufacturer's instructions for one hour at room temperature. Finally, the membrane was washed and visualized using ECL Plus™ detection kit (GE Healthcare). The signal intensity of the bands was measured using Image J software (NIH, Bethesda, Md., USA). The intensity of a band representing the protein of interest was divided by the intensity of it corresponding β-actin expression on the same blot for normalization.

The protein expression pattern of carbonic anhydrase VI and psoriasin was further tested by Western blot with a new subject sample set including 31 cancer subject samples and 62 control subject samples. All the samples were coded with a random bumber from 1 to 93 and used for blind testing by Western blot. The distribution of carbonic anhydrase VI shows significant difference in the cancer group as compared to the control group (p=0.009949).

Example 4

Screening Method

A patient undergoing routine dental care is screened during the visit. For example, a 62 year old female patient, and former smoker, prior to oral exam is asked to provide a saliva sample. A saliva sample is collected and analyzed either at the point of care or is submitted for analysis by a reference laboratory. The saliva sample is tested for the biomarkers of the instant invention and optionally other biomarkers. Results from the analysis are provided to the dental professional and the patient is informed as to whether she has breast cancer.

(S100A8) (NM_002964.4)

SEQ ID NO: 1 gagaaaccag agactgtagc aactctggca gggagaagct gtctctgatg gcctgaagct gtgggcagct ggccaagcct aaccgctata aaaaggagct gcctctcagc cctgcatgtc tcttgtcagc tgtctttcag aagacctggt ggggcaagtc cgtgggcatc atgttgaccgagctggagaa agccttgaac tctatcatcg acgtctacca caagtactcc ctgataaagg ggaatttcca tgccgtctac agggatgacc tgaagaaatt gctagagacc gagtgtcctcagtatatcag gaaaaagggt gcagacgtct ggttcaaaga gttggatatc aacactgatg gtgcagttaa cttccaggag ttcctcattc tggtgataaa gatgggcgtg gcagcccaca aaaaaagcca tgaagaaagc cacaaagagt agctgagtta ctgggcccag aggctgggcc cctggacatg tacctgcaga ataataaagt catcaatacc tcaaaaaaaa aa (CSTA) (NM_005213)

SEQ ID NO: 2 tgctgtttgt ggaaaataaa gcattctata ggcggagcta gtgaacgcct cttttaaaacacgagtctcc acacttccct gttcactttg gttccagcat cctgtccagc aaagaagcaa tcagccaaaa tgatacctgg aggcttatct gaggccaaac ccgccactcc agaaatccag gagattgttg ataaggttaa accacagctt gaagaaaaaa caaatgagac ttacggaaaa ttggaagctg tgcagtataa aactcaagtt gttgctggaa caaattacta cattaaggta cgagcaggtg ataataaata tatgcacttg aaagtattca aaagtcttcc cggacaaaat gaggacttgg tacttactgg ataccaggtt gacaaaaaca aggatgacga gctgacgggc ttttagcagc atgtacccaa agtgttctga ttccttcaac tggctactga gtcatgatcc ttgctgataa atataaccat caataaagaa gcattcttt ccaaagaaat tatttcttca attatttctc atttattgta ttaagcagaa attacctttt ctttctcaaa atcagtgtta

```
                                -continued
ttgctttaga gtataaactc catataaatt gatggcaatt
ggaaatctta taaaaactag tcaagcctaa tgcaactggc
taaaggatag taccaccctc accccacca taggcaggct
ggatcgtgga ctatcaattc accagcctcc ttgttccctg
tggctgctga taacccaaca ttccatctct accctcatac
ttcaaaatta aatcaagtat tttacaaaaa aaaaaaaa
(GRM1)(NM_001114329)
                                        SEQ ID NO: 3
agtgctgaag aaagagggca ctagtgtaca gcccagatcg
catccttgca ccgtctggat tagagctgag gcgtctgcaa
gccgagcgtg gccacggtcc tctggcccng ggaccatagc
gctgtctacc ccgactcagg tactcagcag catctagctc
accgctgcca acacgacttc cactgtactc ttgatcaatt
taccttgatg cactaccggt gaagaacggg gactcgaatt
cccttacaaa cgcctccagc ttgtagaggc ggtcgtggag
gacccagagg aggagacgaa ggggaaggag gcggtggtgg
aggaggcaaa ggccttggac gaccattgtt ggcgaggggc
accactccgg gagaggcggc gctgggcgtt ttgggggtgc
gcgccgggag cctgcagcgg gaccagcgtg ggaacgcggc
tggcaggctg tggacctcgt cctcaccacc atggtcggc
tccttttgtt ttttttccca gcgatctttt tggaggtgtc
ccttctcccc agaagccccg gcaggaaagt gttgctggca
ggagcgtcgt ctcagcgctc ggtggccaga atggacggag
atgtcatcat ggagccctc ttctcagtcc atcaccagcc
tccggccgag aaagtgcccg agaggaagtg tggggagatc
agggagcagt atggcatcca gagggtggag gccatgttcc
acacgttgga taagatcaac gcggacccgg tcctcctgcc
caacatcacc ctgggcagtg agatccggga ctcctgctgg
cactcttccg tggctctgga acagagcatt gagttcatta
gggactctct gatttccatt cgagatgaga aggatgggat
caaccggtgt ctgcctgacg gccagtccct cccccaggc
aggactaaga agcccattgc gggagtgatc ggtcccggct
ccagctctgt agccattcaa gtgcagaacc tgctccagct
cttcgacatc ccccagatcg cttattcagc cacaagcatc
gacctgagtg acaaaacttt gtacaaatac ttcctgaggg
ttgtccccttc tgacactttg caggcaaggg ccatgcttga
catagtcaaa cgttacaatt ggaccctatgt ctctgcagtc
cacacggaag ggaattatgg ggagagcgga atggacgctt
tcaaagagct ggctgcccag gaaggcctct gtatcgccca
ttctgacaaa atctacagca acgctgggga aagagctttt
gaccgactct tgcgcaaact ccgagagagg cttcccaagg
ctagagtggt ggtctgcttc tgtgaaggca tgacagtgcg -continued
aggactcctg agcgccatgc ggcgccttgg cgtcgtgggc
gagttctcac tcattggaag tgatggatgg gcagacagag
atgaagtcat tgaaggttat gaggtggaag ccaacggggg
aatcacgata aagctgcagt ctccagaggt caggtcatttt
gatgattatt tcctgaaact gaggctggac actaacacga
ggaatccctg gttccctgag ttctgcaac atcggttcca
gtgccgcctt ccaggacacc ttctggaaaa tcccaacttt
aaacgaatct gcacaggcaa tgaaagctta gaagaaaact
atgtccagga cagtaagatg gggtttgtca tcaatgccat
ctatgccatg gcacatgggc tgcagaacat gaccatgcc
ctctgccctg gccacgtggg cctctgcgat gccatgaagc
ccatcgacgg cagcaagctg ctggacttcc tcatcaagtc
ctcattcatt ggagtatctg gagaggaggt gtggtttgat
gagaaaggag acgctcctgg aagtatgat atcatgaatc
tgcagtacac tgaagctaat cgctatgact atgtgcacgt
tggaacctgg catgaaggag tgctgaacat tgatgattac
aaaatccaga tgaacaagag tggagtggtg cggtctgtgt
gcagtgagcc ttgcttaaag ggccagatta aggttatacg
gaaaggagaa gtgagctgct gctggatttg cacggcctgc
aaagagaatg aatatgtgca agatgagttc acctgcaaag
cttgtgactt gggatggtgg cccaatgcag atctaacagg
ctgtgagccc attcctgtgc gctatcttga gtggagcaac
atcgaatcca ttatagccat cgccttttca tgcctgggaa
tccttgttac cttgtttgtc accctaatct ttgtactgta
ccgggacaca ccagtggtca atcctccag tcgggagctc
tgctacatca tcctagctgg catcttcctt ggttatgtgt
gcccattcac tctcattgcc aaacctacta ccacctcctg
ctacctccag cgcctcttgg ttggcctctc ctctgcgatg
tgctactctg ctttagtgac taaaaccaat cgtattgcac
gcatcctggc tggcagcaag aagaagatct gcacccggaa
gcccaggttc atgagtgcct gggctcaggt gatcattgcc
tcaattctga ttagtgtgca actaaccctg gtggtaaccc
tgatcatcat ggaaccccct atgcccattc gtcctaccc
aagtatcaag gaagtctacc ttatctgcaa taccagcaac
ctgggtgtgg tggccccttt gggctacaat ggactcctca
tcatgagctg tacctactat gccttcaaga cccgcaacgt
gcccgccaac ttcaacgagg ccaaatatat cgcgttcacc
atgtacacca cctgtatcat ctggctagct tttgtgccca
tttactttgg gagcaactac aagatcatca aacttgctt
tgcagtgagt ctcagtgtaa cagtggctct ggggtgcatg
ttcactccca agatgtacat cattattgcc aagcctgaga
```

-continued

```
ggaatgtccg cagtgccttc accacctctg atgttgtccg
catgcatgtt ggcgatggca agctgccctg ccgctccaac
actttcctca acatcttccg aagaaagaag gcaggggcag
ggaatgccaa gaagaggcag ccagaattct cgcccaccag
ccaatgtccg tcggcacatg tgcagctttg aaaaccccca
cactgcagtg aatgtttcta atggcaagtc tgtgtcatgg
tctgaaccag gtggaggaca ggtgcccaag ggacagcata
tgtggcaccg cctctctgtg cacgtgaaga ccaatgagac
ggcctgcaac caaacagccg tcatcaagcc cctcactaaa
agttaccaag gctctggcaa gagcctgacc ttttcagata
ccagcaccaa gacccttac aacgtagagg aggaggagga
tgcccagccg attcgcttta gcccgcctgg tagccttcc
atggtggtgc acaggcgcgt gccaagcgcg cgaccactc
cgcctctgcc gtcccacctg accgcagagg agacccccct
cttcctggcc gaaccagccc tccccaaggg cttgcccct
cctctccagc agcagcagca accccctcca cagcagaaat
cgctgatgga ccagctccag ggagtggtca gcaacttcag
taccgcgatc ccggattttc acgcggtgct ggcaggcccc
ggtggtcccg gaacgggct gcggtccctg tacccgcccc
cgccacctcc gcagcacctg cagatgctgc cgctgcagct
gagcaccttt ggggaggagc tggtctcccc gcccgcggac
gacgacgacg acagcgagag gtttaagctc ctccaggagt
acgtgtatga gcacgagcgg gaagggaaca cggaagaaga
cgaactggaa gaggaggagg aggacctgca ggcggccagc
aaactgaccc cggatgattc gcctgcgctg acgcctccgt
cgcctttccg cgactcggtg gcctcgggca gctcggtgcc
cagctccccc gtgtccgagt cggtgctctg caccctccc
aacgtatcct acgcctctgt cattctgcgg gactacaagc
aaagctcttc caccctgtaa ggggaaggg tccacataga
aaagcaagac aagccagaga tctcccacac ctccagagat
gtgcaaacag ctgggaggaa agcctggga gtgggggcc
tcgtcgggag gacaggagac cgctgctgct gctgccgcta
ctgctgctgc tgccttaagt aggaagagag ttaattacac
caagcaaaaa atgttccagg ccaggattcg gattcttgaa
ttactcgaag ccttctctgg gaagaaaggg aattctgaca
aagcacaatt ccatatggta tgtaactttt atcacaaatc
aaatagtgac atcacaaaca taatgtcctc ttttgcacaa
ttgtgcatag atatatatat gcccacacac actgggccat
gcttgccaag gaacagccca cgtggacatg ccagtcgat
catgagttca cctgatggca ttcgagtga gctggtggag
ccagacagag caggtgcggg gaagggaagg gcccaggcca
```

-continued

```
gcccaggcca gacccatccc aaacgatga tgggatgatg
ggacagcagc tccttgctca gaagccttc tccccgctgg
gctgacagac tcctcatctt caggagactc aggaatggag
cggcacaggg gtctctcttc atccactgca acccatccag
tgccagcttt gagattgcac ttgaagaaag gtgcatggac
cccctgctgc tctgcagatt ccctttattt aggaaaacag
gaataagagc aaaattatca ccaaaaagtg cttcatcagg
cgtgctacag gaggaaggag ctagaaatag aacaatccat
cagcatgaga ctttgaaaaa aaaacacatg atcagcttct
catgttccat attcacttat tggcgatttg gggaaaaggc
cggaacaaga gattgttacg agagtggcag aaaccctttt
gtagattgac ttgtgtttgt gccaagcggg ctttccattg
accttcagtt aaagaacaaa ccatgtgaca aaattgttac
cttccactta ctgtagcaaa taatacctac aagttgaact
tctaagatgc gtatatgtac aatttggtgc cattatttct
cctacgtatt agagaaacaa atccatcttt gaatctaatg
gtgtactcat agcaactatt actggtttaa atgacaaata
attctatcct attgtcactg aagtccttgt aactagcgag
tgaatgtgtt cctgtgtcct tgtatatgtg cgatcgtaaa
atttgtgcaa tgtaatgtca aattgactgg tcaatgtcaa
cctagtagtc aatctaactg caattagaaa ttgtcttttg
aatatactat atatatttt tatgttccaa taatgttttg
tacatcattg tcatcaatat ctacagaagc tctttgacgg
tttgaatact atggctcaag gttttcatat gcagctcgga
tggacatttt tcttctaaga tggaacttat ttttcagata
ttttctgatg tggagatatg ttattaatga agtggtttga
aaatttgtta tattaaaagt gcacaaaaac tgagagtgaa
aataaaaggt acattttata agcttgcaca cattattaac
acataagatt gaacaaagca tttagattat tccaggttat
atcatttttt taaagatttt ccacagctac ttgagtgtct
aacatacagt aacatctaac tcagctaata atttgtaaaa
tctttatcaa tcacattttg ccttcttta attttatgt
tcatggactt ttattcctgt gtcttggctg tcataacttt
ttatttctgc tatttgctgt tgtgtaatat ccatggacat
gtaatccact tactccatct ttacaatccc tttttaccac
caataaaagg attttttcttg ctgttttgat ttcttctatt
atttgtggaa tgaattatac ccccttaaa tatctttgtt
tatgccttat gttcagtcat attttaatat gcttcctca
tattgaagct gctgatttct cagccaaaaa tcatcttaga
atctttaaat atccattgca tcatttgttc agaatttaac
atccattcca atgttggagg cttgtattac ttatatttca
```

-continued

```
tcatattcta ttgccaagtt tagtcagttc cacaccaaga
atgaactgca tttcctttaa aaattatttt aaaacacctt
tattgaaaag atctcatgac tgagatgtgg actttggttc
catgttttca ttgtaagaaa gcagagagcg gaaaatcaat
ggctccagtg attaatagat gggttttttag taattgacaa
attcatgagg gaaagcatat gatctcttta ttagtgaatc
atgcttattt tttactctta atgccactaa tatacatccc
taatatcaca gggcttgtgc attcagattt ttaaaaaatt
aggatagata aggaaacaac ttatattcaa gtgtaagatg
atatcaggtt ggtctaagac ttttggtgaa cacgttcatt
caactgtgat cactttatta ctctgaatgc ctactattat
cctgattatg gggtctcctg aataaataga gtattagtcc
ttatgtcatc attgttcaaa attggagatg tacacataca
tacccatac caagagggcc gaaactcttc accttgatgt
atgttctgat acaagttgtt cagcttcttg taaatgtgtt
ttccttcggc ttgttactgc cttttgtcaa ataatcttga
caatgctgta taataaatat tttctattt
```

(TPT1) (NM_003295.2)
SEQ ID NO: 4

```
ccccccgagc gccgctccgg ctgcaccgcg ctcgctccga
gtttcaggct cgtgctaagctagcgccgtc gtcgtctccc
ttcagtcgcc atcatgatta tctaccggga cctcatcagc
cacgatgaga tgttctccga catctacaag atccgggaga
tcgcggacgg gttgtgcctg gaggtggagg ggaagatggt
cagtaggaca gaaggtaaca ttgatgactc gctcattggt
ggaaatgcct ccgctgaagg cccccgagggc gaaggtaccg
aaagcacagt aatcactggt gtcgatattg tcatgaacca
tcacctgcag gaaacaagtt cacaaaaga agcctacaag
aagtacatca agattacat gaaatcaatc aaagggaaac
ttgaagaaca gagaccagaa agagtaaaac cttttatgac
aggggctgca gaacaaatca agcacatcct tgctaatttc
aaaaaactacc agttctttat tggtgaaaac atgaatccag
atggcatggt tgctctattg gactaccgtg aggatggtgt
gaccccatat atgatttct ttaaggatgg tttagaaatg
gaaaaatgtt aacaaatgtg gcaattattt tggatctatc
acctgtcatc ataactggct tctgcttgtc atccacacaa
caccaggact taagacaaat gggactgatg tcatcttgag
ctcttcattt attttgactg tgatttatt ggagtggagg
cattgttttt aagaaaaaca tgtcatgtag gttgtctaaa
aataaaatgc atttaaactc atttgagag
```

(GRIK1)
(NM_000830.3; mRNA variant 1 of 2 shown)
SEQ ID NO: 5

```
agagccctg caccaactca ccctgtaccc tctctccttc
ttcgttagtc ttctttcccc cttttccctc ctctgtctgt
gcctatcccc cgacttttgc atctgaccaa aggacgaatg
agggagacgt tcctgcagat cggggcagca actttcctca
gctggtctct gggctccggg agccagagag cgctgatcct
ccgcggtctg cggcccatgg aagaggagga ggaggagccg
tgatgggcta gcgacagcac tgaggagccc cgagagagct
cagccttgcc agccagctcc gcggtcccac gcgggttccc
tcgagctcgc tccgtgggga gcgcgcagcg tgcttggaac
cggagcatcc agagaggatg aggcggggac ccggcccaag
ttgggtgcat ctctcgggcg tccggcagcg gctgtatctc
ggcatgaatt aagaagctag gaagatggag cacggcacac
tcctcgccca gcccgggctc tggaccaggg acaccagctg
ggcactcctc tatttcctct gctatatcct ccctcagacc
gccccgcaag tactcaggat cggagggatt tttgaaacag
tggaaaatga gcctgttaat gttgaagaat tagctttcaa
gtttgcagtc accagcatta acagaaaccg aaccctgatg
cctaacacca cattaaccta tgacatccag agaattaacc
tttttgatag ttttgaagcc tcgcggagag catgtgacca
gctggctctt ggtgtggctg ctctctttgg cccttcccat
agctcctccg tcagtgctgt gcagtctatt tgcaatgctc
tcgaagttcc acacatacag acccgctgga acacccctc
ggtggacaac aaagatttgt tttacatcaa cctttaccca
gattatgcag ctatcagcag ggcgatcctg gatctggtcc
tctattacaa ctggaaaaca gtgacagtgg tgtatgaaga
cagcacaggt ctaattcgtc tacaagagct catcaaagct
ccctccagat ataatattaa aatcaaaatc cgccagctgc
cctctgggaa taaagatgcc aagcctttac tcaaggagat
gaagaaaggc aaggagttct atgtgatatt tgattgttca
catgaaacag ccgctgaaat ccttaagcag attctgttca
tgggcatgat gaccgagtac tatcactact ttttcacaac
cctggactta tttgctttgg atctggaact ctataggtac
agtggcgtaa acatgaccgg gtttcggctg cttaacattg
acaaccctca cgtgtcatcc atcattgaga agtggtccat
ggagagactg caggcccac ccaggcccga gactggcctt
ttggatggca tgatgacaac tgaagcggct ctgatgtacg
atgctgtgta catggtggcc attgcctcgc accgggcatc
ccagctgacc gtcagctccc tgcagtgcca tagacataag
ccatggcgcc tcggacccag atttatgaac ctgatcaaag
```

-continued

```
aggcccggtg ggatggcttg actgggcata tcacctttaa
taaaaccaat ggcttgagga aggattttga tctggacatt
attagtctca aagaggaagg aactgaaaag gctgctggcg
aagtgtctaa acacttgtat aaagtgtgga agaagattgg
gatttggaat tccaacagtg ggcttaacat gacggacagc
aacaaagaca agtccagcaa tatcactgat tcattggcca
acagaacact cattgtcacc accattctgg aagaaccccta
tgttatgtac aggaaatctg ataagcctct atatggaaat
gacagatttg aaggatattg cctagacctg ttgaaagaat
tgtcaaacat cctgggtttc atttatgatg ttaaactagt
tcccgatggc aaatatgggg cccagaatga caaaggggag
tggaacggga tggttaaaga actcatagat cacagggctg
acctggcagt ggctcctctt accatcacct acgtgcggaa
gaaagtcatt gacttctcca aaccccttcat gaccctaggc
atcagcattc tctaccggaa gcccaatggt accaatccag
gcgttttctc cttcctcaac ccccctgtctc cagatatttg
gatgtatgtg ctcttagcct gcttgggagt cagctgtgta
ctctttgtga ttgcaaggtt tacaccctac gagtggtata
accccccaccc atgcaaccct gactcagacg tggtgaaaaa
caatttttact ttactaaata gtttctggtt tggagttgga
gctctcatgc agcaaggatc agagctgatg cccaaagctc
tatcgaccag aatagttgga gggatatggt ggtttttcac
cctaatcatc atttcatcct acacggccaa tctggctgcc
ttcttgacag tagagagaat ggaatccccc atagattcgg
cagatgatct ggcaaagcaa accaagatag aatatggggc
ggttagagat ggatcaacaa tgaccttctt caagaaatca
aaaatctcca cctatgagaa gatgtgggct ttcatgagca
gcaggcagca gaccgccctg gtaagaaaca gtgatgaggg
gatccagaga gtgctcacca cagactacgc gctgctgatg
gagtccacca gcattgagta tgtgacgcag agaaactgca
acctcactca gatcggggc ctcattgact ccaaaggtta
cggagtggga acacctattg gttctcctta ccgggataaa
attactattg ctattcttca actccaagaa gaagggaagc
tgcatatgat gaaagagaag tggtggcgtg ggaatggctg
ccccgaggaa gacaacaaag aagccagtgc cctgggagtg
gaaaatattg gaggcatctt cattgttctg gctgccggac
tggtcctttc tgtatttgta gctattggag aattcatata
caaatcacgg aagaataatg atattgaaca ggcttttttgt
ttcttttatg gactgcaatg taagcaaacc catccaacca
actccacttc tggaactact ttatctacgg atttagaatg
```

```
tggtaaatta attcgagagg agagagggat tcgaaaacag
tcctcagttc atactgtgta atcagtttaa a
```

(H6PD) (NM_004285)

SEQ ID NO: 6

```
tgaggcctga ggcctggggc ggggtggcgg ccgggctggc
cttggcctcg cgccttcccc tgcggccgcc gcgggctccg
cgggcggtat cggagtgtcg tgcggcgcgt ggccgcgtga
cacgcgcact tgtcggagtg acgggccctg cggaagagga
ggtgcggccc agggcgcagg ggagccctcg ggagcgggcc
cggccctcag cgccgccccg gccgtgtccc ggaggagcgg
cctgcgccgc gcgcgcgagag aagcaccca ggcatgtgga
atatgctcat agtggcgatg tgcttggccc ttctgggctg
cctgcaagcc caggagctcc agggacatgt ctccataatc
ctgctgggag caactggggga cctggctaag aagtacttat
ggcagggact gttccagctg tacctggatg aagcggggag
gggtcacagt tttagcttcc atggagctgc tctgacagcc
ccaagcagg gtcaagagct catggccaag gccctggaat
ccctctcctg ccccaaggac tggcaccca gtcactgtgc
agagcacaag gatcagttcc tgcagctgag ccagtaccgc
aactgaaga cggccgagga ctatcaggcc ctgaacaagg
acatcgaggc acagctccag acgcaggcc tccgggaggc
tggcaggatc ttctacttct cagtgccacc cttcgcctat
aagacattg cccgcaacat caacagtagc tgccggccag
gcccgggcgc ctggctgcgg ttgtccttg agaaacccctt
tggccatgac cacttctcag cccagcagct ggccacagaa
tcgggaccct tttttccagga ggaggagatg taccggggtgg
accattactt aggcaagcag ctgtggcgc agatcctgcc
tttccgagac cagaaccgca aggctttgga cggctctgg
accggcacc atgtgagcg ggtggagatc atcatgaaag
agaccgtgga tgctgaaggc gcaccagct tctatgagga
gtacggtgtc attcgcgacg tcctccagaa ccatctgacg
aggtcctca ccctcgtggc catggagctg ccccacaatg
tcagcagtgc ggaggctgtg ctgcggcaca gcttcaggt
cttccaggcg ctgcggggcc tgcagagggg cagtgccgtc
tgggccagt accagtctta cagtgagcag gtgcgcagag
agctgcagaa gccagacagc tccacagcc tgacgccgac
cttcgcagcc gtcctagtgc acattgacaa ccttcgctgg
agggcgtgc ctttcatcct gatgtctggc aaagccttgg
acgagagagt gggctacgct ggatcttgt tcaagaacca
ggcctgctgt gtgcagagcg aaaagcactg gccgcggcg
agagccagt gcctgccccg gcagctcgtc ttccacatcg
gccatggcga cctgggcagc ctgccgtgc tggtcagcag
```

```
gaacctgttc aggccctccc tgccctccag ctggaaggaa
tggagggac cacctgggct ccgccttttc ggcagccctc
tgtccgatta ctacgcctac gccctgtgc gggagcggga
cgcccactcc gtcctcttat cccatatctt ccatggccgg
agaatttct tcatcaccac agagaacttg ctggcctcct
ggaacttctg gacccctctg tggagagcc tggcccataa
ggccccacgc tctaccctg gaggagctga aatggccgt
ctgttggact ttgagttcag tagcggccgg ttgttcttt
cccagcagca gccggagcagctggtgccag ggccagggcc
ggccccaatg cccagtgact tccaggtcct cagggccaag
taccgagaga gcccgctggt ctccgcctgg tccgaggagc
tgatctctaa gctggctaat gacatcgagg ccaccgctgt
gcgagccgtg cggcgctttg gccagttcca cctggcactg
tcgggggct cgagccccgt ggccctgttc cagcagctgg
ccacggcgca ctatggcttc ccctgggcc acacgcacct
gtggctggtt gacgagcgct gcgtcccact ctcagacccg
gagtccaact tccagggcct gcaggcccac ctgctgcagc
acgtccggat cccctactac aacatccacc ccatgcctgt
gcacctgcag cagcggctct gcgccgagga ggaccagggc
gcccagatct atgccaggga gatctcagcc ctggtggcca
acagcagctt cgacctggtg ctgctgggca tgggtgccga
cgggcacaca gcctccctct tcccacagtc acccactggc
ctggatggcg agcagctggt cgtgctgacc acgagcccct
cccagccaca ccgccgcatg agccttagcc tgcctctcat
caaccgcgcc aagaaggtgg cagtcctggt catgggcagg
atgaagcgtg agatcaccac gctggtgagc cgggtgggcc
atgagcccaa gaagtggccc atctcgggtg tcctgccgca
ctccggccag ctggtgtggt acatggacta cgacgccttc
ctgggatgag ggcgcctgtg ccccttgccc gcttcgctcc
tgtgctttcc ttcgcccgtg tcttccctcc cttctcggcc
ccgccacctg cccagcgtgc cctggctctc cagaaccttc
tatcccacag tcaggcccca gagagggcag gacaagcctt
gtcccgatgc ctttgaccgg cagctctgtg tattggtgga
tagatgcaga aacaaggaag aaatggagtc tgctcctgag
aagcttcaaa ttcaggccag gagagaagtc ttaagaaaag
acctccagca gttacacatt catatcaacc agcacaacac
gggatggcgc ccaaactccg gcgttcacaa gaggagacgt
gacgtggtgg gctgaggtta atcagggaag gtttcctggg
ggaggtgatc cttgaactgg ctcccgggga acattcagag
catgattggt agacagaagg gtgcagaggc gcccagggga
gtacattgcc ccgtgcaaag caggggcatt ggggactgtc
```

```
ttgagaccct gagggggtca agccctcct tccccagctg
cccctccttc tagaacctct gcacatctag cctctggccc
tcctcttcac tgcctccacc tgctcccgct tgccatccct
gtctcctcca tcctggctgt gcagtaggaa ttccaggctc
ctccctgtgt ctttgctgtt cttcagactc catttataga
gaatgagggc tgataacagg aatacagtgg caaagactag
actgtggaaa gggttccaga aatcttttt cttttttaat
taaaaaaat atttgcagag atgagctctt gctatgttgc
ccaggctggt ctcaaactcc tgggctcaag cgatcctccc
atctcagcct cccagagtgc tgggattaca ggtgtgagct
actgcgccca gccccagaaa tctcagtgct gtttggagct
ccatttctca tttgatgact tgctctgcgt ggggaggtgg
ggtctcattc ccccaacttc ctcaggagg acccctgccc
tccgctgctc ctctgtcctg ctagccttcc tccaggaagc
acactgggtg cagataatca ggacattcca gagatcccca
atttaagagg gtcatttcca tctcagggga ctcccggatg
ggtgtttccg ctctcaatag cccctcttgt tttaccagga
aagatccagt taaatcaccc actgaggtga cagctcatta
gcggggagag agatggagca tcgagtgaca ctgggccatc
caggcggctc tgctcccacc agacaggagc taggcctcac
tggcagggg gctgcccaca gccttttcag gggctcgctt
ggcgggtgac ggggccgcag ccaggccttc tctccctgcc
ccttggtgac cccgtggctt cctgtctgct ggcctctcct
gctacttatc acttcaccac gaactctctg cctgagactg
gggaagtaag cgggtatctt ctcagtgagc ataggttggg
gactgtgatc ttgagaagcc atgggccagc aatacctgct
tttctgaagc ccccaaggag ggctctgaca ttcttttaa
aaacaccaca aagcaaaatt cccaggacat gtgtagtttt
gtttgttcag tatcccacaa cttaaggctg ggagatggaa
ctcttggtta aggtcgattt ttctgtctgg cttctccgca
ccttccactt gctctctgga tcaggcagat ataaactttc
tagcgcattt tgagagaggg ctttcttggg tgaggagca
tggcaaagtc ggtttctctc tggactgttt acacttcaag
gcggtggatt tagaggaatc ctggctttca ttttcaatgc
cagtctgaga catgttccca agccggggct cttgttcaca
ccacttactc tggccaccaa caacaaccca ggccagacag
agcatctctt ttttttttt ttgagacaga gtctctgtcg
cccaggctgg agcccagtgg cgagatcttg gctcactaca
acctccacct cccgggttca ggcaattctc gtgcctaagc
ctcccgagta gctgcgacta caggcgccgg ccagcatgcc
tgtctaattt ttgtatttta gtagagacag ggtttcacca
```

-continued

```
tgttgcccag gctggtctcg aactcctgag ctcaggcagt
ctacccacct cagcctccca agtgctggg attacaggcg
tgagccaccg cgcccagcca gaacatctgt ttttacaccc
agagagcgcc cctcgttagg acagaaccac ggtgcccaga
gccaggaagc cgccctcctg gcgcccagca tctgagcttc
tacacgtgat gggcgggctc aggagaggag agggagtcgt
ggtggaagtt ccacagctgg ccgcgtgggg gggcccttgc
accgcactgc cgcctcctga ctgcccctat ccccgcagcc
cctgtgccgg atttcatttc cctcctctct cccagggtac
ctggcccag cactctccca tctgttcttc aggaaccgac
tcctctccag ttgcaacacc agggagaaag gggcctccac
atgcccaagt accccctgcag gatgaagggc aggccggccc
ttgatgtgcc atttctgaat aatagtcact gccgccgagt
ctaggatgtc ctgttctaac tcagccctgc ctcggatgca
ccaccgatct gtgcagagtg ggtgtgggag tgtgggtgag
ggtcgaaatg ccaaaggtct actttccaga atcaagtgcc
ttctgcaaat catgttggaa aagtccaaac ctggagatgt
ccctgtgcct ccgcccctac ccacccctttt ccttcagct
gtgttaggaa ggagaagttt tcagaaccct ctaggctggt
ggctttcaaa cttcagacca gatctgcag caagaaacgt
gccttccatc ataaatcagt ccatttgttt acaactgtgt
ccaagcagg tttcataaag aaattcttaa ccttagaacc
tcggatatcc tctatgtttt agttttcatt tttttaaaat
gcttcttaaa attcactaaa ttgggctagg tgtggctcat
gcctgtaatc ccagcactat gggaggctga ggtgagga
tcacttgagc ccagaaggtt gaaaccagcc tgggcaacat
agtgagaccc catctctaca aaaagttttta aaaccaggta
tggtggtgcc ctcctgtggt cccagctact cgggagtctg
aggtgggagg atcacctgag cccaggagac tgaggctgca
gtaaggtgtg attgcactat tgctctctag cctggaaaac
agagtgagac cctatctcaa aaaaaaaaaa aaaaaaaag
gaaagagtga tgacaacagc ccagggagca gccccgctca
gaacccaagt cccagttcc agcactgtgt tcccaggcag
gctgtttgcc tcttcctggt ctggaagccc ttgggtccta
tggtggcggc agctcccaca tccaggttc cctggtgggg
accaatgatt ccatccgcat ggaagccac gtgtgcactt
agggggccat aaatggcaga agggcccctc ctttgggaga
ccttgtcagt cagcatctct agggcaaccg tgattgccat
ttgtagaggg gaaggaatca agggacttta agctagatca
aaatctggg acaaattctc ctgctaactg caagttaaaa
taggcccttc ttactgaatt tccctgtttg tttctctgca
```

-continued

```
gacaatgctt cttgggcccc caagttagca gagtaatcaa
agcttcctac cgttggcct actattccag actagtccct
cgaggggttc ccttccaaaa tatgcagggc tcaggctccc
aattccgggc ctgtctgctt tgcttgtgtt tctcctgtcc
ctgttctccc ggagggccca ggtggaactc acgacaggga
gggagacgct tcccaaaaac ctgcagggct atttcccaga
atttggtttt caagtacaaa acttttttgtc ctgtaagata
tatgcagcct cacagaagca gcctctgcct ccactttacc
agctacgttt ttatcttaag cacatggggc tcccttagaa
cttactccac tgatttaaaa aaaaaaaact gcctggcagc
atctcagtgt cagagtgagc acggcacagg aaaggcccgt
ggtgacgagg gtgaggtggc cacagtgacc ggacgacaaa
tgagactctg caaatgagac tccagagggt gaagatctgc
ggtctccaga catcataggc catgtgaccc actaggggcc
gcttacccct ggccgtccgc tggctgaact gaacgcattc
cctctctccg caactctccc gtgaggctgc acccgtgtgg
gtagcactgg aagcggcact gtttgcattg tacataggaa
ggaaggaagt tcttccagcc tcaccagcac ctggcagcga
tgcagagcct tgtagggcat ccgaagcagt gatgcagtgt
caacctccca tctggtgcca ctctgccctc gggggctcca
agcattgtaa ctcagtcatg ggagctgcct ctttggaagt
gcagatttat tcctgtaata atcctgcctf cttttacctc
tcgtccactg accagcaagt gtgagtcccg gtgtcagtcg
gcacagtcca gtgtccatct gcatttgctc atgcagaggg
ggtgagttgg gcactccctg ttgttggttt tccttttgca
gcacactggg cagtctccct ataaaacaaa aaccccacct
tctgtgcctt ctgctttaga gcagagctcc ccctcccatt
tcctcagtct tccctgcaaa atctgtccac cggggaaggc
agcaggaacc ctgggcagcg ggtgttctgg gaaggctagt
gacagcagat gtcatccagg aacagccaca cacggttctc
caggccgccg tcagcagctc aaggtggggt atgagtgaga
agctgaggat ctcgcagctt gttgctgagc aaggtgcaac
cgggctcatg ctgtcatcag cacaagacgg gatggcaagg
gctttcagac gcatttccaa gagtccagca agccaggggg
aagatgatcc ctttgccgaa gtgtaccctc tagccaactt
ttgggagcgc ttctgtttgc aaagcgctgg ggatgtgcct
gtctctgtgt gacccacgaa cgggaaggga gagcactgga
gtaatgacac ttctgctgct gcttttgattc tcaaggctga
tcttttaaaac cctcgccttg ctgacaggtg ctttaaaggc
agtctgcatc ttttcttccc ttggtgtggg agaggtaaac
actttgattt gctgaaagct gtatggagta tatttgaaca
```

```
gctagtagtt agctttgaaa gtggaagtgt gaacagacac
tacttgtgtc gctttgggtc cttcactttta cccccacaga
agtctagagg cgtctgttat aaagcgttac ggggcgcctg
catgcaggag gaaggacctg tattagctgg aaatcatcag
gaacccagct tgcctccatc tctctgagat gtgctgggta
cagcctgccc ctcctagttc tgtccaccgg gaagagccgg
ctggcggcag atcccaggg gcagagcccc tgctggatcc
tgggagctca tctttacctg tgccggagtg ggaactgtga
ttccagccgg gcaggtcaga gtggagcagt gctaagaggc
tgttgcagga gaactagacg ggcgggccct gctgcatctg
gatcatgttt ctgtgctctg ccccgcgcta gggactcagg
gtctgggctt ctgccaggtg aggagcagag agactgttcc
cttgggtgga gaggtgtggg catgagagcc acccattgcc
aagcagcaag aatgttcgtg ctttttttcca gagaggggaa
ccccactggt ttttgtggaa acaatgaaa cttacagatg
cctgcctggg atgatgaggc acattcagaa caaatgcttt
ttttttttttg agacagagtc tcgctctgac gcccaggctg
gagtgcagtg gcgcgatctc ggctcactgc aaactttgcc
tcccaggttc aagtgattct cctacctcag cctcccgagt
agctgggatt acaccaccat gcccagcaaa ttttttgtgtt
tttagtagag acggagtttc accatgttgg ccaggctggt
ctcgaactcc tgacctcagg tgatccatcc gccttggcct
cccaaagtgc tgggattaca ggcgggagcc accatgcctg
gccagaacaa atgcttttt aaaccttta agaacatttt
taaaatgtct ttttctatgt caaatgtaac gttttattttt
ttaaacaata aaattgattt gccaaaa
(IGF2BP1)(NM_001160423.1 version 1 of two
mRNA speies)
                                          SEQ ID NO: 7
atttagaggc ggcgccaggg cggccgcgga gaaacgtgac
acaccagccc tctcggaggg gtttcggacc gaagggaaga
agctgcgccg tgtcgtccgt ctccctgcgc gccgcgggca
cttctcctgg gctctccccg aactctcccg cgacctctgc
gcgccctcag gccgccttcc ccgccctggg ctcgggacaa
cttctggggt ggggtgcaaa gaaagtttgc ggctcctgcc
gccggcctct ccgcctcttg gcctaggagg ctcgccgccc
gcgcccgctc gttcggcctt gcccgggacc gcgtcctgcc
ccgagaccgc caccatgaac aagctttaca tcgcaacct
caacgagagc gtgaccccg cggacttgga gaaagtgttt
gcggagcaca agatctccta cagcggccag ttcttggtca
aatccggcta cgccttcgtg gactgccgg acgagcactg
ggcgatgaag gccatcgaaa cttttctccgg gaaagtagaa
```

```
ttacaaggaa aacgcttaga gattgaacat tcggtgccca
aaaaacaaag gagccggaaa attcaaatcc gaaatattcc
accccagctc cgatgggaag tactggacag cctgctggct
cagtatggta cagtagagaa ctgtgagcaa gtgaacaccg
agagtgagac ggcagtggtg aatgtcacct attccaaccg
ggagcagacc aggcaggctg acgaggttcc cctgaagatc
ctggcccata taactttgt agggcgtctc attggcaagg
aaggacgaa cctgaagaag gtagagcaag ataccgagac
aaaaatcacc atctcctcgt tgcaagacct taccctttac
aaccctgaga ggaccatcac tgtgaagggg gccatcgaga
attgttgcag ggccgagcag gaaataatga gaaaagttcg
ggaggcctat gagaatgatg tggctgccat gagcctgcag
tctcacctga tccctggcct gaacctggct gctgtaggtc
ttttcccagc ttcatccagc gcagtcccgc cgcctcccag
cagcgttact ggggctgctc cctatagctc ctttatgcag
gctcccgagc aggagatggt gcaggtgttt atccccgccc
aggcagtggg cgccatcatc ggcaagaagg ggcagcacat
caaacagctc tcccggtttg ccagcgcctc catcaagatt
gcaccaccg aaacacctga ctccaaagtt cgtatggtta
tcatcactgg accgccagag gcccaattca aggctcaggg
aagaatctat ggcaaactca aggaggagaa cttctttggt
cccaaggagg aagtgaagct ggagacccac atacgtgtgc
cagcatcagc agctggccgg tcattggca aaggtggaaa
aacggtgaac gagttgcaga atttgacggc agctgaggtg
gtagtaccaa gagaccagac ccctgatgag aacgaccagg
tcatcgtgaa aatcatcgga catttctatg ccagtcagat
ggctcaacgg aagatccgag acatcctggc ccaggttaag
cagcagcatc agaagggaca gagtaaccag gccccaggcac
ggaggaagtg accagcccct ccctgtccct tcgagtccag
gacaacaacg ggcagaaatc gagagtgtgc tctccccggc
aggcctgaga atgagtggga atccgggaca cctgggccgg
gctgtagatc aggttttgccc acttgattga gaaagatgtt
ccagtgagga accctgatct ctcagcccca aacacccacc
caattggccc aacactgtct gcccctcggg gtgtcagaaa
ttctagcgca aggcactttt aaacgtggat tgtttaaaga
agctctccag gccccaccaa gagggtggat cacacctcag
tgggaagaaa aataaaattt ccttcaggtt ttaaaaacat
gcagagaggt gttttaatca gccttaaagg atggttcatt
tcttgacctt aatgtttttc caatcttctt cccctactt
gggtaattga ttaaaatacc tccatttacg gcctctttct
atatttacac taattttttt atctttattg ctaccagaaa
```

-continued

```
aaaatgcgaa cgaatgcatt gctttgctta cagtattgac
tcaagggaaa agaactgtca gtatctgtag attaattcca
atcactccct aaccaatagg tacaatacgg aatgaagaag
aggggaaaat ggggagaaag atggttaaaa tacataataa
tccacgttta aaaggagcgc acttgtggct gatctatgcc
agatcaccat cttcaaattg gcacaactga aatttcccca
ctctgttggg gcttccccac cacattcatg tccctctccc
gtgtaggttt cacattatgt ccaggtgcac ataggtggta
ttgaatgctc agcagggtag gggctgacca ctgtccctga
ttcccatcgt tctcaggcgg attttatatt ttttttaaagt
ctattttaat gattggatat gagcactggg aaggggacgc
taactcccct tgataaagtc tcggttccat ggaggacttg
agtggcccca aaggctgcca cggtgccctc accccagccc
atgtgctccc ataagggctg gttcctagag gcaggggttg
tggggcactc ccagccacgg cactgttacc ttggtggtgg
gacttggaac ccaaccctga gctcccgata aagctaaagt
ccatcatctg gcaaattcag taaattggag agtacttgct
tctgtttgta tctgagagga attttttaact gacggcttct
gtctccatga atcattatca gcatgatgaa aggtgtgtct
aaaaaacaat tcagaatacc agcagcattg tacagcaagg
ggtaaataag cttaatttat taatttacca ggcttaatta
agatcccatg gagtgtttag cccttgtggg agacagaagc
catcagttaa atgaggttag gcctctcctc ctaatatact
gattgacaat gcatattagc caggtaatgc actttagcta
ccctggacaa tgctatcaag tgtgctggga agggaggaag
gcctctctac atatggaaaa gcccatgcgt ggagttcccc
tcctttcaac attgcaacaa cagtaacaac aagacaaccg
caacatgtgg gcgtagtcag gcaatgctgt gtgcgaagta
aactacctca aggtatgaag ttacctcagc aattattttc
cttttttgttc cccccaaccc cattaaaaaa attttttttt
gattttttgtt ttttttgcagc ttgctgatat tttatataaa
aaagaaaagc aaagcaaaag agaagctgat agtcttgaat
attttatttt tttaatgaaa agaaaaaaca agaaagttat
gtttcataat ttcttacaac atgagccagt aacccttag
gaactctcta tggagaacag gcctggtggg aaaggctttg
ggggctgccc ccttaggagg aggctagtgc taagagggaa
ggcccaggtt tgagagagcc cagaggggca gagcccagag
ccttgtttgg ccctgatctc tgacttctag agccccagct
gctggcggct gctgaatat cctacctgat aggattaaaa
ggcctagtgg agctggggc tctcagtggt taaacaatgc
ccaacaacca accagctggc cttggtctc ctctctttcc
tcctttggtt aaagagcatc tcagccagct tttcccacca
gtggtgctgt tgagatattt taaatatttg cctccgtttt
atcgaggaga gaaataataa ctaaaaaata tacccttaa
aaaaacctat atttctctgt ctaaaaatat gggagctgag
attccgttcg tggaaaaaag acaaggccac cctctcgccc
tcagagaggt ccacctggtt tgtcattgca atgcttttca
tttttttttt ttgttattgt ttcatttcag ttccgtcttg
tattcttcc taatctatat ccatagatct aagggggcaaa
cagatactag ttaactgccc cacctctgt ctccctgtct
tctttagatc ggtctgattg attttaaaag tggacccaaa
ttagggaat tcttgattta gggtggctgg tggcaaggag
gggcagggga tatggggacg tgactgggac aggttcctgc
cttatcattt tctccctagg acattccctt gtagccccca
gaattgtctg gcccaaattg aatagaagca gaaaaacatt
tagggataac atcaggccag tagaattaag cctctccacc
tgtcccaacc ataaaaaggg tctcccagct ttccatctct
ggctctatat gctttatccc aaaacaaagc agataacgtt
cagacgtcgg ccatttagta atttaaagcg aatttccagc
agcaagcatg ctttgatatc tggttcagac tatcatcagg
aagaaaaaaa aatcccacag tacctgaaat gtgattgttg
cagtgttcag tttccttggg ggcctgctcc cttcacacct
tgagcccaag tccttttccg ttggctgatt cagctcccag
aagagacgag gaagtgtgtg gcaagggact ggaaaacttc
acttgcttgg attaggcaag gctccactca ttgttgatat
ttgcccagca ggaaaatcat gtaagttata ccaccagaaa
gcaaaaggag catggtttgg tggttaaggt ttagtgggat
gaaggacctg tcttggtggg ccgggccctc ttgtgccccg
taggctaggt cttagggcaa ctccttgccc tcctgctcag
cacctccatt tcccatcct tggtgagata acaagctatc
gcgaaaagca cttgggagat ttggatgatt tgagaagagt
gacttaaaaa aaatgcttct gtgctctaag atatatatgt
gtgtgtgtgt gctacatata tattttttaag aaaggaccat
ctcttagga tatatttta aattctttga aacacataac
caaaatggtt tgattcactg actgactttg aagctgcatc
tgccagttac acccaaatg gctttaatcc cctctcgggt
ctggttgcct tttgcagttt gggttgtgga ctcagctcct
gtgagggtc tggttaggag agagccattt ttaaggacag
ggagtttat agccctttc tactttcctc ccctcctccc
agtccttatc aatctttttt ccttttcct gaccccctcc
ttctggaggc agttgggagc tatccttgtt tatgcctcac
tattggcaga aaagacccca tttaaaaccc agagaacact
```

-continued

```
ggaggggggat gctctagttg gttctgtgtc cattttcctc
tgtgccaaag acagacagac agaggctgag agaggctgtt
cctgaatcaa agcaatagcc agctttcgac acatacctgg
ctgtctgagg aggaaggcct cctggaaact gggagctaag
ggcgaggccc ttcccttcag aggctcctgg gggattaggg
tgtggtgttt gccaagccaa ggggtaggga gccgagaaat
tggtctgtcg gctcctggtt gcactttggg gaaggagagg
aagtttgggg ctccaggtag ctccctgttg tgggactgct
ctgtcccctg ccctactgc agagatagca ctgccgagtt
cccttcaggc ctggcagacg ggcagtgagg aggggcctca
gttagctctc aagggtgcct tcccctcctc ccaacccaga
cataccctct gccaaactgg gaaccagcag tgctagtaac
tacctcacag agcccagag ggcctgcttg agccttcttg
ctccacagga gaagctggtg cctctaggca accccttcct
cccacctctc atcaggggtg ggggttctcc tttcttttccc
ctgaagtgtt tatggggaga tcctagtggc tttgccattc
aaaccactcg actgtttgcc tgtttcttga aaaccagtag
aagggaaaca gcacagcctg tcacagtaat tgcaggaaga
ttgaagaaaa atcctcatca atgccagggg acataaaagc
catttcccttt ccaaatactc gacaatttag atgcagaaca
tttctctgta ttcagactta gagtaacacc agctgaaaac
tgcagtttct ttccttttgga tacataaggc ttctctatcg
gggtacggga cagggaggag gcctcatgtc tgaaggggga
ttaggggcg agagccccag ccctgaccct cggtcctgtg
caccgctttg gggcacagtc tgatggcgcc tttgctggcg
ccttagtatg gttgactccg gatggacaaa agaaaaaaaaa
ttttttttct tgaatgaaat agcaggaagc cctcgggag
catgtgtttt gattaaccgc aggtgatgga tgctacgagt
ataaatggat taactacctc aatccttaca gtaagattgg
aactaagggc agggactcat gcataagggt atgaatccca
gccaggacaa gtgagttgag gcttgtgcca caaaggttt
gtccttgggg aacaggcagg cctgccagga tcccccccat
atcgattggg ctgggaggcc tggccatgag gtccccactt
tctgctttcc ttgcccatgt gtcaccccttt tggcctccag
cttgtccctc tctcactttc tatagctttg ttggaccaga
tggtgaggaa aggaatgcc tcttcccttc tagagggggc
tggctggagt gagacctggg gcttggcctg gaacccacca
cacagcccca agtcaggaa gcctgggaa accagagctg
agacctcttc aacagggttt ctttgagatc ctacacctcc
attgggccct ttttcagtct tcaatggggg cccagttggc
tctagaagga gaagaggtga agcaggatcc tttgccctgg
```

```
gggagtctga gggcgcggtc cttggactca ttcaggccgt
cttgtagtt gggggagttc cactgggcga tcccagcccc
tccccaccca ccctctaatg gacctcctca tagaagcccc
atttcacttt tgttttatct acctcttagc aaaacaatag
ataaattagg tagtggcagc tccacttgct taggttaggg
ggggaaaaag atttcttttt ccaaaggaaa aaatattac
cttgagaata cttttccaaaa aataaaatta aaaaaaaaa
aaccaaaaaa aaaaattttt ttttaaaagg gagacatttt
ccagtgacca ctggattgtt ttaatttccc aagctttttt
ttcccccata aataagtttc actctttggc gatttcttc
acttgtttaa gataacgtgc tagctattcc aacaggtaac
agctttcaca gtctgcccct ggcctgtctc accccatccc
ccaccctatt cctgccagtg agtccttcct gtgcttctct
cccttctccc ctcccagcca gctgacttca gtcacccctg
tccccccctcc cctgccaata agctcccca ggaataaagg
ctttgttttg gggatgctta aatcttgact ggcacttccc
ggctgtgggg gctggggagc cacttgtaac atttctgtgc
agatttatg ttagccactg ctatgtaaaa gcacgttcaa
aatgaatttc agcagattat gtgttaccat aatgaataaa
cgtcctctat caccatttgg agtctccctt ttctccagga
tcttgatcct ggtccccaaa accagagtga atcaaaagag
cttcctcccc tgaggcaaag tggatttgta agcagttctg
aaacatcact tactcagaag agggaacgat gtattttgat
gagtgcaaat tgggaagagc tggaggccta ctgcttggga
cagttttttt ttttttttttt tttttaaata tgagtgctag
cttattctgt aattgcggca actttgaaaa ttgtatttta
ctggaaatct gccagccatc accacccgat tttgattgta
tccttcctcc catcctttaa tctgttcatt gctttgggg
aggtggggca gctggctcac acgttggagt ttgttctttg
atggatgaac gaacactcca gttttctttc ccgtgaaggt
tgtttcagcc acaaaccact tcattttgct gtttcaattt
caaaataaaa ggaaacttat attgaaagac aa
```

(MDM4) (NM_002393; protein is NP_002384.1)
SEQ ID NO: 8

```
gggaggccgg aagttgcggc ttcattactc gccatttcaa
aatgctgccg aggccctagg atctgtgact gccacccctc
cccccacccg ggctcggcgg gggagcgact catggagctg
ccgtaagttt taccaacaga ctgcagtttc ttcactacca
aaatgacatc attttccacc tctgctcagt gttcaacatc
tgacagtgct tgcaggatct ctcctggaca aatcaatcag
gtacgaccaa aactgccgct tttgaagatt ttgcatgcag
caggtgcgca aggtgaaatg ttcactgtta aagaggtcat
```

```
gcactatttta ggtcagtaca taatggtgaa gcaactttat
gatcagcagg agcagcatat ggtatattgt ggtggagatc
tttttgggaga actactggga cgtcagagct tctccgtgaa
agacccaagc cctctctatg atatgctaag aaagaatctt
gtcactttag ccactgctac tacagatgct gctcagactc
tcgctctcgc acaggatcac agtatggata ttccaagtca
agaccaactg aagcaaagtg cagaggaaag ttccacttcc
agaaaaagaa ctacagaaga cgatatcccc acactgccta
cctcagagca taaatgcata cattctagag aagatgaaga
cttaattgaa aatttagccc aagatgaaac atctaggctg
gaccttggat ttgaggagtg ggatgtagct ggcctgcctt
ggtggttttt aggaaacttg agaagcaact atacacctag
aagtaatggc tcaactgatt tacagacaaa tcaggatgtg
ggtactgcca ttgtttcaga tactacagat gacttgtggt
ttttgaatga gtcagtatca gagcagttag gtgttggaat
aaaagttgaa gctgctgata ctgaacaaac aagtgaagaa
gtagggaaag taagtgacaa aaaggtgatt gaagtgggaa
aaaatgatga cctggaggac tctaagtcct taagtgatga
taccgatgta gaggttacct ctgaggatga gtggcagtgt
actgaatgca agaaatttaa ctctccaagc aagaggtact
gttttcgttg ttgggccttg aggaaggatt ggtattcaga
ttgttcaaag ttaacccatt ctctctccac gtctgatatc
actgccatac ctgaaaagga aaatgaagga aatgatgtcc
ctgattgtcg aagaaccatt tcggctcctg tcgttagacc
taaagatgcg tatataaaga aagaaaactc caaacttttt
gatccctgca actcagtgga attcttggat ttggctcaca
gttctgaaag ccaagagacc atctcaagca tgggagaaca
gttagataac ctttctgaac agagaacaga tacagaaaac
atggaggatt gccagaatct cttgaagcca tgtagcttat
gtgagaaaag accacgagac gggaacatta ttcatggaag
gacgggccat cttgtcactt gttttcactg tgccagaaga
ctaaagaagg ctggggcttc atgcccatt tgcaagaaag
agattcagct ggttattaag gtttttatag cataatggta
gtacgaacat aaaaatgcat ttattccgtt cacttaccac
attatttgaa aatcaatcct ttatttaatt ttatttccaa
cctgtcagag aatgttctta ggcatcaaaa tccaaggtag
ctgtaagaaa aatactggag ctaacaatga agaacagaag
taatctgatt agtcaaatta ttaagtgcca tggattactt
tatgcagcag tcaggtacat agttaggtga acccaaaaga
aaaactcttg aaaacaagag atttcttcca tgcacattta
caatattgag gtataattaa catgataaag tgtttccttc
```

```
taacgagttg tagaaatctg agtaaccacc caaaaaagca
atagaatgtt tctgtcaccc caaaacactc ccttctgccc
ctcttcagac agtccttcag ctatttcatg gctctcaccc
tagttttttt ttttttttgca ctttttttttt tccggggggta
taggggaggt gtggggcgac agggtctgtc ttgttctgtc
tcccaggctg aagtgcagtg cagtggtatg atcatggctc
actgcagcct tggtttcctg ggcataagtg gtcttcccac
ttcagcctcc tgagtagctg agactataga ctagcataac
cacactggct aattttttgt ggagatgaag tctcactatg
ttgcccaggc tggtctcgaa ctcctgggct caaacaatcc
tcccgcctca gccttccaaa ttgctgggat tatagtcatg
aggcacctag tctggccctt ttgcaagact ttaatctgaa
atctaaattt ttaaaattta agtacttaca aaggatatac
tatccaacat attgcatatt atatatgtgc tttaaagttt
ttttttttttt ttgagagacg gtctcacttt gtcatccaag
ctggagtgca gtggtgcaaa cacggcccac ctcctgggct
caagtgatcc tccagcctca gcttccctca caggcattca
ctatcactcc cagctaatta aaataatttg tagacggtgt
ctcgttatgt tgcccaggct ggtctcgaac tcctgggttt
aagtgattcc cccgcctcag cctcccaaag tgttgggctt
acagccttga gccactatgc ttggctcaaa gatattttta
tgaaagccct gggactatag atttagctga ttaaatttat
agaaaaagtc ctgtcatata aactggcaaa gtctgttctt
aatttaatta gccaaatcag acttaacttc cgtcagaaca
tgtcttggtt ttaattcaga taaacacaca aacatacttc
tctggcacag ccttcagaag catcagtttt tgttttgttt
tgttttgttt tttgagacag ggtcttgctc tgtcgcccag
gctggagtgc actggcacaa tcacagttca ctgcagcctc
gacctcccag atccaagcaa tcctcccacc taagcctccc
aagtagctgg gtctataggc gcgtgccacc accatgccca
gctgaatttt gtattttttg tacagacagc attttgccat
gttgcccagg ctggtccaa acttctagcc tcaagcaacc
ctcctgcctc agcctctcaa agtgctagga ttgcagtcct
gagctactgc cccctaccct ctttgcgtct taggagtcat
ttagattttt tttgatcctt tgttttagtg cctctggagc
tgcttacacc aaggcaatac gccttgatat actggatggt
tgagaggcag cctctttttt tttttttttt tttttttttt
tttggaggat agggagtatg gctgttgtga aagggaggt
aaagagaaat ggtagatctg aagaggcctc atcagagcac
atattttagg acaacacata tggaaattgg acatctttaa
gttggtttcc atagagctat gcatgtatcc ttaccccat
```

```
gggaaaatgt tggtgtgttc tcaagggtat gcatgtgtca
ttttgaagac caaggccta gaattgtcaa acttaaggat
cataaaaatc atgagggttg cttgttaaaa atgtccaaac
gtgcagagac tgatcttga gatctggacc aggaatttgc
atttgaacaa gtgttcctgg aatctctatg caagttttat
acagaacata cttttggaat ccttgccta gacaggggtg
tccaatcttt tggcttccct ggtccacaat ggaagaagaa
ttgtcttgga ccacacataa aatacactaa cactaacaat
agctgatgag ctaaaaaaaa aaaaaaaaa aatcgtggac
cgggcgtagt ggctcacgcc tgtaatccca cactttggg
agatcaccta ggtcgggagt ttgagaccag cctgaccgac
atggagaaac cccattttta ctaaaaatac aaaaaattag
ctgggcatgg tggtgcatgc ctgtagtccc agctactcag
gaggctgagg caggagaatc gcttgaacct gagaggggga
gattgcggtg agctgagatt gcgccattgc accccagcct
gggcaacaat agcgaaactg tctcagaaaa agaaaaaaa
aaatcgcaaa aagaaaaatc tcataatgtc gttgttggtt
tttttttttt tttttgagac agtctcactc tgttgcccag
gctggagtgc aatggcatga tctctgctca ccgcaacctc
tgcctcccgg gttcaggtga ttctcctgcc tcagcctccc
agatagctgg gactacaggc acataccacc atgcctggct
aatttttgta ttttagtag agatggggt ttcactgtgt
tggccaggct ggtctcgaac tcctgacctc atgatccaca
cacctcggcc tcccaaagtc ctgcgattac aggcgtgagc
taccgcaccc agccaagttg aattttaa taaaacttaa
gaagtaaaca ttttacttat gtttataggt atttgatcct
aaatttgaca catcattgcc catgaaagaa tcctcttagg
ctgctcagct tcactcttcc tgcttgccca ccggggtttt
tcactgcttc tgttagcact aagtacttag acgatcctaa
gatatgtgct tgagccgaat ttcatctta cttgtaggaa
actttaaact attctttc tttcttttt tttttttt
tacttgagat ggagttttgc tcttgtcgcc caggctggag
tgcagtggag tgatctcggc tcactgcaac ctctgcctcc
cgggttcaaa tgattctcct gcctcagcct cccaagtagc
tgggattaca ggtgtgcacc accatgtctg gctaattttg
tatttttagt agagatggtt tcaccatgtt ggtcaggctg
gtctcgaact cctgacctca ggtcatccac ccacctcagc
ctcgcaaagt gctgagatta caggcatgag ccacagcgcc
cagcttaaac tattttcttg gtctgttttt gattttcttt
tttccttgcc actgcggtac agatttttt tactcactgc
cactaaacta aagcaaggca tagtttatat gtgaagtgtt
cagagtttac tgctataagg aaacttccaa atactgacat
ttaccttta gctgtagtta ttgggaccat gtgctctggt
tttctggaga ctgccaaatt gctcccattt ttctgcatcc
cacctggttt ctttctgcat gtccccttc actttcaaac
ctcttcattt ggatgttaaa ttatatggtc acctagttat
aggtaagcct tgttcgagtt gatatcttga ttgtgaggaa
ggatctgtgt cattggagct tgtttctgct gcaacgtgct
gtagactatg aataatgaaa tcacaccaca ttaccatcag
atttcttgtt ttagttgtca aattaatatt tatgattgtt
atcttgggcg aaaagttcag agcagagatg acaaatcatt
agaacaacga tgaatttcag tattacggct aaaaagttct
tctgtctgaa tattaactca ctctccttcc agtgtacttc
acagtaattg gtatgctttt ttatttaatg cttaaatcaa
actttataaa atcttagac cagatcttta atatggtatg
ccatttcccc agtctaccaa tggaatagta tgggtttcta
atcctaggct tgtacaatgg attggagttg agccatgcca
gcctccacac tgccactaac ttctgtaatg taagattgag
tcactgccaa gcatttgaaa tatgcagttg tgttttaatt
ataatttatg tatagttaga tgtatgtagt gcattgtgtg
gtattatttg gtttgtaaga atttattttt aagggtcaag
gtcatttgta acatttttgtg tgtgtcaatt caatgcaatg
ttggctgcct tttgaagtct ttgatatatt ggtgaatatt
cttctgatct ataatacaaa gctatgtaat gttacctctt
gactcgcttt tgaaaggaag acaattgtta actagatatt
tgagttttt cccctcagaa ttatgtgaat ttctgatata
tggctttaga tactgtgaat ctgttttcca tttagtcagt
tatctgctta aattgttcag aactatatcc taacgagcaa
ttagttctga tggttctccc agtcatgagt gtgcatgtgt
gcaagcatgt tttgatcctg atgctacctt tgctaaaaat
ggccatagat taggaactag ctatgttttt agaatcaaag
atgaaccggt aagctgtctc atgtaccaaa cgtgaaattt
acagtgttta caaatgtctg gaattttgca ctgccatagg
gaatgttaag gttacttggc tggaatttat cagacttgtg
agtaaacaag ttgaagttta gcagatgagg gggaatattg
aggcccctaa ggctaaacaa ataatcagt atctgagata
gtggctaatg tggctcccca ggcctaattt gggaacagtt
tttcctgatt gctttgagaa gtactttctt ttgacagaaa
ttttcattct gcttgccatt gctatattct ccctttatag
gagccattgg atttctttcc ttttgtggga aatgtcccat
tagcattttc agatcttttg atgtgcacta atgccattat
tggtaatgcc gttattggtg aatacagcat agttaaataa
```

-continued

```
actgttacag taaatctaca cttggatttg ctgcacctct
accaatagcc ttttgaatga ctgaaagtgt taacagagaa
agaggcatgt ctgcagaaag agatagctaa tatttttgg
tactttatct gaaatccaag atgctgcttc ccctgcaggt
tgttttcctt cttacgatcc tcattgaatc ccctctggga
gcacaggaca gttagtagaa ctctccattt cttttttttt
ttttttagac ggagtctctc tctgtcgccc cggctggagt
gcagtggcgc gatctcggct cactgcaacc tccgcctccc
gggttcaccc cattctcctg cctcagcctc cctagtagct
gggactatag gcgcccgcca ccacgcctgg ctaattttg
tattttatt ggagacgggg tttcaccgtc ttagccagga
tggtcttgat ctcctgacct cgtgatctgc ccacctcagc
ctcccaaagt actgggatta caggcgtgag ccaccgcgcc
cggccggaac tctccatttc ttaaggtaaa gagggtcaag
gatacctaaa aagggtcaaa taatgctaga agagcaattc
ctctttcaga gcagttgctg taatttggca aatgctttat
cgaagattga tattaggcta ggggcggtgg cttacgcctg
taatcccagc actttgggag gccgaggtgg gtggattgcc
tgagctcagg agttcgagac cagtctgacc agtatggtga
aaccctgtct ctactaaaaa tacaaaaatt agccggtcgt
ggtggcgtgc acctgtagtc ccagctactt ggcaggttga
gacaggagaa tcgcttgaac ctgggaggtg gaggttgcag
tgagccgaga ctgcaccact gcgctccac ctgggtgaca
gagactctgt ctcaaaaaaa aggacattta tcattataac
atcttattag agcccctaat ttcttatctg aaggcactgt
ttttttttt aaacagttaa gtactgatgt caacagacaa
atatttctga tcagatagtc ccctgtcaac agtagcaaat
gtggtttcat aaagtgggaa gaaaacagca ttttaaagta
acttttggg agactgattt gagtaataat aaaactctgg
tctcccttaa gaaaaaaaa cccttccacc tttactgtgt
catttatatc ccctagttc caaagttaat tatcttattt
ctggatattg cttttatacc aaagacccctt atcagccctt
gtaactacag tatctttaga taagattcct cttttccagtc
agtcctggga aatgtttctg ttgcagagtt aggcggtaga
tgggaagctg tgatggcaga gctactatct aataaagtaa
caactcgtag ttgaggcttc cttttctgtgt gtgatggggg
atagggagtt agctcccctg ttgtctcagc actaagaaat
tgaggtcagg ccaggcgcgg tggttcactc ctgttattcc
agcactgggg tggccaaagt gggcagattg cttgcgctct
ggagctcgag accagcctgg gcaacatggt gaaaccctgt
ctctaccaaa aatacaaaaa aaaagctggg catggtgggt
```

-continued

```
gcatgcttgt cccagctact gaggaggctg aggtgggagg
atcgcttgag cctgggaggt ggaggttgca gtgagctgag
atggcaccac tgcaatccaa ggtgggtgac agagacgctg
tctcaaagaa attgaggtca ggcttccttc ttacagaatt
atttttttct ctgtagtttg cctcattttt tcactttctt
ttcaatgaga atcgaagtgt ttcttttggg tttttttttc
ccccttttaa aatcaacagg aaatgtttca aaggagggat
gaaatgcttc ttggcttcct cagcacttgg caaggtagac
ctcatagcaa ccttgaatat gactttcttt agtctctagc
tatgcactat taagtgcctc ttgggtagag gtagagttaa
gtattgagtg ccagtcttga cgtccgtatg cctcagtttt
tctcatatat aaaaagcagt atacatacct acccttttct
acctcatcat ttgttgtagg gattaaatcc gggagagcaa
ttctgaagcc tataaatttc cttgaagaga tctaagaacc
tattatgctc ttggtgtacc aagctctggg gtatatattc
agaatacctc atgttctgga agctgagcac tagctcccct
ttattgcctg cctggcagag cctgtttgat tactgcaggc
ccttttaccc atgcttctag tttaggtatt ctttctttga
tatgaggctc ttgaccagaa aagagttctt tctctaggtg
ttctgagaga agtttgtaaa tttggatagt acattctatc
ctgataaaac caccttgctg tggtcttgat gtacaaaaaa
aaattttttt tttgagacag agtcttactc tgtcacccag
gctggaatgc agtggcgcaa tcttggttca ctgcaacccc
cgcctcctgg gttcaagcga tcctcctgcc tcaacctctc
aagtagctgg gactacaggc gtgcaccacc acacctggct
aattttgtat ttttagtaga cagggtttt caccatgttg
gccaggctgg tcttgaactc ctgacctcag gcgatctgcc
cgccttggcc tcccaaagta ctgggattac aggcgtgagc
aactgctcct ggcccaaaac atctctttct acatacactt
gagtaggtgg cataaaatgc actgtcaata tatagaaaac
atgaaatttt ccaaatattt ccgatcagag aatcacaaga
gcagcaaatg tggtttcat aagtgggaag aaagcagcaa
tttaaaataa cttttggga gactgaattg agtaataata
aaacttcagt ctttcgctaa taataataat aataataata
ataacaacaa cttattgaat gtgccagct cactagatga
ggaaagagga aggcattttc tgcattcttg cctagttttc
cttataagca ccactaagtt aatagctctg tcttttggt
gtttgcacta tgtaatgctt ttaatacttt ttaattgtgc
tttttatgt attaaatgtt tttccttttg cca
```

(CA VI)(NM_001215)

SEQ ID NO: 9

MRALVLLLSLFLLGGQAQHVSDWTYSEGALDEAHWPQHYPACG

GQRQSPINLQRTKVRYNPSLKGLNMTGYETQAGEFPMVNNGHT

VQISLPSTMRMTVADGTVYIAQQMHFHWGGASSEISGSEHTVD

GIRHVIEIHIVHYNSKYKSYDIAQDAPDGLAVLAAFVEVKNYP

ENTYYSNFISHLANIKYPGQRTTLTGLDVQDMLPRNLQHYYTY

HGSLTTPPCTENVHWFVLADFVKLSRTQVWKLENSLLDHRNKT

IHNDYRRTQPLNHRVVESNFPNQEYTLGSEFQFYLHKIEEILD

YLRRALN

All references, publications, patent applications, issued patents, accession records and databases cited herein, including in any appendices, are incorporated by reference in their entirety for all purposes.

We claim:

1. A method for diagnosing the presence of breast cancer in a subject at risk for developing breast cancer, the method comprising:
   a) analyzing a saliva sample from the subject at risk for developing breast cancer with an assay that specifically detects at least nine biomarkers in the saliva sample, wherein the nine biomarkers are S100A8 (S 100 calcium binding protein A8)(SEQ ID NO: 1), CSTA (cystatin A)(SEQ ID NO:2), GRM1 (glutamate receptor, metabotropic 1)(SEQ ID NO: 3), TPT1 (tumor protein, translationally-controlled 1)(SEQ ID NO:4), GRIK1 (glutamate receptor, ionotropic, kainate 1)(SEQ ID NO: 5), H6PD (hexose-6-phosphate dehydrogenase)(SEQ ID NO: 6), IGF2BP1 (insulin-like growth factor 2 mRNA binding protein 1)(SEQ ID NO: 7), MDM4 (3T3 cell double minute 4)(SEQ ID NO: 8), and CA6 (carbonic anhydrase VI)(SEQ ID NO: 9);
   b) detecting that the at least nine biomarkers are differentially expressed in the sample relative to a control sample from a subject without breast cancer, thereby detecting the presence of breast cancer in the subject; and
   c) administering a breast cancer treatment regimen to the subject, wherein the treatment regimen is selected from the group consisting of chemotherapy, hormonal therapy, radiotherapy, immunotherapy, and surgical removal of breast tissue.

2. The method of claim 1 wherein the assay detects a nucleic acid encoding at least one of the biomarkers of a), and wherein the nucleic acid is detected by mass spectroscopy, PCR, microarray hybridization, thermal sequencing, capillary array sequencing, or solid phase sequencing.

3. The method of claim 1 wherein the assay detects a polypeptide of CA6, and wherein the polypeptide is detected by ELISA, Western blot, flow cytometry, immunofluorescence, immunohistochemistry, or mass spectroscopy.

4. The method of claim 1, wherein the assay comprises a first and a second solid support, wherein the first solid support comprises capture binding probes selective for each of the following markers: S100A8, CSTA, GRM1, TPT1, GRIK1, H6PD, IGF2BP1 and MDM4, and wherein the second solid support comprises a capture binding probe selective for CA6.

5. The method of claim 4, wherein the capture binding probe selective for CA6 is an antibody.

* * * * *